US009802944B2

(12) United States Patent
Di Giorgio et al.

(10) Patent No.: US 9,802,944 B2
(45) Date of Patent: Oct. 31, 2017

(54) BICYCLIC COMPOUNDS AS AUTOTAXIN (ATX) AND LYSOPHOSPHATIDIC ACID (LPA) PRODUCTION INHIBITORS

(71) Applicant: Hoffmann-La Roche Inc., Little Falls, NJ (US)

(72) Inventors: Patrick Di Giorgio, Riehen (CH); Jerome Hert, Basel (CH); Daniel Hunziker, Moehlin (CH); Holger Kuehne, Loerrach (DE); Patrizio Mattei, Riehen (CH); Markus Rudolph, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/272,114

(22) Filed: Sep. 21, 2016

(65) Prior Publication Data

US 2017/0008900 A1 Jan. 12, 2017

Related U.S. Application Data

(63) Continuation of application No. PCT/EP2015/056032, filed on Mar. 23, 2015.

(30) Foreign Application Priority Data

Mar. 26, 2014 (EP) .................................... 14161760

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ............................ C07D 487/04; C07D 519/00
See application file for complete search history.

(56) References Cited

U.S. PATENT DOCUMENTS

| | | | |
|---|---|---|---|
| 3,392,149 A | 7/1968 | von der Emden et al. | |
| 6,821,964 B2 * | 11/2004 | Colon-Cruz ......... | C07D 487/04 514/210.16 |
| 6,841,560 B2 | 1/2005 | Thompson et al. | |
| 8,329,907 B2 | 12/2012 | Schultz et al. | |
| 9,493,486 B2 | 11/2016 | Hunziker et al. | |
| 2010/0298290 A1 | 11/2010 | Anand et al. | |
| 2012/0015959 A1 | 1/2012 | Staehle et al. | |
| 2012/0095040 A1 | 4/2012 | Abouabdellah et al. | |
| 2015/0353559 A1 | 12/2015 | Hert et al. | |
| 2015/0376194 A1 | 12/2015 | Hert et al. | |
| 2016/0264586 A1 | 9/2016 | Mattei et al. | |
| 2017/0008913 A1 | 1/2017 | Hunziker et al. | |
| 2017/0029425 A1 | 2/2017 | Hunziker et al. | |
| 2017/0050960 A1 | 2/2017 | Hert et al. | |

FOREIGN PATENT DOCUMENTS

| | | | |
|---|---|---|---|
| CN | 102459207 | A | 5/2012 |
| EP | 0 417 631 | A2 | 3/1991 |
| EP | 2 301 936 | A1 | 3/2011 |
| JP | 2001039950 | | 2/2001 |
| JP | 2008-501743 | | 1/2008 |
| JP | 2008-540547 | | 11/2008 |
| JP | 2009-161449 | | 7/2009 |
| JP | 2011-502150 | | 1/2011 |
| WO | 99/40070 | | 8/1999 |
| WO | 01/30780 | | 5/2001 |
| WO | 2004/074291 | A1 | 2/2004 |
| WO | 2005/040167 | A1 | 5/2005 |
| WO | 2005/121145 | | 12/2005 |
| WO | 2006/122137 | | 11/2006 |
| WO | 2007/030061 | A1 | 3/2007 |
| WO | 2007/049771 | | 5/2007 |
| WO | 2007/058322 | | 5/2007 |
| WO | 2007/103719 | | 9/2007 |
| WO | 2008/033456 | A2 | 3/2008 |
| WO | 2008/033764 | A2 | 3/2008 |
| WO | 2008/060767 | A2 | 5/2008 |
| WO | 2008/134141 | A1 | 11/2008 |
| WO | 2009/046841 | A2 | 4/2009 |
| WO | 2009/058347 | | 5/2009 |
| WO | 2010/028761 | | 3/2010 |
| WO | 2010/051977 | | 5/2010 |
| WO | 2010/055006 | A1 | 5/2010 |

(Continued)

OTHER PUBLICATIONS 1206969-43-8,Database Registry [retrieved online May 25, 2016] Chemical Abstracts Service, Feb. 22, 2010, BroadPharm: XP002707619, retrieved from STN Database accession No. 1206969-43-8 the whole document.
959567-58-9,Database Registry [retrieved online May 25, 2016] Chemical Abstracts Service Dec. 26, 2007, NIH Chemical Genomics Center: XP002707620, retrieved from STN Database accession No. 959567-58-9.
Albers et al., "Chemical Evolution of Autotaxin Hinhibitors" Chem Rev 112(5):2593-2603 (May 9, 2012).
Albers et al., "Chemical Evolution of Autotaxin Inhibitors" Chemical Reviews (XP055073234), 112(5):2593-2603 (May 9, 2012).
Barbayianni et al., "Autotaxin inhibitors: a patent review" Expert Opin Ther Patents 23(9):1123-1132 ( 2013).
Benesh et al., FEBS LETT 588:2712-2727 ( 2014).
CAS Registry Database, 1300725-30-7,Database Registry [retrieved online May 25, 2016] Chemical Abstracts Service May 25, 2011, Focus Synthesis LLC: XP002707618, retrieved from STN Database accession No. 1300725-30-7 the whole document.

(Continued)

*Primary Examiner* — Sudhakar Katakam
(74) *Attorney, Agent, or Firm* — Jonathan Duffield

(57) ABSTRACT

Compounds of formula (I)

(I)

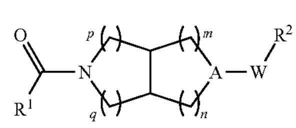

wherein $R^1$, $R^2$, A, W, m, n, p and q are as described herein, compositions including the compounds and methods of using the compounds as autotaxin inhibitors.

23 Claims, No Drawings

(56) References Cited

FOREIGN PATENT DOCUMENTS

| | | | |
|---|---|---|---|
| WO | 2010/099938 | | 9/2010 |
| WO | 2010/108651 | | 9/2010 |
| WO | 2010/112124 | A1 | 10/2010 |
| WO | 2010/115491 | A2 | 10/2010 |
| WO | 2010/130944 | A1 | 11/2010 |
| WO | 2010/135524 | | 11/2010 |
| WO | 2010/141817 | A1 | 12/2010 |
| WO | 2011/006569 | A1 | 1/2011 |
| WO | 2011/017561 | | 2/2011 |
| WO | 2011/085170 | | 7/2011 |
| WO | 2011/114271 | A1 | 9/2011 |
| WO | 2011/115813 | A1 | 9/2011 |
| WO | 2009/154132 | | 12/2011 |
| WO | 2011/151461 | A2 | 12/2011 |
| WO | 2012/020008 | | 2/2012 |
| WO | 2012/024620 | | 2/2012 |
| WO | 2012/028243 | | 3/2012 |
| WO | 2012/166415 | | 12/2012 |
| WO | 2013/033059 | A1 | 3/2013 |
| WO | 2013/054185 | A1 | 4/2013 |
| WO | 2013/064467 | A1 | 5/2013 |
| WO | 2013/065712 | A1 | 5/2013 |
| WO | 2013/175053 | | 11/2013 |
| WO | 2013/186159 | | 12/2013 |
| WO | 2014/018881 | | 1/2014 |
| WO | 2014/048881 | | 4/2014 |
| WO | 2014/055548 | | 4/2014 |
| WO | 2014/248865 | A1 | 4/2014 |
| WO | 2014/066659 | | 5/2014 |
| WO | 2014/139324 | | 9/2014 |
| WO | 2014/139978 | A1 | 9/2014 |
| WO | 2014/143579 | | 9/2014 |
| WO | 2014/152725 | A1 | 9/2014 |
| WO | 2014/164905 | | 10/2014 |
| WO | 2015/008230 | A1 | 1/2015 |
| WO | 2015/058031 | | 4/2015 |
| WO | 2016/162390 | | 10/2016 |
| WO | 2017/037146 | | 3/2017 |
| WO | 2017/050732 | | 3/2017 |
| WO | 2017/050747 | | 3/2017 |
| WO | 2017/050791 | | 3/2017 |
| WO | 2017/050792 | | 3/2017 |

OTHER PUBLICATIONS

CAS Registry Database, 1352926-14-7,Database Registry [retrieved online May 25, 2016] Chemical Abstracts Service Jan. 12, 2012, All i chern LLC: XP00270617, retrieved from STN Database accession No. 1352926-14-7 see also RN: 135295-74-6; the whole document.

Database Capulus (online) Chemical Abstracts Service Columbus Ohio, 1993, Database accession No. 1994:483155 RN156411-73-3, 156411-74-4 (1993).

Garcia-Gutierrez et al., "Novel inhibitors to Taenia solium Cu/Zn superoxide dismutase identified by virtual screening" J. Computer. Aided Molecular Design 25:1135-1145 ( 2011).

Gierse et al., Pharmacol Exp Ther 334:310-317 ( 2010).

Harald M.H.G. Albers et al., "Discovery and Optimization of Boronic Acid Based Inhibitors of Autotaxin" Journal of Medicinal Chemistry 53(13):4958-4967 (Jul. 8, 2010).

Hoeglund et al., "Optimization of a pidemidic acid autotaxin inhibitor" Journal of Medicinal Chemistry 53:1056-1066 (Dec. 30, 2009).

Jones et al., ACS MED CHEM LETT 7:857-861 ( 2016).

Kung et al., "Identification of spirocyclic piperidine-azetidine inverse agonists of the ghrelin receptor" Bioorganic & Medicinal Chemistry Letters (XP028490993), 22(13):4281-4287 (May 8, 2012).

Litherland et al., "The Amino-derivatives of Pentuerythritol. Part I. Preparation." (Published on Jan. 1, 1938. Downloaded by Roche Group on May 24, 2016 17:23:15.),:1588-1595.

Mayo Clinic Staff, (Lupus[online], retrieved from the internet on Jan. 24, 2017; http://www.mayoclinic.org/diseases-conditions/lupus basics/definitions/CON-20019676) 2017.

Orr et al., "One-pot synthesis of chiral azetidines from chloroaldehyde and chiral amines" Tetrahedron Letters (XP055073241), 52:3618-3620 ( 2011).

Overberger et al., "Absolute Configuration of 2,7-Diazaspiro[ 4.4lnonane. A Reassignment" J. Org. Chem. (XP055072840), 46:2757-2764 ( 1981).

Sippy et al., "Preparation and characterization of N-(3-pyridinyl) spirocyclic diamines as ligands for nicotinic acetylcholine receptors" Bioorganic & Medicinal Chemistry Letters 19:1682-1685 ( 2009).

Stocks et al., "A Practical Method for Targeted Library Design Balancing Lead-like Properties with Diversity" Chem Med Chem (XP002707616), 4:800-808 ( 2009).

* cited by examiner

BICYCLIC COMPOUNDS AS AUTOTAXIN (ATX) AND LYSOPHOSPHATIDIC ACID (LPA) PRODUCTION INHIBITORS

CROSS-REFERENCE TO RELATED APPLICATIONS

This application is a continuation of PCT/EP2015/056032 filed on Mar. 23, 2015, which claims priority to EP 14161760.5 filed on Mar. 26, 2014, the disclosures of which are incorporated herein by reference.

BACKGROUND OF THE INVENTION

Autotaxin (ATX) is a secreted enzyme also called ecto-nucleotide pyrophosphatase/phosphodiesterase 2 or lysophospholipase D that is important for converting lysophosphatidyl choline (LPC) to the bioactive signaling molecule lysophosphatidic acid (LPA). It has been shown that plasma LPA levels are well correlated with ATX activity and hence ATX is believed to be an important source of extracellular LPA. Early experiments with a prototype ATX inhibitor have shown that such a compound is able to inhibit the LPA synthesizing activity in mouse plasma. Work conducted in the 1970s and early 1980s has demonstrated that LPA can elicit a wide range of cellular responses; including smooth muscle cell contraction, platelet activation, cell proliferation, chemotaxis and others. LPA mediates its effects via signaling to several G protein coupled receptors (GPCRs); the first members were originally denoted Edg (endothelial cell differentiation gene) receptors or ventricular zone gene-1 (vzg-1) but are now called LPA receptors. The prototypic group now consists of LPA1/Edg-2/VZG-1, LPA2/Edg-4, and LPA3/Edg-7. Recently, three additional LPA receptors LPA4/p2y9/GPR23, LPA5/GPR92 and LPA6/p2Y5 have been described that are more closely related to nucleotide-selective purinergic receptors than to the prototypic LPA1-3 receptors. The ATX-LPA signaling axis is involved in a large range of physiological and pathophysiological functions, including, for example, nervous system function, vascular development, cardiovascular physiology, reproduction, immune system function, chronic inflammation, tumor metastasis and progression, organ fibrosis as well as obesity and/or other metabolic diseases such as diabetes mellitus. Therefore, increased activity of ATX and/or increased levels of LPA, altered LPA receptor expression and altered responses to LPA may contribute to the initiation, progression and/or outcome of a number of different pathophysiological conditions related to the ATX/LPA axis.

SUMMARY OF THE INVENTION

The present invention relates to organic compounds useful for therapy or prophylaxis in a mammal, and in particular to autotaxin (ATX) inhibitors which are inhibitors of lysophosphatidic acid (LPA) production and thus modulators of LPA levels and associated signaling, for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

The present invention provides novel compounds of formula (I)

(I)

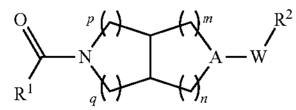

wherein $R^1$ is substituted phenyl or substituted pyridinyl, wherein substituted phenyl and substituted pyridinyl are substituted with $R^3$, $R^4$ and $R^5$;

A is —N— or —CH—;

W is —C(O)—, —C(O)O—, —$S(O)_2$—, —C(O)—$NR^{10}$— or —$CR^6R^7$—;

$R^2$ is selected from the ring systems B, C, D, E, F, G, H, I, J, K, L, M, N, O, P, Q, R, S, T, U, V, X, Z, AA, AB, AC, AD, AE, AF, AG, AH, AI, AJ, AK, AL, AM, AN, AO, AP, AQ, AR, AS, AT, AU and AV;

B

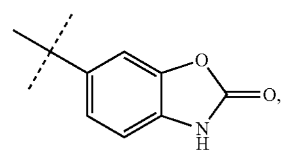

C

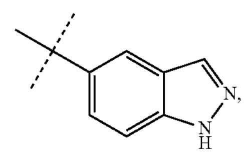

D

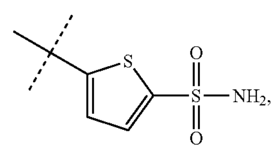

E

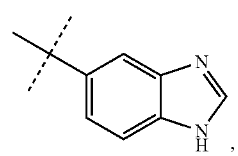

F

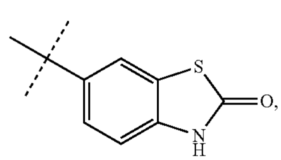

G

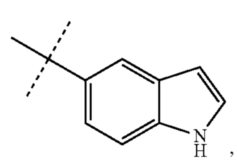

H

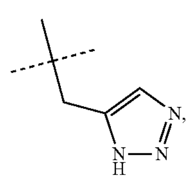

-continued
I
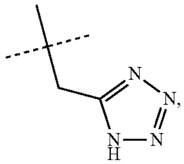
J
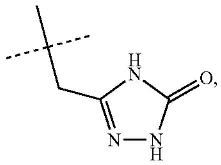
K
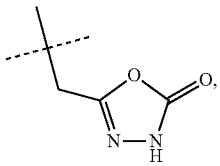
L
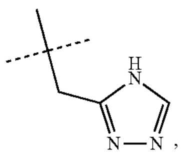
M
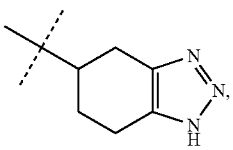
N
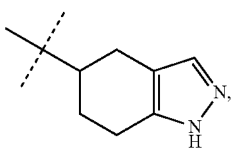
O
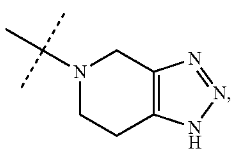
P
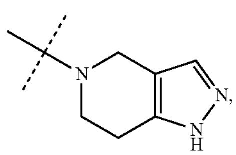
Q
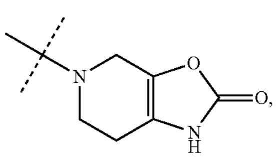
R
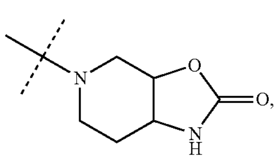
-continued
S
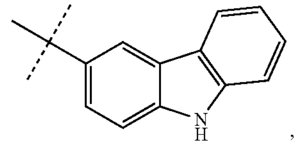
T
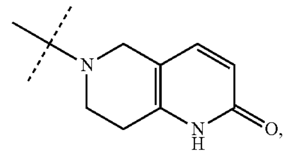
U
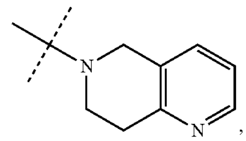
V
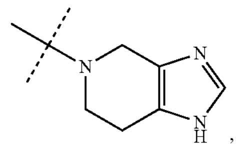
X
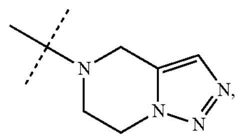
Z
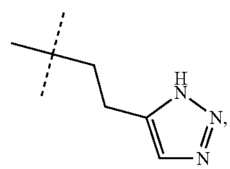
AA
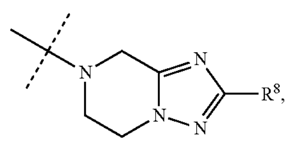
AB
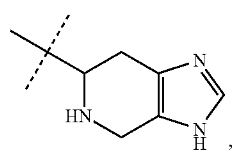
AC
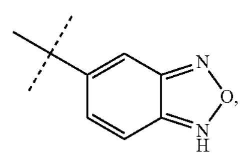
AD
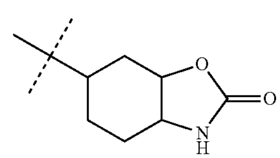

-continued

AE

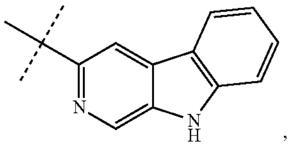

AF

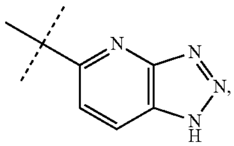

AG

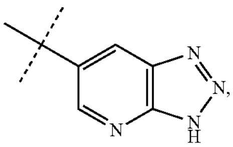

AH

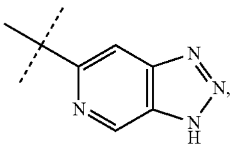

AI

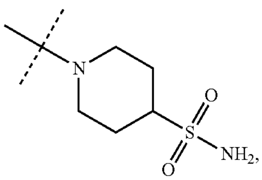

AJ

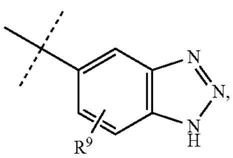

AK

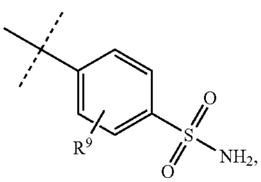

AL

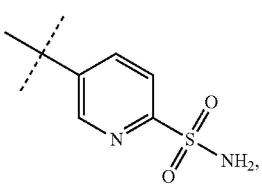

AM

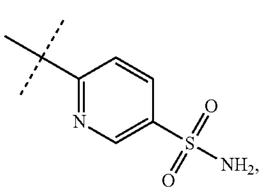

-continued

AN

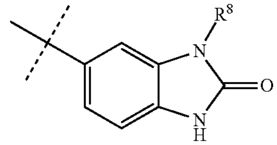

AO

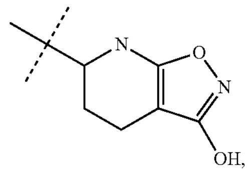

AP

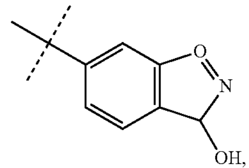

AQ

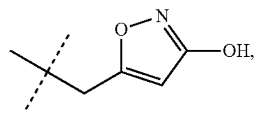

AR

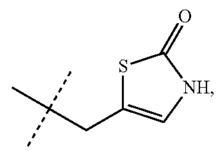

AS

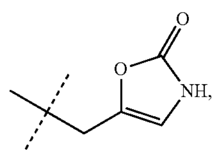

AT

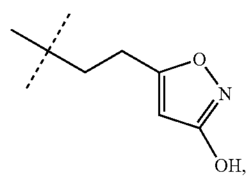

AU

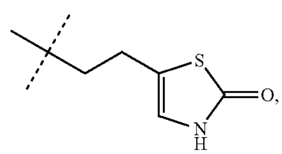

AV

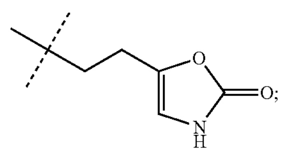

$R^3$ is substituted heterocycloalkoxy, substituted heterocycloalkylalkoxy, substituted heterocycloalkyl amino or substituted heterocycloalkylalkylamino, wherein substituted heterocycloalkoxy, substituted heterocycloalkylalkoxy, substituted heterocycloalkylamino and substituted heterocycloalkylalkylamino are substituted with $R^{11}$, $R^{12}$ and $R^{13}$;

$R^4$ and $R^5$ are independently selected from H, amino, alkylamino, dialkylamino, alkyl, haloalkyl, cycloalkyl, cycloalkylalkyl, halogen and cyano;

m, n, p and q are independently selected from 1 or 2;

$R^6$ and $R^7$ are independently selected from H or alkyl;

$R^8$ is H, alkyl, haloalkyl or cycloalkyl;

$R^9$ is H, alkyl, halogen, haloalkyl and alkoxy;

$R^{10}$ is H or alkyl;

$R^{11}$, $R^{12}$ and $R^{13}$ are independently selected from H, alkyl, alkoxy, cycloalkyl, cycloalkoxy, halogen, haloalkyl, and cyano;

or pharmaceutically acceptable salts.

In accordance with the invention, the compounds of formula (I) or their pharmaceutically acceptable salts and esters can be used for the treatment or prophylaxis of diseases, disorders or conditions that are associated with the activity of autotaxin and/or the biological activity of lysophosphatidic acid (LPA).

The compounds of formula (I) or their pharmaceutically acceptable salts and esters herein inhibit autotaxin activity and therefore inhibit LPA production and modulate LPA levels and associated signaling. Autotaxin inhibitors described herein are useful as agents for the treatment or prevention of diseases or conditions in which ATX activity and/or LPA signaling participates, is involved in the etiology or pathology of the disease, or is otherwise associated with at least one symptom of the disease. The ATX-LPA axis has been implicated for example in angiogenesis, chronic inflammation, autoimmune diseases, fibrotic diseases, cancer and tumor metastasis and progression, ocular conditions, metabolic conditions such as obesity and/or diabetes mellitus, conditions such as cholestatic or other forms of chronic pruritus as well as acute and chronic organ transplant rejection.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of ATX and/or the biological activity of lysophosphatidic acid (LPA), particularly in the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and- chronic organ transplant rejection, and the use of the said compounds, salts or esters for the production of medicaments for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

DETAILED DESCRIPTION OF THE INVENTION

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, tert-butyl and pentyl. Particular alkyl groups include methyl, ethyl, propyl and isopropyl.

The term "alkylamino" denotes a group of the formula —NH—R', wherein R' is an alkyl group. Examples of alkylamino group include methylamino, ethylamino, n-propylamino, isopropylamino, n-butylamino, isobutylamino and tert-butylamino.

The term "amino" denotes a $—NH_2$ group.

The term "cyano" denotes a —C≡N group.

The term "cycloalkoxy" denotes a group of the formula —O—R', wherein R' is a cycloalkyl group. Examples of cycloalkoxy group include cyclopropoxy, cyclobutoxy, cyclopentyloxy, cyclohexyloxy, cycloheptyloxy and cyclooctyloxy. Particular cycloalkoxy group is cyclopropoxy.

The term "cycloalkyl" denotes a monovalent saturated monocyclic or bicyclic hydrocarbon group of 3 to 10 ring carbon atoms. In particular embodiments, cycloalkyl denotes a monovalent saturated monocyclic hydrocarbon group of 3 to 8 ring carbon atoms. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl groups are cyclopropyl, cyclobutanyl, cyclopentyl and cyclohexyl. More particular monocyclic cycloalkyl group is cyclopropyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclopropylbutyl, cyclobutylpropyl, 2-cyclopropylbutyl, cyclopentylbutyl, cyclohexylmethyl, cyclohexylethyl, bicyclo[4.1.0]heptanylmethyl, bicyclo[4.1.0]heptanylethyl, bicyclo[2.2.2]octanylmethyl, bicyclo[2.2.2]octanylethyl, adamentanylmethyl and adamantanylethyl. Particular examples of cycloalkylalkyl are cyclohexylmethyl, cyclohexylethyl, bicyclo[4.1.0]heptanylmethyl, bicyclo[4.1.0]heptanylethyl, bicyclo[2.2.2]octanylmethyl, bicyclo[2.2.2]octanylethyl, adamentanylmethyl and adamantanylethyl. Further particular examples cycloalkylalkyl are cyclohexylmethyl, cyclohexylethyl, bicyclo[4.1.0]heptanylmethyl, bicyclo[2.2.2]octanylmethyl, adamentanylmethyl and adamantanylethyl.

The term "dialkylamino" denotes a group of the formula —N—R'R", wherein R' and R" are independently selected alkyl groups. Particular of dialkylamino group is dimethylamino.

The term "haloalkyl" denotes an alkyl group wherein at least one of the hydrogen atoms of the alkyl group has been replaced by the same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl group is trifluoromethyl.

The term "halogen" and "halo" are used interchangeably herein and denote fluoro, chloro, bromo, or iodo. Particular halogen is fluoro.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are 4,5-dihydro-oxazolyl, oxetanyl, azetidinyl, pyrrolidinyl, 2-oxo-pyrrolidin-3-yl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Particular example of heterocycloalkyl groups are tetrahydropyranyl, tetrahydrofuranyl and oxetanyl.

The term "heterocycloalkoxy" denotes a group of the formula —O—R', wherein R' is a heterocycloalkyl group. Examples of heterocycloalkoxy group include tetrahydropyranyloxy, tetrahydrofuranyloxy and oxetanyloxy. Particular heterocycloalkoxy group is tetrahydropyranyloxy.

The term "heterocycloalkylalkoxy" denotes an alkoxy group wherein at least one of the hydrogen atoms of the alkoxy group is replaced by a heterocycloalkyl group. Examples of heterocycloalkylalkoxy include tetrahydropyranylmethoxy, tetrahydrofuranylmethoxy, oxetanylmethoxy, tetrahydropyranylethoxy, tetrahydrofuranylethoxy and oxetanylethoxy. Particular heterocycloalkylalkoxy is tetrahydropyranylmethoxy.

The term "heterocycloalkylalkylamino" denotes an alkylamino group wherein at least one of the hydrogen atoms of the alkylamino group is replaced by a heterocycloalkyl group. Examples of heterocycloalkylalkylamino include tetrahydropyranylmethyl amino, tetrahydrofuranylmethylamino, oxetanylmethylamino, tetrahydropyranyl ethylamino, tetrahydrofuranylethylamino and oxetanylethylamino.

The term "heterocycloalkylamino" denotes a group of the formula —NH—R', wherein R' is a heterocycloalkyl group. Examples of heterocycloalkylamino group include tetrahydropyranyl amino, tetrahydrofuranylamino and oxetanylamino. Particular heterocycloalkylamino group is tetrahydropyranylamino.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol M.

The abbreviation uL means microliter and is equivalent to the symbol μL.

The abbreviation ug means microgram and is equivalent to the symbol μg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

In an embodiment of the present invention are compounds according to formula (I) as described herein, wherein $R^1$ is substituted phenyl or substituted pyridinyl, wherein substituted phenyl and substituted pyridinyl are substituted with $R^3$, $R^4$ and $R^5$;

A is —N— or —CH—;

W is —C(O)—, —$S(O)_2$—, —C(O)—$NR^{10}$— or —$CR^6R^7$—;

$R^2$ is selected from the ring systems B, C, D, E, F, G, H, I, J, K, L, M, N, O, P, Q, R, S, T, U, V, X, Z, AA, AB, AC, AD, AE, AF, AG, AH, AI, AJ, AK wherein $R^9$ is H, AL and AM;

$R^3$ is substituted heterocycloalkoxy, substituted heterocycloalkylalkoxy, substituted heterocycloalkyl amino or substituted heterocycloalkylalkylamino, wherein substituted heterocycloalkoxy, substituted heterocycloalkylalkoxy, substituted heterocycloalkylamino and substituted heterocycloalkylalkylamino are substituted with $R^{11}$, $R^{12}$ and $R^{13}$;

$R^4$ and $R^5$ are independently selected from H, alkyl, haloalkyl, cycloalkyl, cycloalkylalkyl, halogen and cyano;

m, n, p and q are independently selected from 1 or 2;

$R^8$ is H, alkyl, haloalkyl or cycloalkyl;

$R^9$ is H, alkyl, halogen, haloalkyl and alkoxy;

$R^{10}$ is H or alkyl;

$R^{11}$, $R^{12}$ and $R^{13}$ are independently selected from H, alkyl, alkoxy, cycloalkyl, cycloalkoxy, halogen, haloalkyl, and cyano;

or pharmaceutically acceptable salts.

Another embodiment of the present invention are compounds according to formula (I) as described herein, wherein $R^1$ is pyridinyl substituted with $R^3$, $R^4$ and $R^5$.

Also an embodiment of the present invention are compounds according to formula (I) as described herein, wherein $R^3$ is substituted heterocycloalkoxy, substituted heterocycloalkylalkoxy or substituted heterocycloalkylamino, wherein substituted heterocycloalkoxy, substituted heterocycloalkylalkoxy and substituted heterocycloalkylamino are substituted with $R^{11}$, $R^{12}$ and $R^{13}$.

A particular embodiment of the present invention are compounds according to formula (I) as described herein, wherein $R^3$ is tetrahydropyranyloxy, tetrahydrofuranyloxy, oxetanyloxy, tetrahydropyranylmethoxy or tetrahydropyranylamino.

In a further particular embodiment of the present invention are compounds according to formula (I) as described herein, wherein $R^3$ is substituted heterocycloalkoxy or substituted heterocycloalkylalkoxy, wherein substituted heterocycloalkoxy and substituted heterocycloalkylalkoxy are substituted with $R^{11}$, $R^{12}$ and $R^{13}$.

A more particular embodiment of the present invention are compounds according to formula (I) as described herein, wherein $R^3$ is tetrahydropyranyloxy, tetrahydrofuranyloxy, oxetanyloxy or tetrahydropyranylmethoxy.

A further more particular embodiment of the present invention are compounds according to formula (I) as described herein, wherein $R^3$ is heterocycloalkylkoxy substituted with $R^{11}$, $R^{12}$ and $R^{13}$.

A further more particular embodiment of the present invention are compounds according to formula (I) as described herein, wherein $R^3$ is tetrahydropyranylmethoxy.

The present invention also relates to compounds according to formula (I) as described herein, wherein $R^4$ is dialkylamino, haloalkyl, cycloalkyl or halogen.

A further particular embodiment of the present invention relates to compounds according to formula (I) as described herein, wherein $R^4$ is haloalkyl or cycloalkyl.

A more particular embodiment of the present invention are compounds according to formula (I) as described herein, wherein $R^4$ is cycloalkyl.

Another embodiment of the present invention are compounds according to formula (I) as described herein, wherein $R^5$ is H.

Also an embodiment of the present invention are compounds according to formula (I) as described herein, wherein $R^{11}$, $R^{12}$ and $R^{13}$ are H.

Also an embodiment of the present invention are compounds according to formula (I) as described herein, wherein A is —N—.

Another embodiment of the present invention are compounds according to formula (I) as described herein, wherein W is —C(O)—, —C(O)O—, —C(O)—$NR^{10}$— or —$CR^6R^7$—.

A particular embodiment of the present invention are compounds according to formula (I) as described herein, wherein W is —C(O)—.

Another embodiment of the present invention are compounds according to formula (I) as described herein, wherein $R^2$ is selected from the ring systems B, H, M, O, Z, AI, AJ, AK, AL, AM, AN, AO, AQ and AT.

A particular embodiment of the present invention are compounds according to formula (I) as described herein, wherein $R^2$ is selected from the ring systems B, M, O, AJ, AK, AL, AM, AN and AO.

A further particular embodiment of the present invention are compounds according to formula (I) as described herein, wherein $R^2$ is selected from the ring systems M, AJ, AK, AL and AM.

A more particular embodiment of the present invention are compounds according to formula (I) as described herein, wherein $R^2$ is selected from the ring systems M, AJ and AL.

A furthermore particular embodiment of the present invention are compounds according to formula (I) as described herein, wherein $R^2$ is the ring system AJ.

A particular embodiment of the present invention are compounds according to formula (I) as described herein, wherein m and n are 1 and p and q are 2.

A more particular embodiment of the present invention are compounds according to formula (I) as described herein, wherein $R^1$ is pyridinyl substituted with $R^3$, $R^4$ and $R^5$;

A is —N—;

W is —C(O)—;

$R^2$ is the ring system AJ;

$R^3$ is heterocycloalkylalkoxy substituted with $R^{11}$, $R^{12}$ and $R^{13}$;

$R^4$ is cycloalkyl;

$R^5$ is H;

m and n are 1;

p and q are 2;

$R^9$ is H;

$R^{11}$, $R^{12}$ and $R^{13}$ are H;

or pharmaceutically acceptable salts. Particular examples of compounds of formula (I) as described herein are selected from 5-((3aS,6aS)-5-(5-cyclopropyl-6-(tetrahydro-2H-pyran-4-yl oxy)nicotinoyl)octahydropyrrolo[3,4-c]pyrrole-2-carbonyl)pyridine-2-sulfonamide;

6-((3aR,6aR)-5-(5-cyclopropyl-6-(tetrahydro-2H-pyran-4-yloxy)nicotinoyl)octahydropyrrolo[3,4-c]pyrrole-2-carbonyl)pyridine-3-sulfonamide;

4-((3aS,6aS)-5-(5-cyclopropyl-6-(tetrahydro-2H-pyran-4-yloxy)nicotinoyl)octahydropyrrolo[3,4-c]pyrrole-2-carbonyl)benzenesulfonamide;

4-((3aR,6aS)-5-(5-cyclopropyl-6-(tetrahydro-2H-pyran-4-yloxy)nicotinoyl)octahydropyrrolo[3,4-c]pyrrole-2-carbonyl)benzenesulfonamide;

((3aS,6aS)-5-(1H-benzo[d][1,2,3]triazole-5-carbonyl)hexahydropyrrolo[3,4-c]pyrrol-2(1H)-yl)(2-cyclopropyl-6-((tetrahydro-2H-pyran-4-yl)methoxy)pyridin-4-yl)methanone;

((3aS,6aS)-5-(3-cyclopropyl-4-(tetrahydrofuran-3-yl oxy) benzoyl)hexahydropyrrolo[3,4-c]pyrrol-2(1H)-yl)((R)-4,5,6,7-tetrahydro-1H-benzo[d][1,2,3]triazol-5-yl)methanone;

((3aR,6aR)-5-(1H-benzo[d]d[1,2,3]triazole-5-carbonyl) hexahydropyrrolo[3,4-c]pyrrol-2(1H)-yl)(3-cyclopropyl-4-(tetrahydrofuran-3-yloxy)phenyl)methanone;

((3aS,6aS)-5-(1H-benzo[d][1,2,3]triazole-5-carbonyl)hexahydropyrrolo[3,4-c]pyrrol-2(1H)-yl)(5-cyclopropyl-6-(tetrahydro-2H-pyran-4-ylamino)pyridin-3-yl)methanone;

((3aS,6aS)-5-(1H-benzo[d][1,2,3]triazole-5-carbonyl)hexahydropyrrolo[3,4-c]pyrrol-2(1H)-yl)(5-cyclopropyl-6-(tetrahydrofuran-3-yloxy)pyridin-3-yl)methanone;

((3aS,6aS)-5-(1H-benzo[d][1,2,3]triazole-5-carbonyl)hexahydropyrrolo[3,4-c]pyrrol-2(1H)-yl)(5-cyclopropyl-6-(tetrahydro-2H-pyran-3-yloxy)pyridin-3-yl)methanone;

((3aS,6aS)-5-(1H-benzo[d][1,2,3]triazole-5-carbonyl)hexahydropyrrolo[3,4-c]pyrrol-2(1H)-yl)(5-cyclopropyl-6-(tetrahydro-2H-pyran-4-yloxy)pyridin-3-yl)methanone;

((3aS,6aS)-5-(1H-benzo[d][1,2,3]triazole-5-carbonyl)hexahydropyrrolo[3,4-c]pyrrol-2(1H)-yl)(6-(oxetan-3-yloxy)-5-(trifluoromethyl)pyridin-3-yl)methanone;

((3aS,6aS)-5-(5-cyclopropyl-6-(tetrahydro-2H-pyran-4-yloxy)nicotinoyl)hexahydropyrrolo[3,4-c]pyrrol-2(1H)-yl)((R)-4,5,6,7-tetrahydro-1H-benzo[d][1,2,3]triazol-5-yl)methanone;

4-((3aR,6aR)-5-(2-cyclopropyl-6-((tetrahydro-2H-pyran-4-yl)methoxy)isonicotinoyl)octahydropyrrolo[3,4-c]pyrrole-2-carbonyl)-2-fluorobenzenesulfonamide;

2-chloro-4-((3aR,6aR)-5-(2-cyclopropyl-6-((tetrahydro-2H-pyran-4-yl)methoxy)isonicotinoyl)octahydropyrrolo[3,4-c]pyrrole-2-carbonyl)benzenesulfonamide;

4-((3aR,6aR)-5-(2-cyclopropyl-6-((tetrahydro-2H-pyran-4-yl)methoxy)isonicotinoyl)octahydropyrrolo[3,4-c]pyrrole-2-carbonyl)-3-fluorobenzenesulfonamide;

((3aR,8aS)-2-(1H-benzo[d][1,2,3]triazole-5-carbonyl)octahydropyrrolo[3,4-d]azepin-6(7H)-yl)(2-cyclopropyl-6-((tetrahydro-2H-pyran-4-yl)methoxy)pyridin-4-yl)methanone;

4-((3aS,6aS)-5-(2-cyclopropyl-6-((tetrahydro-2H-pyran-4-yl)methoxy)isonicotinoyl)octahydropyrrolo[3,4-c]pyrrole-2-carbonyl)benzenesulfonamide;

4-((3aR,8aS)-6-(2-cyclopropyl-6-((tetrahydro-2H-pyran-4-yl)methoxy)isonicotinoyl)decahydropyrrolo[3,4-d]azepine-2-carbonyl)benzenesulfonamide;

((3aS,6aS)-5-(1H-benzo[d][1,2,3]triazole-5-carbonyl)hexahydropyrrolo[3,4-c]pyrrol-2(1H)-yl)(5-cyclopropyl-6-((tetrahydro-2H-pyran-4-yl)methoxy)pyridin-3-yl)methanone;

((3aS,6aS)-5-(5-cyclopropyl-6-((tetrahydro-2H-pyran-4-yl) methoxy)nicotinoyl)hexahydropyrrolo[3,4-c]pyrrol-2(1H)-yl)((R)-4,5,6,7-tetrahydro-1H-benzo[d][1,2,3]triazol-5-yl)methanone;

1-((3aS,6aS)-5-(2-cyclopropyl-6-((tetrahydro-2H-pyran-4-yl)methoxy)isonicotinoyl)hexahydropyrro[3,4-c]pyrrol-2(1H)-yl)-3-(1H-1,2,3-triazol-5-yl)propan-1-one;

((3aR,8aS)-2-(1H-benzo[d][1,2,3]triazole-5-carbonyl)octahydropyrrolo[3,4-d]azepin-6(2H)-yl)(3-cyclopropyl-5-((tetrahydro-2H-pyran-4-yl)methoxy)phenyl)methanone;

1-((3aR,8aS)-6-(3-cyclopropyl-5-((tetrahydro-2H-pyran-4-yl)methoxy)benzoyl)octahydropyrrolo[3,4-d]azepin-2(1H)-yl)-3-(1H-1,2,3-triazol-4-yl)propan-1-one;

((3aS,6aS)-5-(3-cyclopropyl-5-((tetrahydro-2H-pyran-4-yl) methoxy)benzoyl)hexahydropyrrolo[3,4-c]pyrrol-2(1H)-yl)((R)-4,5,6,7-tetrahydro-1H-benzo[d][1,2,3]triazol-5-yl)methanone;

4-((3aS,6aS)-5-(3-cyclopropyl-5-((tetrahydro-2H-pyran-4-yl)methoxy)benzoyl)octahydropyrrolo[3,4-c]pyrrole-2-carbonyl)benzenesulfonamide;

4-((3aR,6aR)-5-(3-cyclopropyl-5-((tetrahydro-2H-pyran-4-yl)methoxy)benzoyl)octahydropyrrolo[3,4-c]pyrrole-2-carbonyl)-3-fluorobenzenesulfonamide;

5-((3aR,8aS)-6-(2-cyclopropyl-6-((tetrahydro-2H-pyran-4-yl)methoxy)isonicotinoyl)decahydropyrrolo[3,4-d]azepine-2-carbonyl)-1H-benzo[d]imidazol-2(3H)-one;

6-((3aR,8aS)-6-(2-cyclopropyl-6-((tetrahydro-2H-pyran-4-yl)methoxy)isonicotinoyl)decahydropyrrolo[3,4-d]azepine-2-carbonyl)-1-methyl-1H-benzo[d]imidazol-2(3H)-one;

5-(3-((3aR,8aS)-6-(2-cyclopropyl-6-((tetrahydro-2H-pyran-4-yl)methoxy)isonicotinoyl)octahydropyrrolo[3,4-d]azepin-2(1H)-yl)-3-oxopropyl)oxazol-2(3H)-one;

5-(3-((3aR,8aS)-6-(2-cyclopropyl-6-((tetrahydro-2H-pyran-4-yl)methoxy)isonicotinoyl)octahydropyrrolo[3,4-d]azepin-2(1H)-yl)-3-oxopropyl)thiazol-2(3H)-one;

1-((3aR,8aS)-6-(2-cyclopropyl-6-((tetrahydro-2H-pyran-4-yl)methoxy)isonicotinoyl)octahydropyrrolo[3,4-d]azepin-2(1H)-yl)-3-(3-hydroxyisoxazol-5-yl)propan-1-one;

((3aS,6aS)-5-(2-cyclopropyl-6-((tetrahydro-2H-pyran-4-yl) methoxy)isonicotinoyl)hexahydropyrrolo[3,4-c]pyrrol-2(1H)-yl)((R)-4,5,6,7-tetrahydro-1H-benzo[d][1,2,3]triazol-5-yl)methanone;

((3aS,6aS)-5-(5-cyclopropyl-6-(tetrahydro-2H-pyran-4-ylamino)nicotinoyl)hexahydropyrrolo[3,4-c]pyrrol-2(1H)-yl)((R)-4,5,6,7-tetrahydro-1H-benzo[d][1,2,3]triazol-5-yl)methanone;

((3aS,6aS)-5-(5-cyclopropyl-6-(tetrahydro-2H-pyran-3-yloxy)nicotinoyl)hexahydropyrrolo[3,4-c]pyrrol-2(1H)-yl)((R)-4,5,6,7-tetrahydro-1H-benzo[d][1,2,3]triazol-5-yl)methanone;

6-((3aR,6aR)-5-(5-cyclopropyl-6-(tetrahydro-2H-pyran-3-yloxy)nicotinoyl)octahydropyrrolo[3,4-c]pyrrole-2-carbonyl)pyridine-3-sulfonamide;

6-((3aR,6aR)-5-(2-cyclopropyl-6-((tetrahydro-2H-pyran-4-yl)methoxy)isonicotinoyl)octahydropyrrolo[3,4-c]pyrrole-2-carbonyl)pyridine-3-sulfonamide;

((3aS,6aS)-5-(1H-benzo[d][1,2,3]triazole-5-carbonyl)hexahydropyrrolo[3,4-c]pyrrol-2(1H)-yl)(2-cyclopropyl-6-((tetrahydro-2H-pyran-3-yl)methoxy)pyridin-4-yl)methanone;

((3aS,6aS)-5-(2-cyclopropyl-6-((tetrahydro-2H-pyran-3-yl) methoxy)isonicotinoyl)hexahydropyrrolo[3,4-c]pyrrol-2(1H)-yl)((R)-4,5,6,7-tetrahydro-1H-benzo[d][1,2,3]triazol-5-yl)methanone;

6-((3aR,6aR)-5-(2-cyclopropyl-6-((tetrahydro-2H-pyran-3-yl)methoxy)isonicotinoyl)octahydropyrrolo[3,4-c]pyrrole-2-carbonyl)pyridine-3-sulfonamide;

((3aS,6aS)-5-((1H-benzo[d][1,2,3]triazol-5-yl)methyl) hexahydropyrrolo[3,4-c]pyrrol-2(1H)-yl)(2-cyclopropyl-6-((tetrahydro-2H-pyran-4-yl)methoxy)pyridin-4-yl) methanone;

((3aS,6aS)-5-((1H-benzo[d][1,2,3]triazol-5-yl)methyl) hexahydropyrrolo[3,4-c]pyrrol-2(1H)-yl)(2-cyclopropyl-6-((tetrahydro-2H-pyran-3-yl)methoxy)pyridin-4-yl) methanone;

((3aR,8aS)-6-(2-cyclopropyl-6-((tetrahydro-2H-pyran-4-yl) methoxy)isonicotinoyl)octahydropyrrolo[3,4-d]azepin-2(1H)-yl)((R)-4,5,6,7-tetrahydro-1H-benzo[d][1,2,3]triazol-5-yl)methanone;

((3aR,8aS)-6-(1H-benzo[d][1,2,3]triazole-5-carbonyl)octahydropyrrolo[3,4-d]azepin-2(1H)-yl)(2-cyclopropyl-6-((tetrahydro-2H-pyran-4-yl)methoxy)pyridin-4-yl)methanone;

((3aS,6aS)-5-(1H-benzo[d][1,2,3]triazole-5-carbonyl)hexahydropyrrolo[3,4-c]pyrrol-2(1H)-yl)(2-(dimethylamino)-6-((tetrahydro-2H-pyran-4-yl)methoxy)pyridin-4-yl)methanone;

6-(((3aS,6aS)-5-(2-cyclopropyl-6-((tetrahydro-2H-pyran-4-yl)methoxy)isonicotinoyl)hexahydropyrrolo[3,4-c]pyrrol-2(1H)-yl)methyl)benzo[d]oxazol-2(3H)-one;

((3aS,6aS)-5-(2-(dimethylamino)-6-((tetrahydro-2H-pyran-4-yl)methoxy)isonicotinoyl)hexahydropyrrolo[3,4-c]pyrrol-2(1H)-yl)((R)-4,5,6,7-tetrahydro-1H-benzo[d][1,2,3]triazol-5-yl)methanone;

((3aR,6aS)-5-(1H-benzo[d][1,2,3]triazole-5-carbonyl)hexahydropyrrolo[3,4-c]pyrrol-2(1H)-yl)(2-cyclopropyl-6-((tetrahydro-2H-pyran-4-yl)methoxy)pyridin-4-yl)methanone;

4-((3aR,6aS)-5-(2-cyclopropyl-6-((tetrahydro-2H-pyran-4-yl)methoxy)isonicotinoyl)octahydropyrrolo[3,4-c]pyrrole-2-carbonyl)benzenesulfonamide;

((3aR,8aS)-6-(3-cyclopropyl-5-((tetrahydro-2H-pyran-4-yl)methoxy)benzoyl)octahydropyrrolo[3,4-d]azepin-2(1H)-yl)((R)-4,5,6,7-tetrahydro-1H-benzo[d][1,2,3]triazol-5-yl)methanone;

((3aS,6aS)-5-(1H-benzo[d][1,2,3]triazole-5-carbonyl)hexahydropyrrolo[3,4-c]pyrrol-2(1H)-yl)(3-cyclopropyl-5-((tetrahydro-2H-pyran-4-yl)methoxy)phenyl)methanone;

6-((3aR,6aR)-5-(3-cyclopropyl-5-((tetrahydro-2H-pyran-4-yl)methoxy)benzoyl)octahydropyrrolo[3,4-c]pyrrole-2-carbonyl)pyridine-3-sulfonamide;

6-((3aS,6aS)-5-(5-cyclopropyl-6-(tetrahydro-2H-pyran-4-yloxy)nicotinoyl)octahydropyrrolo[3,4-c]pyrrole-2-carbonyl)benzo[d]oxazol-2(3H)-one;

6-((3aS,6aS)-5-(2-cyclopropyl-6-((tetrahydro-2H-pyran-4-yl)methoxy)isonicotinoyl)octahydropyrrolo[3,4-c]pyrrole-2-carbonyl)benzo[d]oxazol-2(3H)-one;

6-((3aR,8aS)-6-(2-cyclopropyl-6-((tetrahydro-2H-pyran-4-yl)methoxy)isonicotinoyl)decahydropyrrolo[3,4-d]azepine-2-carbonyl)benzo[d]oxazol-2(3H)-one;

6-(((3aS,6aS)-5-(5-cyclopropyl-6-(tetrahydro-2H-pyran-4-yloxy)nicotinoyl)hexahydropyrrolo[3,4-c]pyrrol-2(1H)-yl)methyl)benzo[d]oxazol-2(3H)-one;

((3aS,6aS)-5-((1H-benzo[d][1,2,3]triazol-5-yl)methyl)hexahydropyrrolo[3,4-c]pyrrol-2(1H)-yl)(5-cyclopropyl-6-(tetrahydro-2H-pyran-4-yloxy)pyridin-3-yl)methanone;

((3aR,6aR)-5-(2-cyclopropyl-6-((tetrahydro-2H-pyran-4-yl)methoxy)isonicotinoyl)hexahydropyrrolo[3,4-c]pyrrol-2(1H)-yl)(6,7-dihydro-1H-[1,2,3]triazolo[4, 5-c]pyridin-5(4H)-yl)methanone;

1-((3aR,6aR)-5-(2-cyclopropyl-6-((tetrahydro-2H-pyran-4-yl)methoxy)isonicotinoyl)octahydropyrrolo[3,4-c]pyrrole-2-carbonyl)piperidine-4-sulfonamide;

((3aR,8aS)-6-(2-cyclopropyl-6-((tetrahydro-2H-pyran-4-yl)methoxy)isonicotinoyl)octahydropyrrolo[3,4-d]azepin-2(1H)-yl)(6,7-dihydro-1H-[1,2,3]triazolo[4,5-c]pyridin-5(4H)-yl)methanone;

((3aR,8aS)-6-(2-cyclopropyl-6-((tetrahydro-2H-pyran-4-yl)methoxy)isonicotinoyl)octahydropyrrolo[3,4-d]azepin-2(1H)-yl)(3-hydroxy-4,5-dihydroisoxazolo[5,4-c]pyridin-6(7H)-yl)methanone;

(3aR,8aS)-N-((1H-1,2,3-triazol-4-yl)methyl)-6-(2-cyclopropyl-6-((tetrahydro-2H-pyran-4-yl)methoxy)isonicotinoyl)octahydropyrrolo[3,4-d]azepine-2(1H)-carboxamide;

(3aR,8aS)-6-(2-cyclopropyl-6-((tetrahydro-2H-pyran-4-yl)methoxy)isonicotinoyl)-N-((3-hydroxyisoxazol-5-yl)methyl)octahydropyrrolo[3,4-d]azepine-2(1H)-carboxamide;

1H-triazol-4-ylmethyl (3aS,8aR)-6-[2-cyclopropyl-6-(oxan-4-ylmethoxy)pyridine-4-carbonyl]-1,3,3a,4,5,7,8,8a-octahydropyrrolo[3,4-d]azepine-2-carboxylate;

5-((3aR,6aR)-5-(2-cyclopropyl-6-((tetrahydro-2H-pyran-4-yl)methoxy)isonicotinoyl)octahydropyrrolo[3,4-c]pyrrole-2-carbonyl)pyridine-2-sulfonamide;

((3aR,8aS)-6-(2-cyclopropyl-6-((tetrahydro-2H-pyran-4-yl)methoxy)isonicotinoyl)octahydropyrrolo[3,4-d]azepin-2(1H)-yl)(4, 5,6,7-tetrahydro-1H-benzo[d][1,2,3]triazol-5-yl)methanone;

((3aS,6aS)-5-(1H-benzo[d][1,2,3]triazole-5-carbonyl)hexahydropyrrolo[3,4-c]pyrrol-2(1H)-yl)(2-chloro-6-((tetrahydro-2H-pyran-4-yl)methoxy)pyridin-4-yl)methanone;

((3aR,8aS)-6-(2-cyclopropyl-6-((tetrahydro-2H-pyran-4-yl)methoxy)isonicotinoyl)octahydropyrrolo[3,4-d]azepin-2(1H)-yl)((S)-4,5,6,7-tetrahydro-1H-benzo[d][1,2,3]triazol-5-yl)methanone;

and pharmaceutically acceptable salts thereof.

Also particular examples of compounds of formula (I) as described herein are selected from 5-((3aS,6aS)-5-(5-cyclopropyl-6-(tetrahydro-2H-pyran-4-yloxy)nicotinoyl)octahydropyrrolo[3,4-c]pyrrole-2-carbonyl)pyridine-2-sulfonamide;

6-((3aR,6aR)-5-(5-cyclopropyl-6-(tetrahydro-2H-pyran-4-yloxy)nicotinoyl)octahydropyrrolo[3,4-c]pyrrole-2-carbonyl)pyridine-3-sulfonamide;

4-((3aS,6aS)-5-(5-cyclopropyl-6-(tetrahydro-2H-pyran-4-yloxy)nicotinoyl)octahydropyrrolo[3,4-c]pyrrole-2-carbonyl)benzenesulfonamide;

4-((3aR,6aS)-5-(5-cyclopropyl-6-(tetrahydro-2H-pyran-4-yloxy)nicotinoyl)octahydropyrrolo[3,4-c]pyrrole-2-carbonyl)benzenesulfonamide;

((3aS,6aS)-5-(1H-benzo[d][1,2,3]triazole-5-carbonyl)hexahydropyrrolo[3,4-c]pyrrol-2(1H)-yl)(2-cyclopropyl-6-((tetrahydro-2H-pyran-4-yl)methoxy)pyridin-4-yl)methanone;

((3aS,6aS)-5-(3-cyclopropyl-4-(tetrahydrofuran-3-yl oxy)benzoyl)hexahydropyrrolo[3,4-c]pyrrol-2(1H)-yl)((R)-4,5,6,7-tetrahydro-1H-benzo[d][1,2,3]triazol-5-yl)methanone;

((3aR,6aR)-5-(1H-benzo[d][1,2,3]triazole-5-carbonyl)hexahydropyrrolo[3,4-c]pyrrol-2(1H)-yl)(3-cyclopropyl-4-(tetrahydrofuran-3-yloxy)phenyl)methanone;

((3aS,6aS)-5-(1H-benzo[d][1,2,3]triazole-5-carbonyl)hexahydropyrrolo[3,4-c]pyrrol-2(1H)-yl)(5-cyclopropyl-6-(tetrahydro-2H-pyran-4-ylamino)pyridin-3-yl)methanone;

((3aS,6aS)-5-(1H-benzo[d][1,2,3]triazole-5-carbonyl)hexahydropyrrolo[3,4-c]pyrrol-2(1H)-yl)(5-cyclopropyl-6-(tetrahydrofuran-3-yloxy)pyridin-3-yl)methanone;

((3aS,6aS)-5-(1H-benzo[d][1,2,3]triazole-5-carbonyl)hexahydropyrrolo[3,4-c]pyrrol-2(1H)-yl)(5-cyclopropyl-6-(tetrahydro-2H-pyran-3-yloxy)pyridin-3-yl)methanone;

((3aS,6aS)-5-(1H-benzo[d][1,2,3]triazole-5-carbonyl)hexahydropyrrolo[3,4-c]pyrrol-2(1H)-yl)(5-cyclopropyl-6-(tetrahydro-2H-pyran-4-yloxy)pyridin-3-yl)methanone;

((3aS,6aS)-5-(1H-benzo[d][1,2,3]triazole-5-carbonyl)hexahydropyrrolo[3,4-c]pyrrol-2(1H)-yl)(6-(oxetan-3-yloxy)-5-(trifluoromethyl)pyridin-3-yl)methanone;

((3aS,6aS)-5-(5-cyclopropyl-6-(tetrahydro-2H-pyran-4-yloxy)nicotinoyl)hexahydropyrrolo[3,4-c]pyrrol-2(1H)-yl)((R)-4,5,6,7-tetrahydro-1H-benzo[d][1,2,3]triazol-5-yl)methanone;

and pharmaceutically acceptable salts thereof.

Further particular examples of compounds of formula (I) as described herein are selected from 5-((3aS,6aS)-5-(5-cyclopropyl-6-(tetrahydro-2H-pyran-4-yloxy)nicotinoyl)octahydropyrrolo[3,4-c]pyrrole-2-carbonyl)pyridine-2-sulfonamide;

((3aS,6aS)-5-(1H-benzo[d][1,2,3]triazole-5-carbonyl)hexahydropyrrolo[3,4-c]pyrrol-2(1H)-yl)(2-cyclopropyl-6-((tetrahydro-2H-pyran-4-yl)methoxy)pyridin-4-yl)methanone;

((3aS,6aS)-5-(5-cyclopropyl-6-(tetrahydro-2H-pyran-4-yloxy)nicotinoyl)hexahydropyrrolo[3,4-c]pyrrol-2(1H)-yl)((R)-4,5,6,7-tetrahydro-1H-benzo[d][1,2,3]triazol-5-yl)methanone;

2-chloro-4-((3aR,6aR)-5-(2-cyclopropyl-6-((tetrahydro-2H-pyran-4-yl)methoxy)isonicotinoyl)octahydropyrrolo[3,4-c]pyrrole-2-carbonyl)benzenesulfonamide;

4-((3aR,6aR)-5-(2-cyclopropyl-6-((tetrahydro-2H-pyran-4-yl)methoxy)isonicotinoyl)octahydropyrrolo[3,4-c]pyrrole-2-carbonyl)-3-fluorobenzenesulfonamide;

((3aR,8aS)-2-(1H-benzo[d][1,2,3]triazole-5-carbonyl)octahydropyrrolo[3,4-d]azepin-6(7H)-yl)(2-cyclopropyl-6-((tetrahydro-2H-pyran-4-yl)methoxy)pyridin-4-yl)methanone;

5-((3aR,8aS)-6-(2-cyclopropyl-6-((tetrahydro-2H-pyran-4-yl)methoxy)isonicotinoyl)decahydropyrrolo[3,4-d]azepine-2-carbonyl)-1H-benzo[d]imidazol-2(3H)-one;

6-((3aR,8aS)-6-(2-cyclopropyl-6-((tetrahydro-2H-pyran-4-yl)methoxy)isonicotinoyl)decahydropyrrolo[3,4-d]azepine-2-carbonyl)-1-methyl-1H-benzo[d]imidazol-2(3H)-one;

6-((3aR,6aR)-5-(2-cyclopropyl-6-((tetrahydro-2H-pyran-4-yl)methoxy)isonicotinoyl)octahydropyrrolo[3,4-c]pyrrole-2-carbonyl)pyridine-3-sulfonamide;

((3aR,8aS)-6-(2-cyclopropyl-6-((tetrahydro-2H-pyran-4-yl)methoxy)isonicotinoyl)octahydropyrrolo[3,4-d]azepin-2(1H)-yl)((R)-4,5,6,7-tetrahydro-1H-benzo[d][1,2,3]triazol-5-yl)methanone;

((3aR,8aS)-6-(1H-benzo[d][1,2,3]triazole-5-carbonyl)octahydropyrrolo[3,4-d]azepin-2(1H)-yl)(2-cyclopropyl-6-((tetrahydro-2H-pyran-4-yl)methoxy)pyridin-4-yl)methanone;

6-((3aR,8aS)-6-(2-cyclopropyl-6-((tetrahydro-2H-pyran-4-yl)methoxy)isonicotinoyl)decahydropyrrolo[3,4-d]azepine-2-carbonyl)benzo[d]oxazol-2(3H)-one;

((3aR,8aS)-6-(2-cyclopropyl-6-((tetrahydro-2H-pyran-4-yl)methoxy)isonicotinoyl)octahydropyrrolo[3,4-d]azepin-2(1H)-yl)(6,7-dihydro-1H-[1,2,3]triazolo[4,5-c]pyridin-5(4H)-yl)methanone;

((3aR,8aS)-6-(2-cyclopropyl-6-((tetrahydro-2H-pyran-4-yl)methoxy)isonicotinoyl)octahydropyrrolo[3,4-d]azepin-2(1H)-yl)(3-hydroxy-4,5-dihydroisoxazolo[5,4-c]pyridin-6(7H)-yl)methanone;

and pharmaceutically acceptable salts thereof.

Also further particular examples of compounds of formula (I) as described herein are selected from 5-((3aS,6aS)-5-(5-cyclopropyl-6-(tetrahydro-2H-pyran-4-yloxy)nicotinoyl)octahydropyrrolo[3,4-c]pyrrole-2-carbonyl)pyridine-2-sulfonamide;

((3aS,6aS)-5-(1H-benzo[d][1,2,3]triazole-5-carbonyl)hexahydropyrrolo[3,4-c]pyrrol-2(1H)-yl)(2-cyclopropyl-6-((tetrahydro-2H-pyran-4-yl)methoxy)pyridin-4-yl)methanone;

((3aS,6aS)-5-(5-cyclopropyl-6-(tetrahydro-2H-pyran-4-yloxy)nicotinoyl)hexahydropyrrolo[3,4-c]pyrrol-2(1H)-yl)((R)-4,5,6,7-tetrahydro-1H-benzo[d][1,2,3]triazol-5-yl)methanone;

and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reactions and purifications of the resulting products are known to those persons skilled in the art. In case a mixture of enantiomers or diastereoisomers is produced during a reaction, these enantiomers or diastereoisomers can be separated by methods described herein or known to the man skilled in the art such as e.g. (chiral) chromatography or crystallization. The substituents and indices used in the following description of the processes have the significance given herein.

The present invention provides novel compounds of formula (I)

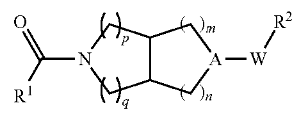

(I)

Compounds of general formula (I) can be synthesised from amine precursor 1 and appropriate reagents, using methods well known in the art.

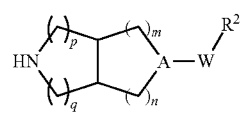

1

For instance, amine 1 is reacted with a suitable carboxylic acid of formula $R^1$—COOH (2) leading to a compound of formula (I). The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Amine 1 can also be reacted with suitable acylating reagents such as acyl chlorides of formula $R^1$—COCl (3) to lead to compounds of formula (I). The reaction is performed in a solvent such as dichloromethane, tetrahydrofuran, or N,N-dimethylformamide, in the presence of a base such as triethylamine or 4-methylmorpholine, at temperatures between 0° C. and 80° C.

Carboxylic acids (2) and acyl halides (3) are commercially available or can be prepared as described herein or in the literature.

Amines of general formula 1 are synthesised from suitably protected precursors 4.

4

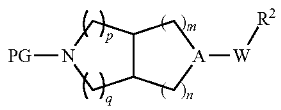

Suitable protective groups (PG) are tert-butoxycarbonyl or benzyloxycarbonyl. The deprotection of intermediates 4 can be performed using methods and reagents known in the art.

For instance, in the case where PG is benzyloxycarbonyl, the deprotection may be performed by hydrogenation at pressures between 1 bar and 100 bar, in the presence of a suitable catalyst such as palladium on activated charcoal, at temperatures between 20° C. and 150° C. in solvents such as methanol or ethanol.

Alternatively, in the case where PG is tert-butoxycarbonyl, the deprotection may be performed in the presence of a suitable acid, e.g., hydrochloric acid or trifluoroacetic acid, in a solvent such as water, 2-propanol, dichloromethane, or 1,4-dioxane at temperatures between 0° C. and 30° C.

Intermediates 4, wherein A is N are represented by general structure 4A.

4A

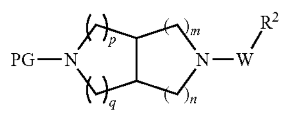

PG is a suitable protective group, e.g., tert-butoxycarbonyl or benzyloxycarbonyl.

Intermediates 4A can be produced from amine precursors of general formula 5 by reaction with appropriate reagents, using methods known in the art.

5

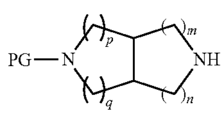

For instance, 5 is reacted with alkylating agents of general formula X—$CR^6R^7$—$R^2$ (6) where X is a leaving group such as Cl, Br, I, or $OSO_2CH_3$, leading to 4A, wherein W is —$CR^6R^7$—. This reaction is performed in a solvent such as tetrahydrofuran or N,N-dimethylformamide, in the presence of a base, e.g. triethylamine or potassium carbonate, at temperatures between 0° C. and 100° C.

Alternatively, for compounds of formula 4A, wherein W is —$CR^6R^7$—, $R^6$ is hydrogen, alkyl or cycloalkyl, and $R^7$ is H, amine 5 is reacted with aldehydes or ketones of general formula $R^6$—C(O)—$R^2$ (7) in a reductive amination reaction, leading to 4A. This reaction is performed in the presence of a suitable reducing agent, e.g., sodium borohydride or sodium triacetoxyborohydride, in a solvent such as methanol, acetic acid, tetrahydrofuran, 1,2-dichloroethane or mixtures thereof, at temperatures between 0° C. and 50° C.

Alternatively, amine 5 is reacted with a suitable carboxylic acid of formula $R^2$—COOH (8), leading to compounds of formula 4A, wherein W is —C(O)—. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Alternatively, amine 5 is reacted with a suitable sulfonyl chloride of formula $R^2$—$SO_2Cl$ (9), leading to compounds of formula 4A, wherein W is —$S(O_2)$—. The reaction is performed in a suitable solvent such as dichloromethane, tetrahydrofuran, N,N-dimethylformamide, acetonitrile, acetone, water, or mixtures thereof, in the presence of a base, e.g. triethylamine, diisopropylethylamine, pyridine, potassium hydrogencarbonate, potassium carbonate, at temperatures between 0° C. and the boiling point of the solvent or solvent mixture.

Alternatively, amine 5 is reacted with a suitable N-(chlorocarbonyl)amine of formula $R^2$—N($R^{10}$)—C(O)—Cl (10A) leading to compounds of formula 4A, wherein W is —C(O)—$NR^{10}$—, or with an isocyanate of formula $R^2$—NCO (11), leading to compounds of formula 4A, wherein W is —C(O)—$NR^{10}$— and $R^{10}$ is H.

Alternatively, amine 5 is reacted with phosgene or phosgene equivalent (diphosgene, triphosgene) in the presence of a base (e.g., pyridine, triethylamine) in a solvent such as dichloromethane or tetrahydrofuran, to provide the corresponding N-(chlorocarbonyl)amine of formula 12, which is then reacted with amine of formula HN($R^{10}$)$R^2$ (13), in the presence of a base such as triethylamine or diisopropylethylamine, in a solvent such as dichloromethane, tetrahydrofuran, or N,N-dimethylformamide, leading to compounds of formula 4A, wherein W is —C(O)—$NR^{10}$—.

12

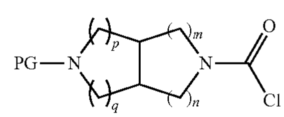

Alternatively, amine 5 is reacted with phosgene or a phosgene equivalent (diphosgene, triphosgene) in the presence of a base (e.g., pyridine, triethylamine), in a solvent such as dichloromethane or tetrahydrofuran, to the corresponding N-(chlorocarbonyl)amine of formula 12, which is then reacted with amines of formula H—O, H—P, H-Q, H—R, H-T, H—U, H—V, H—X, H-AA, H-AI or H-AO, in the presence of a base such as triethylamine or diisopropylethylamine, in a solvent such as dichloromethane, tetrahydrofuran, or N,N-dimethylformamide, leading to compounds of formula 4A, wherein W is —C(O)— and $R^2$ is O, P, Q, R, T, U, V, X, AA, AI or AO.

Alternatively, amine 5 is reacted with a suitable chloroformate of formula $R^2$—O—C(O)—Cl (10B) or with an imidazole-1-carboxylate ester (10C), leading to compounds of formula 4A, wherein W is —C(O)—O—. The reaction is performed in a suitable solvent, e.g., acetonitrile or N,N-dimethylformamide, optionally in the presence of a base, e.g., diisopropylethylamine or triethylamine, at temperatures between 0° C. and 100° C.

10C

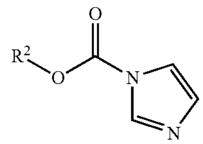

Chloroformates 10B are commercially available or can be prepared from the corresponding alcohols of formula $R^2$—OH, by reaction with phosgene or a phosgene equivalent (e.g., diphosgene, triphosgene) as described herein or in the literature.

Imidazole-1-carboxylate esters 10C can be prepared from the corresponding alcohols of formula $R^2$—OH, by reaction with 1,1'-carbonyldiimidazole as described herein or in the literature.

N-(Chlorocarbonyl)amines 12 are synthesised from the corresponding amines 13 by reaction with phosgene or a phosgene equivalent (diphosgene, triphosgene) as described in the literature.

Isocyanates 11 are commercially available or can be prepared from the corresponding amines of formula $R^2$—$NH_2$, by reaction with phosgene or a phosgene equivalent (e.g., diphosgene, triphosgene, 1,1'-carbonyldiimidazole) as described in the literature.

N-(Chlorocarbonyl)amines 10A are commercially available or can be prepared from the corresponding amines of formula $HN(R^{10})R^2$ (13), by reaction with phosgene or a phosgene equivalent (e.g., diphosgene, triphosgene, 1,1'-carbonyldiimidazole) as described herein or in the literature.

Amines 5, alkylating agents 6, aldehydes/ketones 7, carboxylic acids 8, sulfonyl chlorides 9, isocyanates 11, and amines 13 are commercially available or can be synthesised as described herein or in the literature.

Carbamates 4 wherein A is CH, and W is —C(O)—N($R^{10}$), are represented by general formula 4B, wherein $R^{14}$ is $N(R^{10})R^2$. Carbamates 4 wherein A is CH, W is —C(O)— and $R^2$ is O, P, Q, R, T, U, V, X, AA, AI or AO are also represented by general formula 4B, wherein $R^{14}$ is O, P, Q, R, T, U, V, X, AA, AI or AO.

4B

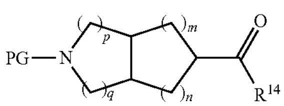

Amide 4B is produced from carboxylic acid 14 by coupling reaction with an amine of formula $HN(R^{10})R^2$ (13), H—O, H—P, H-Q, H—R, H-T, H—U, H—V, H—X, H-AA, H-AI or H-AO.

14

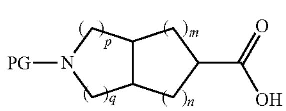

The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Carboxylic acids 14 are commercially available or can be produced as described in the literature.

Compounds of formula (I), wherein A is N can be produced from amine precursors of general formula 15 by reaction with appropriate reagents, using methods known in the art.

15

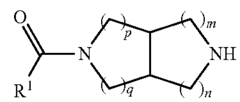

For instance, an amine of formula 15 is reacted with alkylating agents of general formula X—$CR^6R^7$—$R^2$ (6) where X is a leaving group such as Cl, Br, I, or $OSO_2CH_3$, leading to compounds of formula (I), wherein A is N and W is —$CR^6R^7$—. This reaction is performed in a solvent such as tetrahydrofuran or N,N-dimethylformamide, in the presence of a base, e.g., triethylamine or potassium carbonate, at temperatures between 0° C. and 100° C.

Alternatively, an amine of formula 15 is reacted with aldehydes or ketones of general formula $R^6$—C(O)—$R^2$ (16) in a reductive amination reaction, leading to compounds of formula (I) wherein A is N, W is —$CR^6R^7$—, $R^6$ is hydrogen, alkyl or cycloalkyl, and $R^7$ is H. This reaction is performed in the presence of a suitable reducing agent, e.g. sodium borohydride or sodium triacetoxyborohydride, in a solvent such as methanol, acetic acid, tetrahydrofuran, 1,2-dichloroethane or mixtures thereof, at temperatures between 0° C. and 50° C.

Alternatively, amine 15 is reacted with a suitable carboxylic acid of formula $R^2$—COOH (8), leading to compounds of formula (I) wherein A is N and W is —C(O)—. The reaction is performed in the presence of a coupling agent such as 1,1'-carbonyldiimidazole, N,N'-di cyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tri s-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyri dine.

Alternatively, amine 15 is reacted with a suitable sulfonyl chloride of formula $R^2$—$SO_2Cl$ (9), leading to (I) wherein A is N and W is —$S(O_2)$—. The reaction is performed in a suitable solvent such as dichloromethane, tetrahydrofuran, N,N-dimethylformamide, acetonitrile, acetone, water, or mixtures thereof, in the presence of a base, e.g. triethylamine, diisopropylethylamine, pyridine, potassium hydrogencarbonate, potassium carbonate, at temperatures between 0° C. and the boiling point of the solvent or solvent mixture.

Alternatively, amine 15 is reacted with a suitable N-(chlorocarbonyl)amine of formula $R^2$—N($R^{10}$)—C(O)—Cl (10A) leading to compounds of formula (I), wherein W is —C(O)—$NR^{10}$—, or with an isocyanate of formula $R^2$—NCO (11), leading to compounds of formula (I), wherein W is —C(O)—$NR^{10}$— and $R^{10}$ is H. The reaction is performed in a suitable solvent, e.g., acetonitrile or N,N-dimethylformamide, optionally in the presence of a base, e.g., diisopropylethylamine or triethylamine, at temperatures between 0° C. and 100° C.

Alternatively, amine 15 is reacted with a suitable chloroformate of formula $R^2$—O—C(O)—Cl (10B) or with an imidazole-1-carboxylate ester (10C), leading to compounds of formula (I), wherein W is —C(O)—O—. The reaction is performed in a suitable solvent, e.g., acetonitrile or N,N-dimethylformamide, optionally in the presence of a base, e.g., diisopropylethylamine or triethylamine, at temperatures between 0° C. and 100° C.

Alternatively, amine 15 is reacted with phosgene or phosgene equivalent (diphosgene, triphosgene) in the presence of a base (e.g., pyridine, triethylamine) in a solvent such as dichloromethane or tetrahydrofuran, to provide the corresponding N-(chlorocarbonyl)amine of formula 16, which is then reacted with amine of formula HN($R^{10}$)$R^2$ (13), in the presence of a base such as triethylamine or diisopropylethylamine, in a solvent such as dichloromethane, tetrahydrofuran, or N,N-dimethylformamide, leading to compounds of formula (I), wherein W is —C(O)—$NR^{10}$—.

16

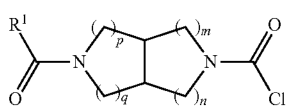

Alternatively, amine 15 is reacted with phosgene or a phosgene equivalent (diphosgene, triphosgene) in the presence of a base (e.g., pyridine, triethylamine), in a solvent such as dichloromethane or tetrahydrofuran, to the corresponding N-(chlorocarbonyl)amine of formula 16, which is then reacted with amines of formula H—O, H—P, H-Q, H—R, H-T, H—U, H—V, H—X, H-AA, H-AI or H-AO, in the presence of a base such as triethylamine or diisopropylethylamine, in a solvent such as dichloromethane, tetrahydrofuran, or N,N-dimethylformamide, leading to compounds of formula (I), wherein W is —C(O)— and $R^2$ is O, P, Q, R, T, U, V, X, AA, AI or AO.

Amines 15 can be synthesised from their tert-butyl carbamate derivatives of formula 17 by carbamate deprotection. The deprotection may be performed in the presence of a suitable acid, e.g., hydrochloric acid or trifluoroacetic acid, in a solvent such as water, 2-propanol, dichloromethane, or 1,4-dioxane, at temperatures between 0° C. and 30° C.

17

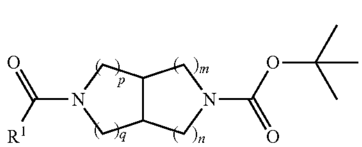

tert-Butyl carbamates 17 can be synthesised from amine precursors of formula 18 and appropriate reagents, using methods well known in the art.

18

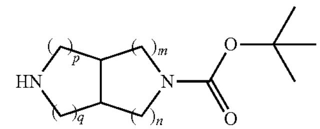

For instance, amine 18 is reacted with a suitable carboxylic acid of formula $R^1$—COOH (2) leading to compounds of formula 17. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Amine 18 can also be reacted with suitable acylating reagents, such as acyl chlorides of formula $R^1$—COCl (3) to provide compounds of formula 17. The reaction is performed in a solvent such as dichloromethane, tetrahydrofuran, or N,N-dimethylformamide, in the presence of a base such as triethylamine or 4-methylmorpholine, at temperatures between 0° C. and 80° C.

Amines of formula 18 are commercially available or can be produced as described herein or in the literature.

Compounds of formula (I), wherein A is CH and W is —C(O)—$NR^{10}$— can be produced from carboxylic acid precursors of general formula 19 by reaction with appropriate amine reagents of general formula HN($R^{10}$)$R^2$. Likewise, compounds of formula (1), wherein A is CH, W is C(O), and $R^2$ is O, P, Q, R, T, U, V, X, AA, AI or AO, can be produced from carboxylic acid precursors of general formula 19 by reaction with appropriate amine reagents of general formula H—O, H—P, H-Q, H—R, H-T, H—U, H—V, H—X, H-AA, H-AI or H-AO, using methods known in the art.

19

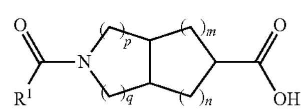

For instance, this reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Compounds of formula (I), wherein A is CH and W is —C(O)—O— can be produced from carboxylic acid precursors of general formula 19 by reaction with appropriate alcohols of general formula $R^2$—OH, using methods known in the art.

For instance, this reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Alternatively, the reaction is performed in two steps wherein carboxylic acid 19 is first converted to acid chloride 19A, using methods and reagents known in the art, e.g., thionyl chloride or oxalyl chloride. Acid chloride 19A is then reacted with alcohol $R^2$—OH in a suitable solvent, e.g., dichloromethane or acetonitrile, optionally in the presence of a catalyst, e.g., pyridine or 4-(dimethylamino)pyridine, at temperatures between −40° C. and +100° C.

19A

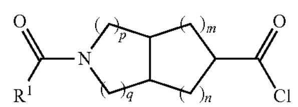

Carboxylic acids 19 can be produced from the corresponding ester precursors 20, wherein $R^a$ is lower alkyl, e.g. methyl or ethyl, using methods and reagents known in the art. For instance, the reaction is performed in the presence of a base, e.g., potassium hydroxide, sodium hydroxide, or lithium hydroxide, in solvents such as water, methanol, ethanol, tetrahydrofuran, or mixtures thereof, at temperatures between 20° C. and 100° C.

20

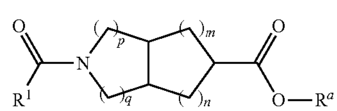

Compounds of formula 20 can be synthesised from amine precursors of formula 21 and appropriate reagents, using methods well known in the art.

21

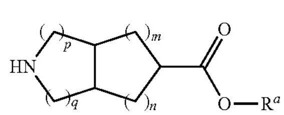

For instance, amine 21 is reacted with a suitable carboxylic acid of formula $R^1$—COOH (2) leading to compounds of formula 20. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Amine 21 can also be reacted with suitable acylating reagents, such as acyl chlorides of formula $R^1$—COCl (3) to lead to compounds of formula 20. The reaction is performed in a solvent such as dichloromethane, tetrahydrofuran, or N,N-dimethylformamide, in the presence of a base such as triethylamine or 4-methylmorpholine, at temperatures between 0° C. and 80° C.

Amines of general formula 21 are synthesised from suitably protected precursors 22.

22

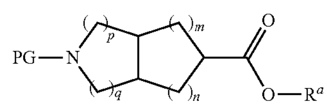

Suitable protective groups (PG) are tert-butoxycarbonyl or benzyloxycarbonyl. The deprotection of intermediates 22 can be performed using methods and reagents known in the art.

For instance, in the case where PG is benzyloxycarbonyl, the deprotection may be performed by hydrogenation at pressures between 1 bar and 100 bar, in the presence of a suitable catalyst such as palladium on activated charcoal, at temperatures between 20° C. and 150° C., in solvents such as methanol or ethanol.

Alternatively, in the case where PG is tert-butoxycarbonyl, the deprotection may be performed in the presence of a suitable acid, e.g., hydrochloric acid or trifluoroacetic acid, in a solvent such as water, 2-propanol, dichloromethane, or 1,4-dioxane, at temperatures between 0° C. and 30° C.

Esters 22, wherein $R^a$ is methyl or ethyl, are produced from carboxylic acids 14, using methods and reagents known in the art. For instance, 14 alkylated with methyl iodide or ethyl bromide, in the presence of a base, e.g., potassium carbonate, in a solvent such as N,N-dimethylformamide, at −20° C. and +30° C., leading to the methyl or ethyl ester 22, respectively.

tert-Butyl carbamates 17 wherein $R^1$ is substituted $R^3$—C(3)-phenyl or substituted $R^3$—C(2)-pyridin-4-yl and $R^3$ is O—$R^{15}$ are represented by general structure 17A.

17A

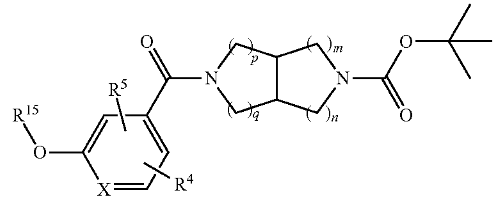

$R^{15}$ is heterocycloalkyl or heterocyclyl, X is CH or N, $R^4$, $R^5$, m, n, p, q are as described above.

Compounds of formula 17A can be also produced from phenol or pyridinol 23, using methods and reagents well known in the art.

23

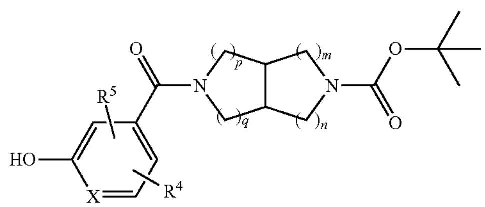

For instance, compound 23 is alkylated with an appropriate alkylating agent of formula $R^{15}$-X, wherein X is a leaving group, e.g., Br or I, leading to compounds 17A. The reaction is performed in the presence of a base, e.g., potassium carbonate, in a solvent such as acetone, acetonitrile, or N,N-dimethylformamide, at temperatures between 20° C. and the boiling point of the solvent.

Alkylating agents $R^{15}$—X are commercially available or can be prepared as described herein or in the literature.

Compound of formula 23 can be produced from amine 18 and carboxylic acid 24, using methods and reagents well known in the art.

24

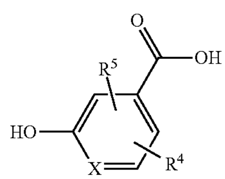

For instance, amine 18 is reacted with carboxylic acid 24 leading to compounds of formula 23. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Carboxylic acids 24 are commercially available or can be prepared as described herein or in the literature.

tert-Butyl carbamates 17 wherein $R^1$ is substituted $R^3$—C(6)-pyridin-3-yl and $R^3$ is O—$R^{15}$ are represented by general structure 17B.

17B

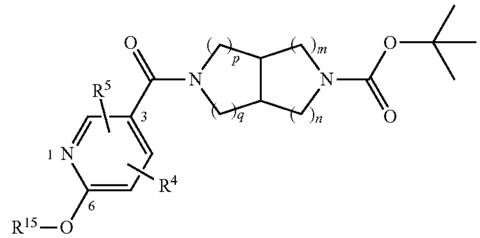

$R^{15}$ is heterocycloalkyl or heterocyclyl, $R^4$, $R^5$, m, n, p, q are as described above.

Compounds of formula 17B can also be produced from halopyridine 25, using methods and reagents well known in the art.

25

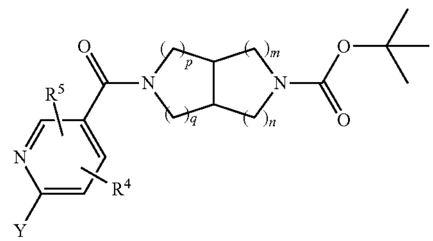

Y is a halogen, e.g., F, Cl, Br, or I, $R^4$, $R^5$, m, n, p, q are as described above.

For instance, compound 25 is reacted with an appropriate alcohol of formula $R^{15}$—OH, leading to compounds 17B. The reaction is performed in the presence of a base, e.g., potassium hydroxide or potassium carbonate, in a solvent such as or N,N-dimethylformamide or dimethyl sulfoxide, at temperatures between −70° C. and +150° C.

Alcohols $R^{15}$—OH are commercially available or can be prepared as described herein or in the literature.

Compound of formula 25 can be produced from amine 18 and carboxylic acid 26, using methods and reagents well known in the art.

26

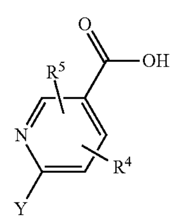

For instance, amine 18 is reacted with carboxylic acid 26 leading to compounds of formula 25. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Carboxylic acids 26 are commercially available or can be prepared as described herein or in the literature.

Esters 20 wherein $R^1$ is substituted $R^3$—C(3)-phenyl or substituted $R^3$—C(2)-pyridin-4-yl and $R^3$ is O—$R^{15}$ are represented by general structure 20A.

20A

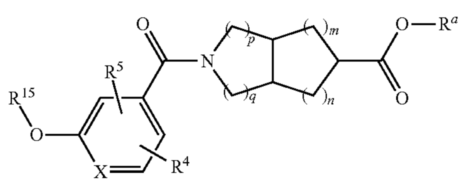

$R^{15}$ is heterocycloalkyl or heterocyclyl, X is CH or N, $R^a$ is lower alkyl, e.g., methyl or ethyl, $R^4$, $R^5$, m, n, p, q are as described above.

Compounds of formula 20A can also be produced from phenol or pyridinol 27, using methods and reagents well known in the art.

27

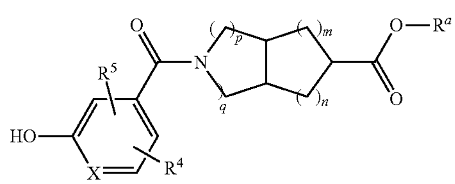

For instance, compound 27 is alkylated with an appropriate alkylating agent of formula $R^{15}$—X, wherein X is a leaving group, e.g., Br or I, leading to compounds 20A. The reaction is performed in the presence of a base, e.g., potassium carbonate, in a solvent such as acetone, acetonitrile, or N,N-dimethylformamide, at temperatures between 20° C. and the boiling point of the solvent.

Compound of formula 27 can be produced from amine 18, using methods and reagents well known in the art. For instance, amine 18 is reacted with carboxylic acid 24 leading to compounds of formula 27. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluorophosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Esters 20 wherein $R^1$ is $R^3$—C(6)-substituted pyridin-3-yl and $R^3$ is O—$R^{15}$ are represented by general structure 20B.

20B

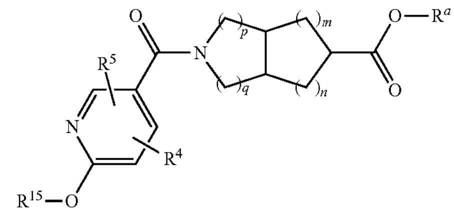

$R^{15}$ is heterocycloalkyl or heterocyclyl, $R^a$ is lower alkyl, e.g., methyl or ethyl, $R^4$, $R^5$, m, n, p, q are as described above.

Compounds of formula 20B can also be produced from halopyridine 28, using methods and reagents well known in the art.

28

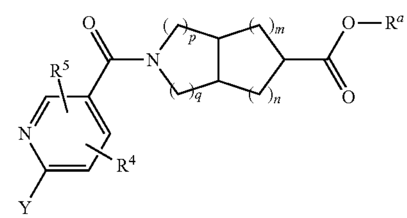

Y is a halogen, e.g., F, Cl, Br, or I, $R^a$ is lower alkyl, e.g., methyl or ethyl, $R^4$, $R^5$, m, n, p, q are as described above.

For instance, compound 28 is reacted with an appropriate alcohol of formula $R^{15}$—OH, leading to compounds 20B. The reaction is performed in the presence of a base, e.g., potassium hydroxide or potassium carbonate, in a solvent such as or N,N-dimethylformamide or dimethyl sulfoxide, at temperatures between −70° C. and +150° C.

Compound of formula 28 can be produced from amine 18, using methods and reagents well known in the art. For instance, amine 18 is reacted with carboxylic acid 26 leading to compounds of formula 28. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluorophosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Also an embodiment of the present invention is a process to prepare a compound of formula (I) as defined above comprising the reaction of a compound of formula (II) in the presence of a compound of formula (III);

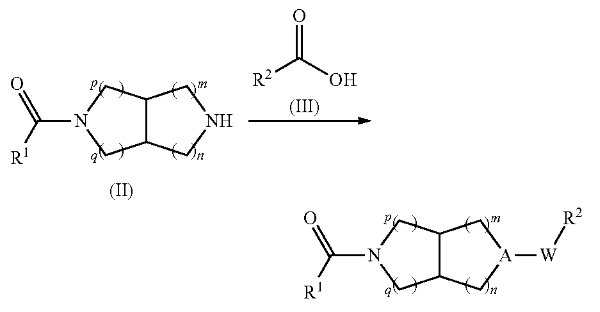

(II)

(I)

wherein $R^1$, $R^2$, m, n, p and q are as defined above, A is —N— and W is —C(O)—.

In particular, in the presence of a coupling agent such as 1,1'-carbonyldiimidazole, N,N'-dicyclohexylcarbodiimide, 1-(3-dimethylaminopropyl)-3-ethyl-carbodiimide hydrochloride, 0-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, particularly O-(7-azabenzotriazol-1-yl)-N,N,N',N',N'-tetramethyluronium hexafluoro-phosphate, in an aprotic solvent such as dichloromethane, tetrahydrofuran, N,N-dimethylformamide, N-methylpyrrolidinone and mixtures thereof, particularly N,N-dimethylformamide, in the presence or absence of a base such as triethylamine, diisopropylethylamine, 4-methylmorpholine and/or 4-(dimethylamino)pyri dine, particularly in the presence of 4-methylmorpholine and at a temperature comprised between −78° C. and reflux, particularly between −10° C. and room temperature.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

An object of the invention is the use of a compound according to formula (I) as described herein for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection, more particularly glaucoma or idiopathic pulmonary formulation Renal conditions include, but are not limited to, acute kidney injury and chronic renal disease with and without proteinuria including end-stage renal disease (ESRD). In more detail, this includes decreased creatinine clearance and decreased glomerular filtration rate, micro-albuminuria, albuminuria and proteinuria, glomerulosclerosis with expansion of reticulated mesangial matrix with or without significant hypercellularity (particularly diabetic nephropathy and amyloidosis), focal thrombosis of glomerular capillaries (particularly thrombotic microangiopathies), global fibrinoid necrosis, ischemic lesions, malignant nephrosclerosis (such as ischemic retraction, reduced renal blood flow and renal arteriopathy), swelling and proliferation of intracapillary (endothelial and mesangial) and/or extracapillary cells (crescents) like in glomerular nephritis entities, focal segmental glomerular sclerosis, IgA nephropathy, vasculitides/systemic diseases as well as acute and chronic kidney transplant rejection.

Liver conditions include, but are not limited to, liver cirrhosis, hepatic congestion, cholestatic liver disease including pruritus, nonalcoholic steatohepatitis and acute and chronic liver transplant rejection.

Inflammatory conditions include, but are not limited to, arthritis, osteoarthritis, multiple sclerosis, systemic lupus erythematodes, inflammatory bowel disease, abnormal evacuation disorder and the like as well as inflammatory airways diseases such as idiopathic pulmonary fibrosis (IPF), chronic obstructive pulmonary disease (COPD) or chronic asthma bronchiale.

Further conditions of the respiratory system include, but are not limited to, other diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, silicosis, asbestos induced pulmonary fibrosis or acute respiratory distress syndrome (ARDS).

Conditions of the nervous system include, but are not limited to, neuropathic pain, schizophrenia, neuro-inflammation (e.g. astrogliosis), peripheral and/or autonomic (diabetic) neuropathies and the like.

Vascular conditions include, but are not limited to, atherosclerosis, thrombotic vascular disease as well as thrombotic microangiopathies, proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction and the like.

Cardiovascular conditions include, but are not limited to, acute coronary syndrome, coronary heart disease, myocardial infarction, arterial and pulmonary hypertension, cardiac arrhythmia such as atrial fibrillation, stroke and other vascular damage.

Fibrotic diseases include, but are not limited to myocardial and vascular fibrosis, renal fibrosis, liver fibrosis, pulmonary fibrosis, skin fibrosis, scleroderma and encapsulating peritonitis.

In a particular embodiment, the compounds of formula (I) or their pharmaceutically acceptable salts and esters can be used for the treatment or prophylaxis of organ or skin fibrosis.

In another embodiment, the fibrotic disease is renal tubulo-interstitial fibrosis or glomerulosclerosis.

In another embodiment, the fibrotic disease is non-alcoholic liver steatosis, liver fibrosis or liver cirrhosis.

In another embodiment, the fibrotic disease is idiopathic pulmonary fibrosis.

Cancer and cancer metastasis include, but are not limited to, breast cancer, ovarian cancer, lung cancer, prostate cancer, mesothelioma, glioma, hepatic carcinoma, gastrointestinal cancers and progression and metastatic aggressiveness thereof.

Ocular conditions include, but are not limited to, proliferative and non-proliferative (diabetic) retinopathy, dry and wet age-related macular degeneration (AMD), macular edema, central arterial/venous occlusion, traumatic injury, glaucoma and the like.

Metabolic conditions include, but are not limited to, obesity and diabetes.

In another embodiment, the compounds of formula (I) or their pharmaceutically acceptable salts and esters can be used for the treatment or prophylaxis of cholestatic or non-cholestatic chronic pruritus.

The present invention also relates to the use of a compound according to formula (I) as described herein for the treatment or prophylaxis of renal conditions, liver conditions, inflammatory conditions, conditions of the nervous system, fibrotic diseases and acute and chronic organ transplant rejection.

The present invention also relates to the use of a compound according to formula (I) as described herein for the treatment or prophylaxis of renal conditions, liver conditions and fibrotic diseases.

A particular embodiment of the present invention is a compound according to formula (I) as described herein for the treatment or prophylaxis of renal conditions, liver conditions, inflammatory conditions, conditions of the nervous system, fibrotic diseases and acute and chronic organ transplant rejection.

A particular embodiment of the present invention is a compound according to formula (I) as described herein for the treatment or prophylaxis of renal conditions, liver conditions and fibrotic diseases.

The present invention also relates to the use of a compound according to formula (I) as described herein for the preparation of a medicament for the treatment or prophylaxis of renal conditions, liver conditions, inflammatory conditions, conditions of the nervous system, fibrotic diseases and acute and chronic organ transplant rejection.

The present invention also relates to the use of a compound according to formula (I) as described herein for the preparation of a medicament for the treatment or prophylaxis of renal conditions, liver conditions and fibrotic diseases.

Also an object of the invention is a method for the treatment or prophylaxis of renal conditions, liver conditions, inflammatory conditions, conditions of the nervous system, fibrotic diseases and acute and chronic organ transplant rejection, which method comprises administering an effective amount of a compound according to formula (I) as described herein.

Also an object of the invention is a method for the treatment or prophylaxis of renal conditions, liver conditions and fibrotic diseases, which method comprises administering an effective amount of a compound according to formula (I) as described herein.

In a particular embodiment, the renal condition is selected from the group consisting of acute kidney injury, chronic kidney disease, diabetic nephropathy, acute kidney transplant rejection and chronic allograft nephropathy.

In another particular embodiment, the renal condition is acute kidney injury.

In another particular embodiment, the renal condition is chronic kidney disease.

In a further particular embodiment, the renal condition is diabetic nephropathy.

In another particular embodiment, the renal condition is acute kidney transplant rejection.

In another particular embodiment, the renal condition is chronic allograft nephropathy.

In a particular embodiment, the liver condition is acute and chronic liver transplant rejection In a particular embodiment, the inflammatory condition is arthritis.

In a particular embodiment, the condition of the nervous system is neuropathic pain.

In another embodiment, the fibrotic disease is encapsulating peritonitis

In another embodiment, the fibrotic disease is idiopathic pulmonary fibrosis.

In another embodiment, the fibrotic disease is non-alcoholic liver steatosis, liver fibrosis or liver cirrhosis.

Also an embodiment of the present invention are compounds of formula (I) as described herein, when manufactured according to any one of the described processes.

Assay Procedures

Production of Human Full Length ATX, with and without his Tag

Autotaxin (ATX-ENPP2) Cloning:

cDNA was prepared from commercial human hematopoietic cells total RNA and used as template in overlapping PCR to generate a full length human ENPP2 ORF with or without a 3'-6×His tag. These full length inserts were cloned into the pcDNA3.1V5-His TOPO (Invitrogen) vector. The DNA sequences of several single clones were verified. The DNA from a correct full length clone was used to transfect Hek293 cells for verification of protein expression. The sequence of the encoded ENPP2 conforms to Swissprot entry Q13822, with or without the additional C-terminal 6×His tag.

ATX Fermentation:

Recombinant protein was produced by large-scale transient transfection in 20 L controlled stirred tank bioreactors (Sartorius). During cell growth and transfection, temperature, stirrer speed, pH and dissolved oxygen concentration were maintained at 37° C., 120 rpm, 7.1 and 30% DO, respectively. FreeStyle 293-F cells (Invitrogen) were cultivated in suspension in FreeStyle 293 medium (Invitrogen) and transfected at ca. 1-1.5×10E6 cells/mL with above plasmid DNAs using X-tremeGENE Ro-1539 (commercial product, Roche Diagnostics) as complexing agent. Cells were fed a concentrated nutrient solution (J Immunol Methods 194 (1996), 19, 1-199 (page 193)) and induced by sodium butyrate (2 mM) at 72 h post-transfection and harvested at 96 h post-transfection. Expression was analyzed by Western Blot, enzymatic assay and/or analytical IMAC chromatography. After cooling the cell suspension to 4° C. in a flow-through heat exchanger, cell separation and sterile filtration of supernatant was performed by filtration through Zeta Plus 60M02 E16 (Cuno) and Sartopore 2 XLG (Sartorius) filter units. The supernatant was stored at 4° C. prior to purification.

ATX Purification:

20 liter of culture supernatant were conditioned for ultrafiltration by adding Brij 35 to a final concentration of 0.02% and by adjusting the pH to 7.0 using 1 M HCl. Then the supernatant was first microfiltered through a 0.2 µm Ultran-Pilot Open Channel PES filter (Whatman) and afterwards concentrated to 1 liter through an Ultran-Pilot Screen Channel PES filter with 30 kDa MWCO (Whatman). Prior to IMAC chromatography, $NiSO_4$ was added to a final concentration of 1 mM. The cleared supernatant was then applied to a HisTrap column (GE Healthcare) previously equilibrated in 50 mM $Na_2HPO_4$ pH 7.0, 0.5 M NaCl, 10% glycerol, 0.3% CHAPS, 0.02% $NaN_3$. The column was washed stepwise with the same buffer containing 20 mM, 40 mM and 50 mM imidazole, respectively. The protein was subsequently eluted using a linear gradient to 0.5 M imidazole in 15 column volumes. ATX containing fractions were pooled and concentrated using an Amicon cell equipped with a 30 kDa PES filter membrane. The protein was further purified by size exclusion chromatography on Superdex S-200 prep grade (XK 26/100) (GE Healthcare) in 20 mM BICINE pH 8.5, 0.15 M NaCl, 10% glycerol, 0.3% CHAPS, 0.02% $NaN_3$. Final yield of protein after purification was 5-10 mg ATX per liter of culture supernatant. The protein was stored at −80° C.

Human Atx Enzyme Inhibition Assay

ATX inhibition was measured by a fluorescence quenching assay using a specifically labeled substrate analogue (MR121 substrate). To obtain this MR121 substrate, BOC and TBS protected 6-amino-hexanoic acid (R)-3-({2-[3-(2-{2-[2-(2-amino-ethoxy)-ethoxy]-ethoxy}-ethoxy)-propionylamino]-ethoxy}-hydroxy-phosphoryloxy)-2-hydroxy-propyl ester (Ferguson et al., Org Lett 2006, 8 (10), 2023) was labeled with MR121 fluorophore (CAS 185308-24-1, 1-(3-carboxypropyl)-11-ethyl-1,2,3,4,8,9,10,11-octahydro-dipyrido[3,2-b:2',3'-i]phenoxazin-13-ium) on the free amine of the ethanolamine side and then, after deprotection, subsequently with tryptophan on the side of the aminohexanoic acid.

Assay working solutions were made as follows:

Assay buffer (50 mM Tris-HCl, 140 mM NaCl, 5 mM KCl, 1 mM $CaCl_2$, 1 mM $MgCl_2$, 0.01% Triton-X-100, pH 8.0;

ATX solution: ATX (human His-tagged) stock solution (1.08 mg/mL in 20 mM bicine, pH 8.5, 0.15 M NaCl, 10% glycerol, 0.3% CHAPS, 0.02% $NaN_3$), diluted to 1.4-2.5× final concentration in assay buffer;

MR121 substrate solution: MR121 substrate stock solution (800 μM MR121 substrate in DMSO), diluted to 2-5× final concentration in assay buffer.

Test compounds (10 mM stock in DMSO, 8 μL) were obtained in 384 well sample plates (Corning Costar #3655) and diluted with 8 μL DMSO. Row-wise serial dilutions were made by transferring 8 μL cpd solution to the next row up to row O. The compound and control solutions were mixed five times and 2 L were transferred to 384 well assay plates (Corning Costar #3702). Then, 15 μL of 41.7 nM ATX solution was added (30 nM final concentration), mixed five times and then incubated for 15 minutes at 30° C. 10 μL of MR121 substrate solution was added (1 μM final concentration), mixed 30 times and then incubated for 15 minutes at 30° C. Fluorescence was then measured every 2 minutes for 1 hour (Perkin Elmer plate: vision multimode reader); light intensity: 2.5%; exp. time: 1.4 sec, Filter: Fluo_630/690 nm) and $IC_{50}$ values were calculated from these readouts.

| Example | IC50 (μM) |
|---|---|
| 1 | 0.029 |
| 1.01 | 0.017 |
| 1.02 | 0.022 |
| 1.03 | 0.009 |
| 1.04 | 0.008 |
| 1.05 | 0.006 |
| 1.06 | 0.007 |
| 1.07 | 0.007 |
| 1.08 | 0.02 |
| 1.09 | 0.005 |
| 1.10 | 0.008 |
| 1.11 | 0.015 |
| 1.12 | 0.009 |
| 1.13 | 0.003 |
| 1.14 | 0.009 |

-continued

| Example | IC50 (μM) |
|---|---|
| 1.15 | 0.032 |
| 1.16 | 0.006 |
| 1.17 | 0.019 |
| 1.18 | 0.004 |
| 1.19 | 0.007 |
| 1.2 | 0.014 |
| 1.21 | 0.005 |
| 1.22 | 0.014 |
| 1.23 | 0.013 |
| 2 | 0.091 |
| 2.01 | 0.003 |
| 2.02 | 0.017 |
| 2.03 | 0.01 |
| 2.04 | 0.04 |
| 2.05 | 0.0105 |
| 2.06 | 0.0045 |
| 2.07 | 0.01 |
| 2.08 | 0.0685 |
| 2.09 | 0.02 |
| 2.1 | 0.003 |
| 2.11 | 0.009 |
| 2.12 | 0.011 |
| 2.13 | 0.01 |
| 2.14 | 0.006 |
| 2.15 | 0.012 |
| 2.16 | 0.017 |
| 2.17 | 0.009 |
| 2.18 | 0.01 |
| 2.19 | 0.01 |
| 2.20 | 0.04 |
| 2.21 | 0.006 |
| 2.22 | 0.01 |
| 2.23 | 0.005 |
| 2.24 | 0.011 |
| 2.25 | 0.017 |
| 2.26 | 0.014 |
| 2.27 | 0.019 |
| 2.28 | 0.007 |
| 2.29 | 0.007 |
| 2.3 | 0.005 |
| 3 | 0.025 |
| 3.01 | 0.012 |
| 3.02 | 0.025 |
| 4 | 0.019 |
| 4.01 | 0.039 |
| 5 | 0.016 |
| 5.01 | 0.016 |
| 5.02 | 0.007 |
| 5.03 | 0.01 |
| 5.04 | 0.007 |
| 5.05 | 0.006 |
| 6 | 0.005 |
| 7 | 0.006 |

Compounds of formula (I) and their pharmaceutically acceptable salts or esters thereof as described herein have $IC_{50}$ values between 0.00001 μM and 1000 μM, particular compounds have $IC_{50}$ values between 0.0005 μM and 500 μM, further particular compounds have $IC_{50}$ values between 0.0005 μM and 50 μM, more particular compounds have $IC_{50}$ values between 0.0005 μM and 5 μM. These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragees, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) and their pharmaceutically acceptable salts can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragees and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, water, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.001 and 25 mg in can be administered either by single dose per day or per week, or by multiple doses (2 to 4) per day, or by multiple doses per week. It will, however, be clear that the upper or lower limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

All examples and intermediates were prepared under nitrogen atmosphere if not specified otherwise.

Abbreviations: aq.=aqueous; CAS-RN=Chemical Abstracts Service Registry Number; HPLC=high performance liquid chromatography; MS=mass spectrum; sat.=saturated

Example 1

5-((3aS,6aS)-5-(5-Cyclopropyl-6-(tetrahydro-2H-pyran-4-yloxy)nicotinoyl)octahydropyrrolo[3,4-c]pyrrole-2-carbonyl)pyridine-2-sulfonamide

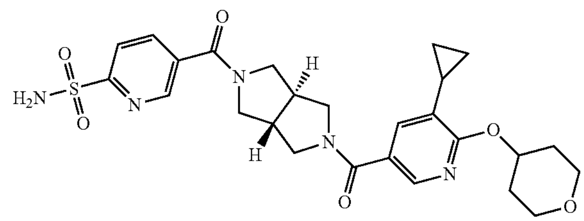 [SMILES: NS(=O)(=O)c1ccc(C(=O)N2C[C@H]3CN(C(=O)c4cnc(OC5CCOCC5)c(C5CC5)c4)C[C@@H]3C2)cn1]

To a solution of (5-cyclopropyl-6-(tetrahydro-2H-pyran-4-yloxy)pyridin-3-yl)((3aS,6aS)-hexahydropyrrolo[3,4-c]pyrrol-2(1H)-yl)methanone hydrochloride (intermediate 1; 40 mg, 95.5 mol) in N,N-dimethylformamide (3 mL) was added 4-methylmorpholine (48.3 mg, 477 mol), 6-sulfamoylnicotinic acid (20.3 mg, 95.5 μmol) and O-(7-azabenzotriazol-1-yl)-N,N,N',N'-tetramethyluronium hexafluorophosphate (39.9 mg, 105 mol) at room temperature, then after 16 h the reaction mixture was partitioned between sat. aq. ammonium chloride solution and ethyl acetate. The organic layer was washed with brine, dried over magnesium sulfate, filtered and evaporated. Chromatography (silica gel, gradient dichloromethane to dichloromethane/methanol/25% aq. ammonia solution 90:10:0.25) produced the title compound (47 mg, 91%). White solid, MS: 542.2 $(M+H)^+$.

The following examples were prepared according to example 1, replacing (5-cyclopropyl-6-(tetrahydro-2H-pyran-4-yloxy)pyridin-3-yl)((3aS,6aS)-hexahydropyrrolo[3,4-c]pyrrol-2(1H)-yl)methanone hydrochloride by the appropriate amine and 6-sulfamoylnicotinic acid by the appropriate carboxylic acid.

| Ex. | Systematic Name | Amine/Carboxylic acid | MS, m/e |
|---|---|---|---|
| 1.01 | 6-((3aR,6aR)-5-(5-cyclopropyl-6-(tetrahydro-2H-pyran-4-yloxy)nicotinoyl)-octahydropyrrolo[3,4-c]pyrrole-2-carbonyl)pyridine-3-sulfonamide 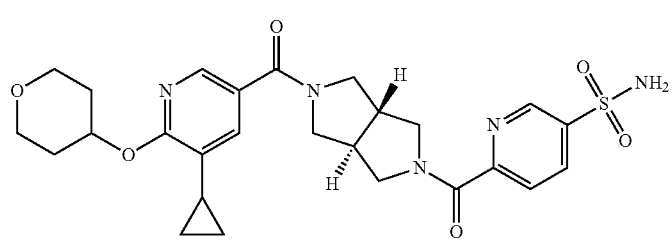 | (5-cyclopropyl-6-(tetrahydro-2H-pyran-4-yloxy)pyridin-3-yl)((3aS,6aS)-hexahydropyrrolo[3,4-c]pyrrol-2(1H)-yl)methanonehydrochloride (intermediate 1)/5-sulfamoylpicolinic acid | 542.2 $(M + H)^+$ |

-continued

| Ex. | Systematic Name | Amine/Carboxylic acid | MS, m/e |
|---|---|---|---|
| 1.02 | 4-((3aS,6aS)-5-(5-cyclopropyl-6-(tetrahydro-2H-pyran-4-yloxy)nicotinoyl)-octahydropyrrolo[3,4-c]pyrrole-2-carbonyl)benzenesulfonamide 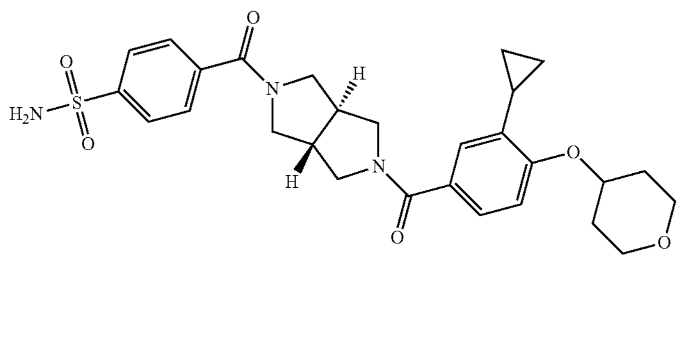 | (5-cyclopropyl-6-(tetrahydro-2H-pyran-4-yloxy) pyridin-3-yl)((3aS,6aS)-hexahydropyrrolo [3,4-c]pyrrol-2(1H)-yl)methanone hydrochloride (intermediate 1)/4-sulfamoylbenzoic acid | 541.2 $(M+H)^+$ |
| 1.03 | 5-((3aR,6aR)-5-(2-cyclopropyl-6-((tetrahydro-2H-pyran-4-yl)methoxy)iso-nicotinoyl)octahydropyrrolo[3,4-c]pyrrole-2-carbonyl)pyridine-2-sulfonamide 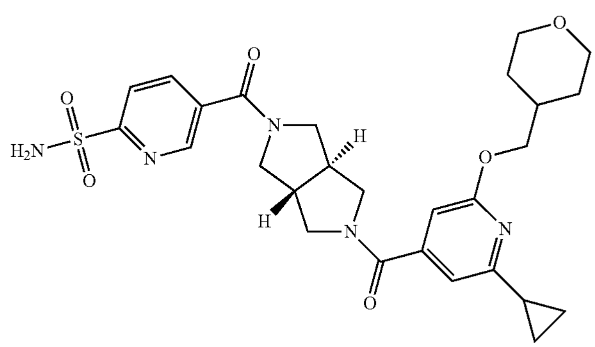 | (2-cyclopropyl-6-((tetrahydro-2H-pyran-4-yl)methoxy)pyridin-4-yl)((3aS,6aS)-hexahydro-pyrrolo[3,4-c]pyrrol-2(1H)-yl)methanone hydrochloride (intermediate 1.1)/ 6-sulfamoyl-nicotinic acid (CAS-RN 285135-56-0) | 556.2 $(M+H)^+$ |
| 1.04 | 4-((3aR,6aR)-5-(2-cyclopropyl-6-((tetra-hydro-2H-pyran-4-yl)methoxy)iso-nicotinoyl)octahydropyrrolo[3,4-c]pyrrole-2-carbonyl-2-fluorobenzenesulfonamide 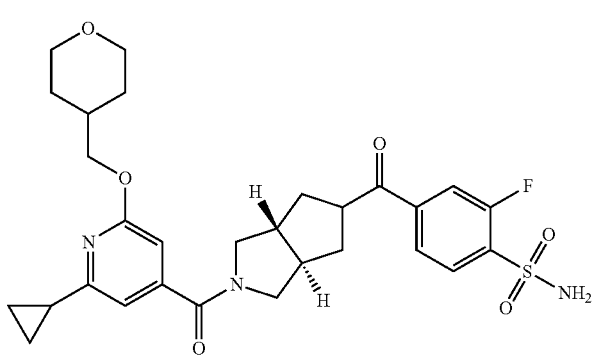 | (2-cyclopropyl-6-((tetrahydro-2H-pyran-4-yl)methoxy)pyridin-4-yl)((3aS,6aS)-hexahydropyrrolo [3,4-c]pyrrol-2(1H)-yl)methanone hydrochloride (intermediate 1.1)/ 3-fluoro-4-sulfamoylbenzoic acid (CAS-RN 244606-37-9) | 573.2 $(M+H)^+$ |

-continued

| Ex. | Systematic Name | Amine/Carboxylic acid | MS, m/e |
|---|---|---|---|
| 1.05 | 2-chloro-4-((3aR,6aR)-5-(2-cyclopropyl-6-((tetrahydro-2H-pyran-4-yl)methoxy)isonicotinoyl)octahydropyrrolo[3,4-c]pyrrole-2-carbonyl)benzenesulfonamide 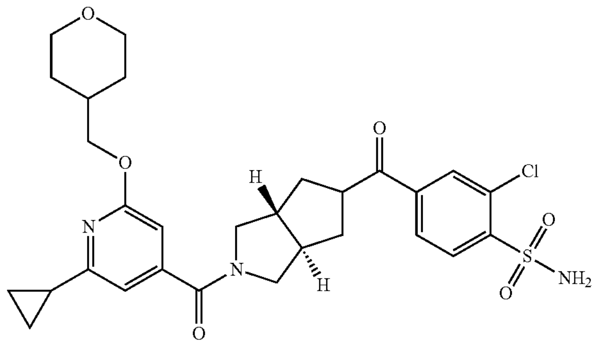 | (2-cyclopropyl-6-((tetrahydro-2H-pyran-4-yl)methoxy)pyridin-4-yl)((3aS,6aS)-hexahydropyrrolo[3,4-c]pyrrol-2(1H)-yl)methanone hydrochloride (intermediate 1.1)/ 3-chloro-4-sulfamoylbenzoic acid (CAS-RN 34263-53-1) | 589.1 (M + H)+ |
| 1.06 | 4-((3aR,6aR)-5-(2-cyclopropyl-6-((tetrahydro-2H-pyran-4-yl)methoxy)-isonicotinoyl)octahydropyrrolo[3,4-c]pyrrole-2-carbonyl)-3-fluorobenzenesulfonamide 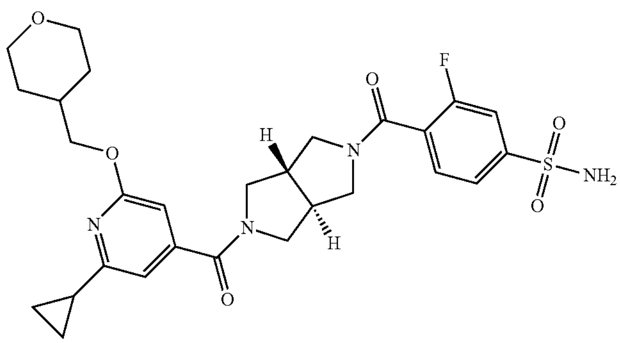 | (2-cyclopropyl-6-((tetrahydro-2H-pyran-4-yl)melhoxy)pyridin-4-yl)((3aS,6aS)-hexahydropyrrolo[3,4-c]pyrrol-2(1H)-yl)methanone hydrochloride (intermediate 1.1)/ 2-fluoro-4-sulfamoylbenzoic acid (CAS-RN 714968-42-0) | 573.3 (M + H)+ |
| 1.07 | ((3aR,8aS)-2-(1H-benzo[d][1,2,3]triazole-5-carbonyl)octahydropyrrolo[3,4-d]azepin-6(7H)-yl)(2-cyclopropyl-6-((tetrahydro-2H-pyran-4-yl)methoxy)pyridin-4-yl)methanone 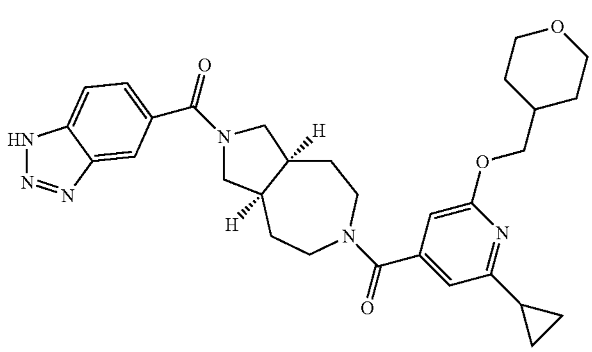 | (2-cyclopropyl-6-((tetrahydro-2H-pyran-4-yl)methoxy) pyridin-4-yl)((3aR,8aS)-octahydropyrrolo[3,4-d]azepin-6(7H)-yl)methanone hydrochloride intermediate 1.2)/ 1H-benzo[d]-[1,2,3]triazole-5-carboxylic acid (CAS-RN 23814-12-2) | 545.3 (M + H)+ |

-continued

| Ex. | Systematic Name | Amine/Carboxylic acid | MS, m/e |
|---|---|---|---|
| 1.08 | 4-((3aS,6aS)-5-(2-cyclopropyl-6-((tetrahydro-2H-pyran-4-yl)methoxy)isonicotinoyl)octahydropyrrolo[3,4-c]pyrrole-2-carbonyl)benzenesulfonamide 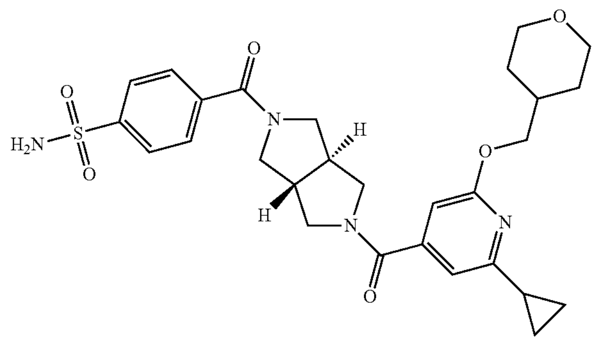 | (2-cyclopropyl-6-((tetrahydro-2H-pyran-4-yl) methoxy)pyridin-4-yl)((3aS,6aS)-hexahydropyrrolo [3,4-c]pyrrol-2(1H)-yl)methanone hydrochloride (intermediate 1.1)/ 4-sulfamoylbenzoic acid (CAS-RN 138-41-0) | 555.3 $(M + H)^+$ |
| 1.09 | 4-((3aR,8aS)-6-(2-cyclopropyl-6-((tetrahydro-2H-pyran-4-yl)methoxy)isonicotinoyl)decahydropyrrolo[3,4-d]azepine-2-carbonyl)benzenesulfonamide 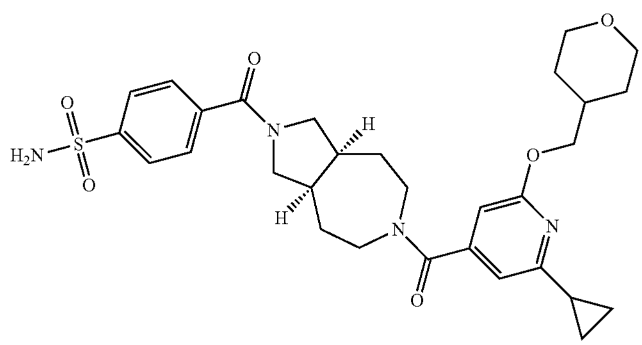 | (2-cyclopropyl-6-((tetrahydro-2H-pyran-4-yl)methoxy) pyridin-4-yl)((3aR,8aS)-octahydropyrrolo [3,4-d]azepin-6(7H)-yl)methanone hydrochloride (intermediate 1.2)/ 4-sulfamoylbenzoic acid (CAS-RN 138-41-0) | 583.4 $(M + H)^+$ |
| 1.10 | ((3aR,8aS)-6-(2-cyclopropyl-6-((tetrahydro-2H-pyran-4-yl)methoxy)isonicotinoyl)-octahydropyrrolo[3,4-d]azepin-2(1H)-yl)(4,5,6,7-tetrahydro-1H-benzo[d][1,2,3]triazol-5-yl)methanone 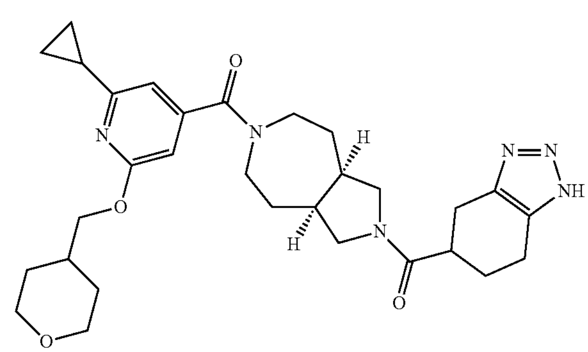 | (2-cyclopropyl-6-((tetrahydro-2H-pyran-4-yl)methoxy) pyridin-4-yl)((3aR,8aS)-octahydropyrrolo [3,4-d]azepin-6(7H)-yl)methanone hydrochloride (intermediate 1.2)/ 4,5,6,7-tetrahydro-1H-benzo[d][1,2,3] triazole-5-carboxylic acid (CAS-RN 33062-47-4) | 549.4 $(M + H)^+$ |

-continued

| Ex. | Systematic Name | Amine/Carboxylic acid | MS, m/e |
| --- | --- | --- | --- |
| 1.11 | ((3aS,6aS)-5-(1H-benzo[d][1,2,3]triazole-5-carbonyl)hexahydropyrrolo[3,4-c]pyrrol-2(1H)-yl)(5-cyclopropyl-6-((tetrahydro-2H-pyran-4-yl)methoxy)pyridin-3-yl)methanone 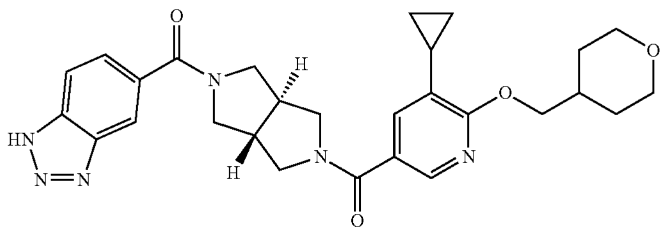 | (5-cyclopropyl-6-((tetrahydro-2H-pyran-4-yl) methoxy)pyridin-3-yl)((3aS,6aS)-hexahydro-pyrrolo[3,4-c] pyrrol-2(1H)-yl)methanone hydrochloride (intermediate 14)/ 1H-benzo[d]-[1,2,3]triazole-5-carboxylic acid (CAS-RN 23814-12-2) | 517.4 $(M + H)^+$ |
| 1.12 | ((3aS,6aS)-5-(5-cyclopropyl-6-((tetra-hydro-2H-pyran-4-yl)methoxy)nicotinoyl)-hexahydropyrrolo[3,4-c]pyrrol-2(1H)-yl)((R)-4,5,6,7-tetrahydro-1H-benzo[d][1,2,3]triazol-5-yl)methanone 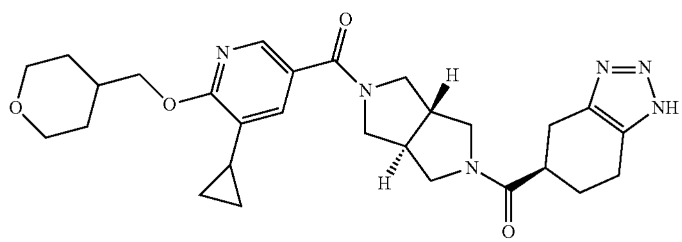 | (5-cyclopropyl-6-((tetrahydro-2H-pyran-4-yl) methoxy)pyridin-3-yl)((3aS,6aS)-hexahydro-pyrrolo[3,4-c] pyrrol-2(1H)-yl)methanone hydrochloride (intermediate 14)/ (R)-4,5,6,7-tetrahydro-1H-benzo[d]-[1,2,3]triazole-5-carboxylic acid (intermediate 4) | 521.4 $(M + H)^+$ |
| 1.13 | 1-((3aS,6aS)-5-(2-cyclopropyl-6-((tetra-hydro-2H-pyran-4-yl)methoxy)iso-nicotinoyl)hexahydropyrrolo[3,4-c]pyrrol-2(1H)-yl)-3-(1H,-1,2,3-triazol-5-yl)propan-1-one 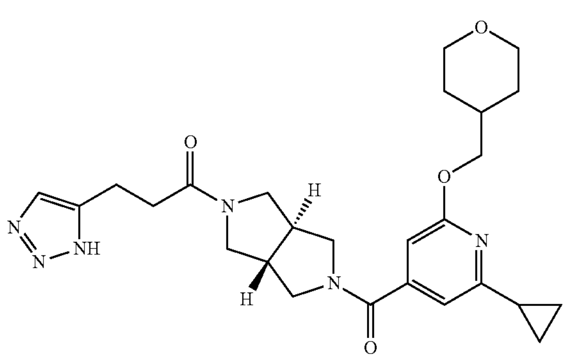 | (2-cyclopropyl-6-((tetrahydro-2H-pyran-4-yl) methoxy)pyridin-4-yl)((3aS,6aS)-hexahydropyrrolo [3,4-c]pyrrol-2(1H)-yl)methanone hydrochloride (intermediate 1.1)/ 3-(1H-1,2,3-triazol-5-yl)propanoic acid (CAS-RN 1225439-19-9) | 495.4 $(M + H)^+$ |

-continued

| Ex. | Systematic Name | Amine/Carboxylic acid | MS, m/e |
|---|---|---|---|
| 1.14 | ((3aR,8aS)-2-(1H-benzo[d][1,2,3]triazole-5-carbonyl)octahydropyrrolo[3,4-d]azepin-6(2H)-yl)(3-cyclopropyl-5-((tetrahydro-2H-pyran-4-yl)methoxy)phenyl)methanone 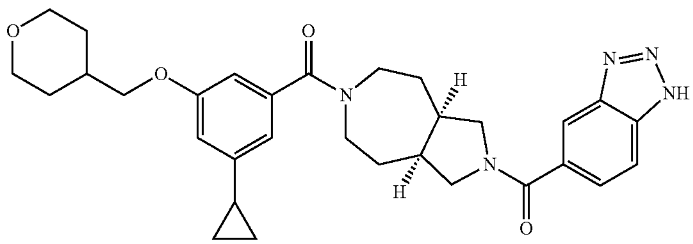 | [(3aS,8aR)-2,3,3a,4,5,7,8,8a-octahydro-1H-pyrrolo[3,4-d] azepin-6-yl]-[3-cyclopropyl-5-(oxan-4-ylmethoxy)phenyl] methanone (intermediate 16)/ 1H-benzo[d]-[1,2,3]triazole-5-carboxylic acid (CAS-RN 23814-12-2) | 544.3 (M + H)$^+$ |
| 1.15 | 1-((3aR,8aS)-6-(3-cyclopropyl-5-((tetrahydro-2H-pyran-4-yl)methoxy)benzoyl)octahydropyrrolo[3,4-d]azepin-2(1H)-yl)-3-(1H-1,2,3-triazol-4-yl)propan-1-one 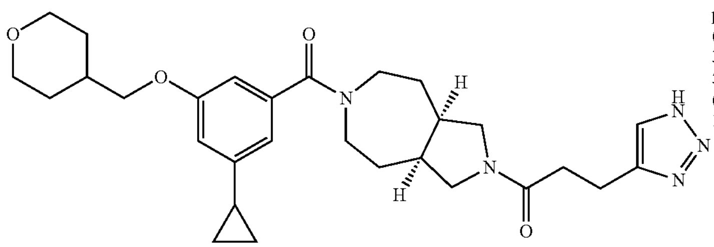 | [(3aS,8aR)-2,3,3a,4,5,7,8,8a-octahydro-1H-pyrrolo[3,4-d]azepin-6-yl]-[3-cyclopropyl-5-(oxan-4-ylmethoxy) phenyl]methanone (intemiediate 16)/ 3-(1H-1,2,3-triazol-5-yl)propanoic acid (CAS-RN 1225439-19-9) | 522.3 (M + H)$^+$ |
| 1.16 | ((3aS,6aS)-5-(3-cyclopropyl-5-((tetrahydro-2H-pyran-4-yl)methoxy)benzoyl)hexahydropyrrolo[3,4-c]pyrrol-2(1H)-yl)((R)-4,5,6,7-tetrahydro-1H-benzo[d][1,2,3]triazol-5-yl)methanone 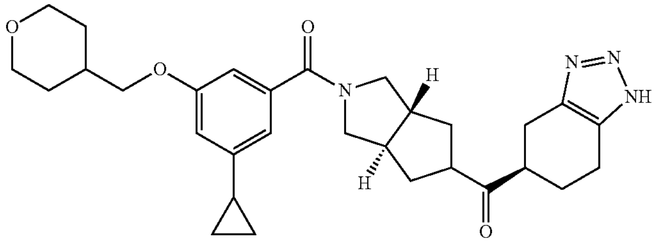 | [(3aS,6aS)-2,3,3a,4,6,6a-hexahydro-1H-pyrrolo[3,4-c]pyrrol-5-yl]-[3-cyclopropyl-5-(oxan-4-ylmethoxy)phenyl] methanone (intermediate 16.1)/ (R)-4,5,6,7-tetrahydro-1H-benzo[d][1,2,3] triazole-5-carboxylic acid (intermediate 4) | 520.3 (M + H)$^+$ |

-continued

| Ex. | Systematic Name | Amine/Carboxylic acid | MS, m/e |
|---|---|---|---|
| 1.17 | 4-((3aS,6aS)-5-(3-cyclopropyl-5-((tetrahydro-2H-pyran-4-yl)methoxy)benzoyl)octahydropyrrolo[3,4-c]pyrrole-2-carbonyl)benzenesulfonamide 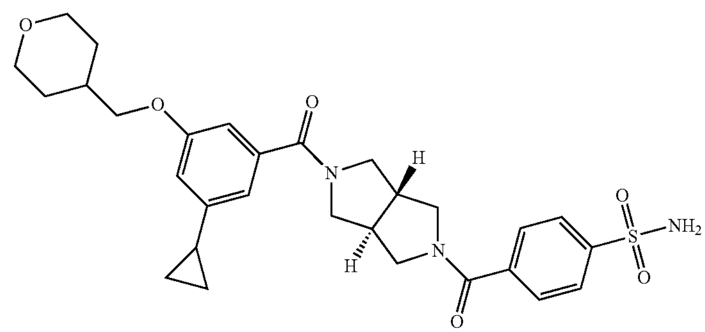 | [(3aS,6aS)-2,3,3a,4,6,6a-hexahydro-1H-pyrrolo[3,4-c]pyrrol-5-yl]-[3-cyclopropyl-5-(oxan-4-ylmethoxy)phenyl] methanone (intermediate 16.1)/ 4-sulfamoylbenzoic acid (CAS-RN 138-41-0) | 554.3 $(M + H)^+$ |
| 1.18 | 4-((3aR,6aR)-5-(3-cyclopropyl-5-((tetrahydro-2H-pyran-4-yl)methoxy)benzoyl)octahydropyrrolo[3,4-c]pyrrole-2-carbonyl)-3-fluorobenzenesulfonamide 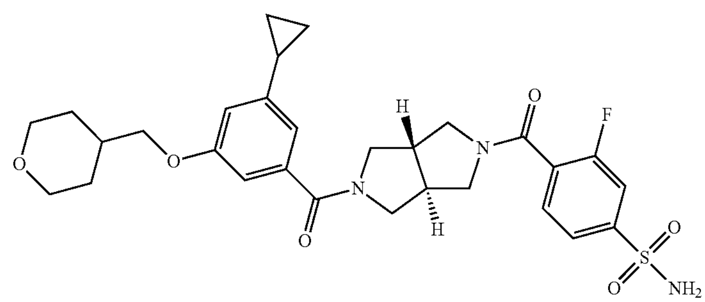 | [(3aS,6aS)-2,3,3a,4,6,6a-hexahydro-1H-pyrrolo[3,4-c]pyrrol-5-yl]-[3-cyclopropyl-5-(oxan-4-ylmethoxy)phenyl] methanone (intermediate 16.1)/ 2-fluoro-4-sulfamoylbenzoic acid (CAS-RN 714968-42-0) | 572.3 $(M + H)^+$ |
| 1.19 | 5-((3aR,8aS)-6-(2-cyclopropyl-6-((tetrahydro-2H-pyran-4-yl)methoxy)-isonicotinoyl)decahydropyrrolo[3,4-d]azepine-2-carbonyl)-1H-benzo[d]imidazol-2(3H)-one 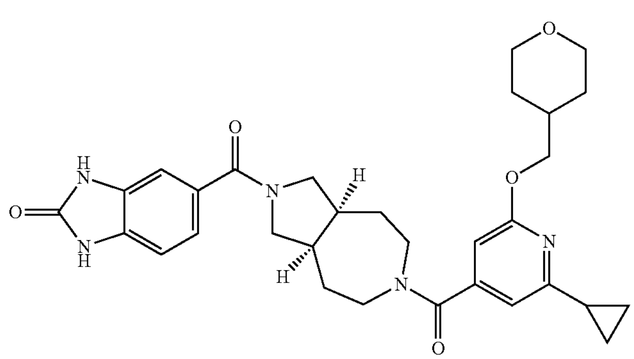 | (2-cyclopropyl-6-((tetrahydro-2H-pyran-4-yl)methoxy)pyridin-4-yl)((3aR,8aS)-octahydropyrrolo [3,4-d]azepin-6(7H)-yl)methanone hydrochloride (intermediate 1.2)/ 2-oxo-1,3-dihydro-benzimidazole-5-carboxylic acid (CAS-RN 23814-14-4) | 560.3 $(M + H)^+$ |

-continued

| Ex. | Systematic Name | Amine/Carboxylic acid | MS, m/e |
| --- | --- | --- | --- |
| 1.20 | 6-((3aR,8aS)-6-(2-cyclopropyl-6-((tetrahydro-2H-pyran-4-yl)methoxy)-isonicotinoyl)decahydropyrrolo[3,4-d]azepine-2-carbonyl)-1-methyl-1H-benzo[d]imidazol-2(3H)-one 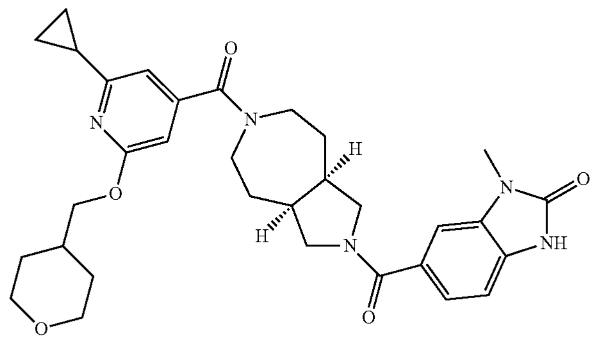 | (2-cyclopropyl-6-((tetrahydro-2H-pyran-4-yl)methoxy)pyridin-4-yl)((3aR,8aS)-octahydropyrrolo[3,4-d]azepin-6(7H)-yl)methanone hydrochloride (intermediate 1.2)/ 3-methyl-2-oxo-1H-benzimidazole-5-carboxylic acid (CAS-RN 863564-77-6) | 574.3 $(M + H)^+$ |
| 1.21 | 5-(3-((3aR,8aS)-6-(2-cyclopropyl-6-((tetrahydro-2H-pyran-4-yl)methoxy)-isonicotinoyl)octahydropyrrolo[3,4-d]azepine-2(1H)-yl)-3-oxopropyl)oxazol-2(3H)-one 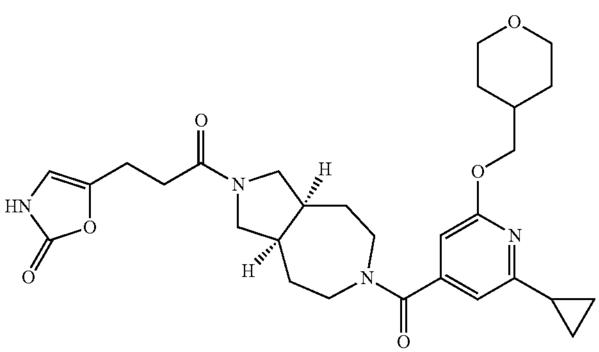 | (2-cyclopropyl-6-((tetrahydro-2H-pyran-4-yl)methoxy)pyridin-4-yl)((3aR,8aS)-octahydropyrrolo[3,4-d]azepin-6(7H)-yl)methanone hydrochloride (intermediate 1.2)/ 3-(2-oxo-3H-1,3-oxazol-5-yl) propanoic acid (CAS-RN 1520136-12-2) | 539.3 $(M + H)^+$ |
| 1.22 | 5-(3-((3aR,8aS)-6-(2-cyclopropyl-6-((tetrahydro-2H-pyran-4-yl)methoxy)-isonicotinoyl)octahydropyrrolo[3,4-d]azepine-2(1H)-yl)-3-oxopropyl)oxazol-2(3H)-one 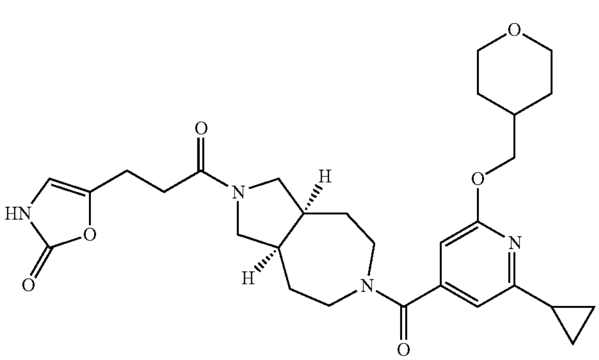 | (2-cyclopropyl-6-((tetrahydro-2H-pyran-4-yl)methoxy)pyridin-4-yl)((3aR,8aS)-octahydropyrrolo[3,4-d]azepin-6(7H)-yl)methanone hydrochloride (intermediate 1.2)/ 3-(2-oxo-3H-1,3-thiazol-5-yl)propanoic acid (CAS-RN 1553678-73-1) | 555.3 $(M + H)^+$ |

-continued

| Ex. | Systematic Name | Amine/Carboxylic acid | MS, m/e |
|---|---|---|---|
| 1.23 | 1-((3aR,8aS)-6-(2-cyclopropyl-6-((tetrahydro-2H-pyran-4-yl)methoxy)-isonicotinoyl)octahydropyrrolo[3,4-d]azepin-2(1H)-yl)-3-(3-hydroxyisoxazol-5-yl)propan-1-one 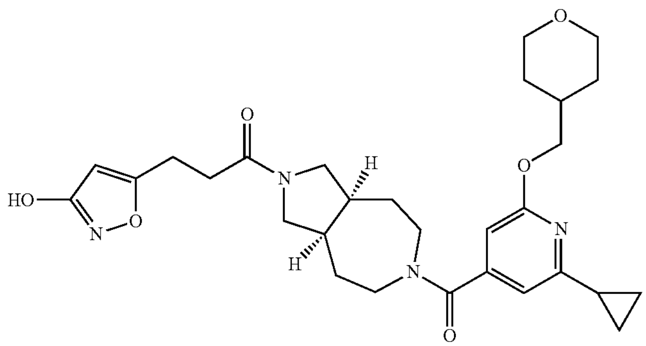 | (2-cyclopropyl-6-((tetrahydro-2H-pyran-4-yl)methoxy)pyridin-4-yl)((3aR,8aS)-octahydropyrrolo[3,4-d]azepin-6(7H)-yl)methanone hydrochloride (intermediate 1.2)/ 3-(3-hydroxy-1,2-oxazol-5-yl)propanoic acid (CAS-RN 75989-19-4) | 539.3 $(M + H)^+$ |

Example 2

4-((3aR,6aS)-5-(5-Cyclopropyl-6-(tetrahydro-2H-pyran-4-yloxy)nicotinoyl)octahydropyrrolo[3,4-c]pyrrole-2-carbonyl)benzenesulfonamide

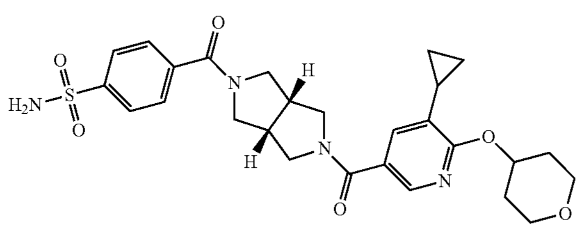 [SMILES: NS(=O)(=O)c1ccc(C(=O)N2C[C@@H]3CN(C(=O)c4cnc(OC5CCOCC5)c(C5CC5)c4)C[C@@H]3C2)cc1]

To a solution of 4-((3aR,6aS)-octahydropyrrolo[3,4-c]pyrrole-2-carbonyl)benzenesulfonamide hydrochloride (intermediate 2; 30 mg, 90.4 μmol) in N,N-dimethylformamide (3 mL) was added 4-methylmorpholine (45.7 mg, 452 μmol), 5-cyclopropyl-6-(tetrahydro-2H-pyran-4-yloxy) nicotinic acid (intermediate 6.1; 28.7 mg, 90.4 μmol) and O-(7-azabenzotriazol-1-yl)-N,N,N',N'-tetramethyluronium hexafluoro-phosphate (37.8 mg, 99.5 μmol) at room temperature, then after 16 h the reaction mixture was partitioned between sat. aq. ammonium chloride solution and ethyl acetate. The organic layer was washed with brine, dried over magnesium sulfate, filtered and evaporated. Chromatography (silica gel, gradient dichloromethane to dichloromethane/methanol/25% aq. ammonia solution 90:10:0.25) produced the title compound (39 mg, 76%). White solid, MS: 541.3 (M+H)+.

The following examples were prepared according to example 2, replacing 4-((3aR,6aS)-octahydropyrrolo[3,4-c]pyrrole-2-carbonyl)benzenesulfonamide hydrochloride by the appropriate amine and 5-cyclopropyl-6-(tetrahydro-2H-pyran-4-yloxy)nicotinic acid by the appropriate carboxylic acid.

| Ex. | Systematic Name | Amine/Carboxylic acid | MS, m/e |
|---|---|---|---|
| 2.01 | ((3aS,6aS)-5-(1H-benzo[d][1,2,3]triazole-5-carbonyl)hexahydropyrrol[3,4-c]pyrrol-2(1H)-yl)(2-cyclopropyl-6-((tetrahydro-2H-pyran-4-yl)methoxy)pyridin-4-yl)methanone 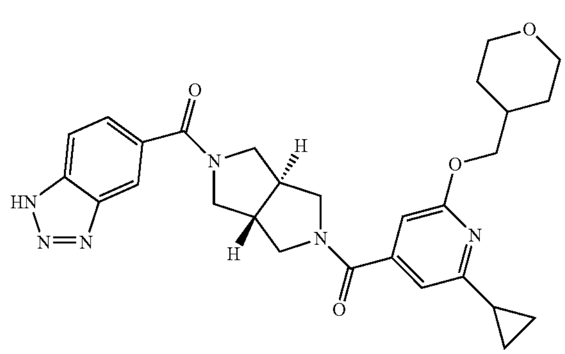 | (1H-benzo[d][1,2,3]triazol-5-yl)((3aR,6aR)-hexahydropyrrolo[3,4-c]pyrrol-2(1H)-yl)methanone hydrochloride (intermediate 2.2)/2-cyclopropyl-6-((tetrahydro-2H-pyran-4-yl)methoxy)isonicotinic acid (intermediate 5) | 517.4 $(M + H)^+$ |

-continued

| Ex. | Systematic Name | Amine/Carboxylic acid | MS, m/e |
|---|---|---|---|
| 2.02 | ((3aS,6aS)-5-(3-cyclopropyl-4-(tetrahydrofuran-3-ylozy)benzoyl)hexahydropyrrolo[3,4-c]pyrrol-2(1H)-yl)((R-4,5,6,7-tetrahydro-1H-benzo[d][1,2,3]triazol-5-yl)methanone 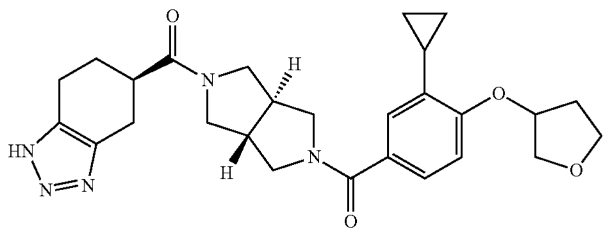 | ((3aR,6aR)-hexahydro-pyrrolo[3,4-c]pyrrol-2(1H)-yl)((R)-4,5,6,7-tetrahydro-1H-benzo[d][1,2,3]triazol-5-yl)methanone hydrochloride (intermediate 2.1)/3-cyclopropyl-4-(tetrahydrofuran-3-yloxy)benzoic acid (intermediate 9) | 492.3 (M + H)+ |
| 2.03 | ((3aR,6aR)-5-(1H-benzo[d][1,2,3]triazole-5-carbonyl)hexahydropyrrolo[3,4-c]pyrrol-2(1H)-yl(3-cyclopropyl-4-(tetrahydrofuran-3-yloxy)phenyl)methanone 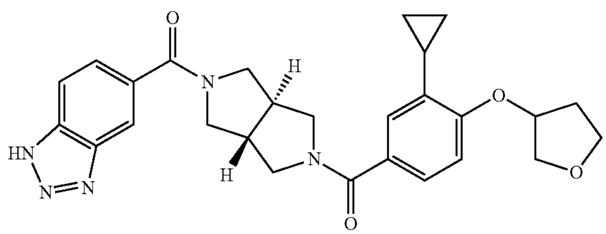 | (1H-benzo[d][1,2,3]triazol-5-yl)((3aR,6aR)-hexahydropyrrolo[3,4-c]pyrrol-2(1H)-yl)methanone hydrochloride (intermediate 2.2)/3-cyclopropyl-4-(tetrahydrofuran-3-yloxy)benzoic acid (intermediate 9) | 488.3 (M + H)+ |
| 2.04 | ((3aS,6aS)-5-(1H-benzo[d][1,2,3]triazole-5-carbonyl)hexahydropyrrolo[3,4-c]pyrrol-2(1H)-yl(5-cyclopropyl-6-(tetrahydro-2H-pyran-4-ylamino)pyridin-3-yl)methanone 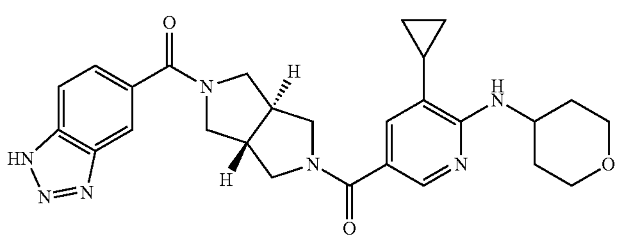 | (1H-benzo[d][1,2,3]triazol-5-yl)((3aR,6aR)-hexahydropyrrolo[3,4-c]pyrrol-2(1H)-yl)methanone hydrochloride (intermediate 2.2)/5-cyclopropyl-6-(tetrahydro-2H-pyran-4-ylamino)nicotinic acid (intermediate 7) | 502.3 (M + H)+ |
| 2.05 | ((3aS,6aS)-5-(1H-benzo[d][1,2,3]triazole-5-carbonyl)hexahydropyrrolo[3,4-c]pyrrol-2(1H)-yl(5-cyclopropyl-6-(tetrahydrofuran-3-yloxy)pyridin-3-yl)methanone 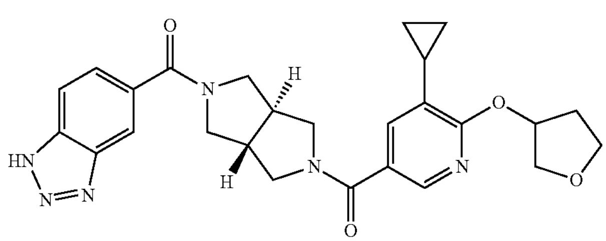 | (1H-benzo[d][1,2,3]triazol-5-yl)((3aR,6aR)-hexahydropyrrolo[3,4-c]pyrrol-2(1H)-yl)methanone hydrochloride (intermediate 2.2)/5-cyclopropyl-6-(tetrahydrofuran-3-yloxy)nicotinic acid (intermediate 6) | 489.2 (M + H)+ |

-continued

| Ex. | Systematic Name | Amine/Carboxylic acid | MS, m/e |
|---|---|---|---|
| 2.06 | ((3aS,6aS)-5-(1H-benzo[d][1,2,3]triazole-5-carbonyl)hexahydropyrrolo[3,4-c]pyrrol-2(1H)-yl(5-cyclopropyl-6-(tetrahydro-2H-pyran-3-yloxy)pyridin-3-yl)methanone 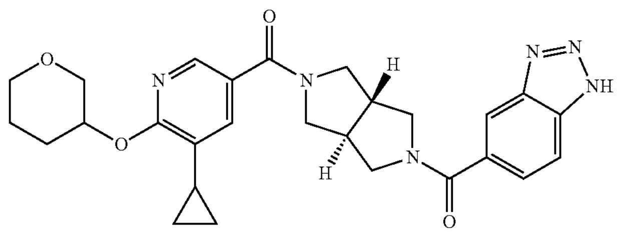 | (1H-benzo[d][1,2,3]triazol-5-yl)((3aR,6aR)-hexahydropyrrolo[3,4-c]pyrrol-2(1H)-yl)methanone hydrochloride (intermediate 2.2)/5-cyclopropyl-6-(tetrahydro-2H-pyran-3-yloxy)nicotinic acid (intermediate 6.2) | 503.3 $(M + H)^+$ |
| 2.07 | ((3aS,6aS)-5-(1H-benzo[d][1,2,3]triazole-5-carbonyl)hexahydropyrrolo[3,4-c]pyrrol-2(1H)-yl(5-cyclopropyl-6-(tetrahydro-2H-pyran-4-yloxy)pyridin-3-yl)methanone 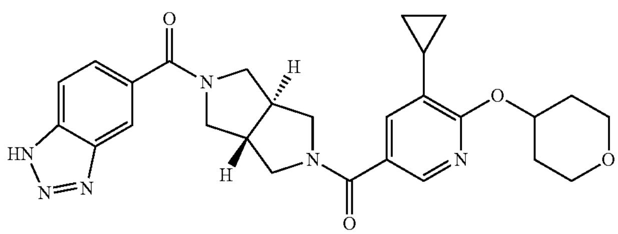 | (1H-benzo[d][1,2,3]triazol-5-yl)((3aR,6aR)-hexahydropyrrolo[3,4-c]pyrrol-2(1H)-yl)methanone hydrochloride (intermediate 2.2)/5-cyclopropyl-6-(tetrahydro-2H-pyran-4-yloxy)nicotinic acid (intermediate 6.1) | 503.3 $(M + H)^+$ |
| 2.08 | ((3aS,6aS)-5-(1H-benzo[d][1,2,3]triazole-5-carbonyl)hexahydropyrrolo[3,4-c]pyrrol-2(1H)-yl(6-(oxetan-3-yloxy)-5-(trifluoromethyl)pyridin-3-yl)methanone 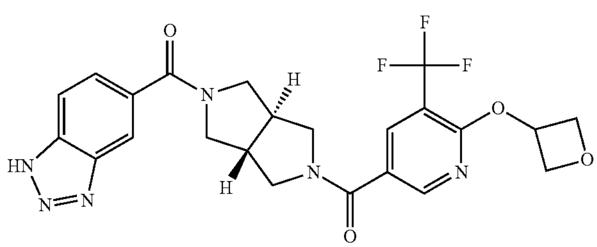 | (1H-benzo[d][1,2,3]triazol-5-yl)((3aR,6aR)-hexahydropyrrolo[3,4-c]pyrrol-2(1H)-yl)methanone hydrochloride (intermediate 2.2)/6-(oxetan-3-yloxy)-5-(trifluoromethyl)nicotinic acid (intermediate 8) | 503.2 $(M + H)^+$ |
| 2.09 | ((3aS,6aS)-5-(5-cyclopropyl-6-(tetrahydro-2H-pyran-4-yloxy)nicotinoyl)hexahydro-pyrrolo[3,4-c]pyrrol-2(1H)-yl)((R)-4,5,6,7-tetrahydro-1H-benzo[d][1,2,3]triazol-5-yl)methanone 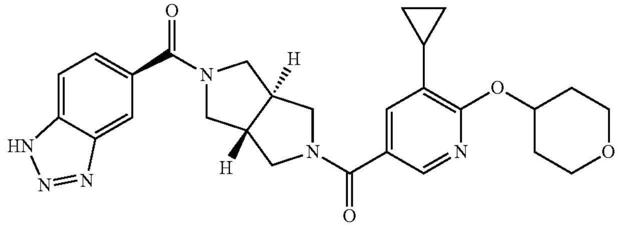 | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.1)/5-cyclopropyl-6-(tetrahydro-2H-pyran-4-yloxy)nicotinic acid (intermediate 6.1) | 507.3 $(M + H)^+$ |

-continued

| Ex. | Systematic Name | Amine/Carboxylic acid | MS, m/e |
|---|---|---|---|
| 2.10 | ((3aS,6aS)-5-(2-cyclopropyl-6-(tetrahydro-2H-pyran-4-yl)methoxy)isonicotinoyl)-hexahydropyrrolo[3,4-c]pyrrol-2(1H)-yl)((R)-4,5,67-tetrahydro-1H-benzo[d][1,2,3]triazol-5-yl)methanone 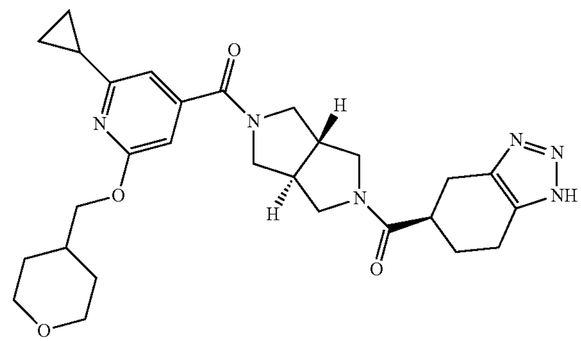 | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.1)/2-cyclopropyl-6-((tetrahydro-2H-pyran-4-yl)methoxy)isonicotinic acid (intermediate 5) | 521.3 $(M + H)^+$ |
| 2.11 | ((3aS,6aS)-5-(5-cyclopropyl-6-(tetrahydro-2H-pyran-4-ylamino)nicotinoyl)hexahydropyrrolo[3,4-c]pyrrol-2(1H)-yl)((R)-4,5,6,7-tetrahydro-1H-benzo[d][1,2,3]triazol-5-yl)methanone 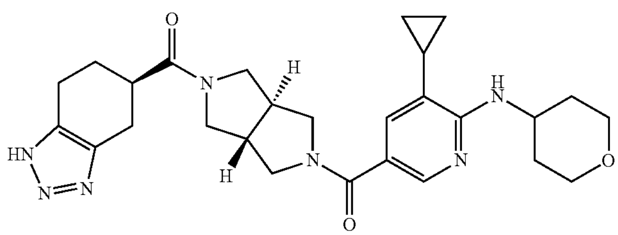 | ((3aR,6aR) hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.1)/5-cyclopropyl-6-(tetrahydro-2H-pyran-4-ylamino)nicotinic acid (intermediate 7) | 506.3 $(M + H)^+$ |
| 2.12 | ((3aS,6aS)-5-(5-cyclopropyl-6-(tetrahydro-2H-pyran-3-yloxy)nicotinoyl)hexahydropyrrolo[3,4-c]pyrrol-2(1H)-yl)((R)-4,5,6,7-tetrahydro-1H-benzo[d][1,2,3]triazol-5-yl)methanone 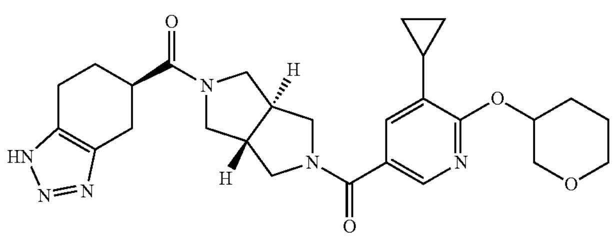 | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.1)/5-cyclopropyl-6-(tetrahydro-2H-pyran-3-yloxy)nicotinic acid (intermediate 6.2) | 507.3 $(M + H)^+$ |
| 2.13 | 6-((3aR,6aR)-5-(5-cyclopropyl-6-(tetra-hydro-2H-pyran-3-yloxy)nicotinoyl)-octahydropyrrolo[3,4-c]pyrrole-2-carbonyl)pyridine-3-sulfonamine 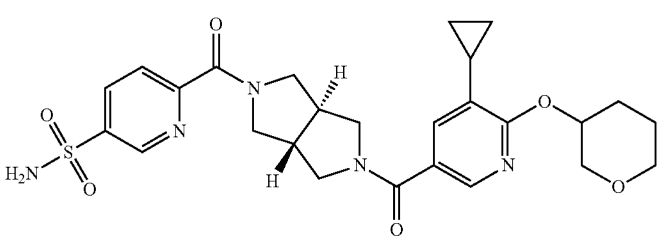 | 6-((3aR,6aR)-octahydropyrrolo[3,4-c]pyrrole-2-carbonyl)pyridine-3-sulfonamide hydrochloride (intermediate 2.3)/5-cyclopropyl-6-(tetrahydro-2H-pyran-3-yloxy)nicotinic acid (intermediate 6.2) | 542.2 $(M + H)^+$ |

-continued

| Ex. | Systematic Name | Amine/Carboxylic acid | MS, m/e |
|---|---|---|---|
| 2.14 | 6-((3aR,6aR)-5-(2-cyclopropyl-6-(tetrahydro-2H-pyran-4-yl)methoxy)isonicotinoyl)octahydropyrrolo[3,4-c]pyrrole-2-carbonyl)pyridine-3-sulfonamide 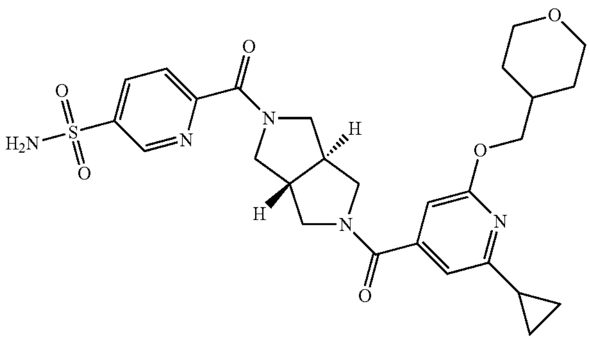 | 6-((3aR,6aR)-octahydropyrrolo[3,4-c]pyrrole-2-carbonyl)pyridine-3-sulfonamide hydrochloride (intermediate 2.3)/2-cyclopropyl-6-((tetrahydro-2H-pyran-4-yl)methoxy)isonicotinic acid (intermediate 5) | 556.2 (M + H)+ |
| 2.15 | ((3aS,6aS)-5-(1H-benzo[d][1,2,3]triazole-5-carbonyl)hexahydropyrrolo[3,4-c]pyrrol-2(1H)-yl)(2-cyclopropyl-6-((tetrahydro-2H-pyran-3-yl)methoxy)pyridin-4-yl)methanone 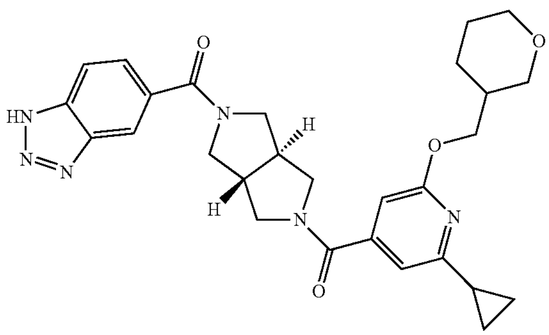 | (1H-benzo[d][1,2,3]triazol-5-yl)((3aR,6aR)-hexahydropyrrolo[3,4-c]pyrrol-2(1H)-yl)methanone dihydrochloride (intermediate 2.2)/2-cyclopropyl-6-((tetrahydro-2H-pyran-3-yl)methoxy)isonicotinic acid (intermediate 5.1) | 517.3 (M + H)+ |
| 2.16 | ((3aS,6aS)-5-(2-cyclopropyl-6-((tetrahydro-2H-pyran-3-yl)methoxy)isonicotinoyl)-hexahydropyrrolo[3,4-c]pyrrol-2(1H)-yl)((R)-4,5,6,7-tetrahydro-1H-benzo[d][1,2,3]triazol-5-yl)methanone 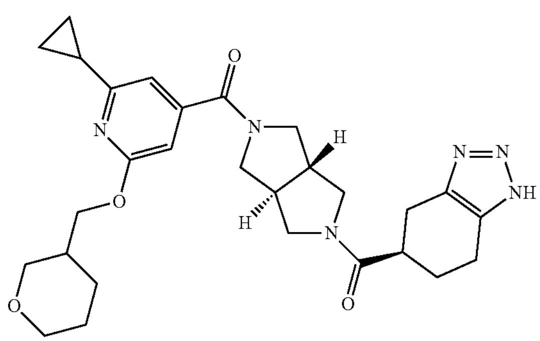 | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.1)/2-cyclopropyl-6-((tetrahydro-2H-pyran-3-yl)methoxy)isonicotinic acid (intermediate 5.1) | 521.4 (M + H)+ |

-continued

| Ex. | Systematic Name | Amine/Carboxylic acid | MS, m/e |
|---|---|---|---|
| 2.17 | 6-((3aR,6aR)-5-(2-cyclopropyl-6-(tetra-hydro-2H-pyran-3-yl)methoxy)iso-nicotinoyl)octahydropyrrolo[3,4-c]pyrrole-2-carbonyl)pyridine-3-sulfonamide 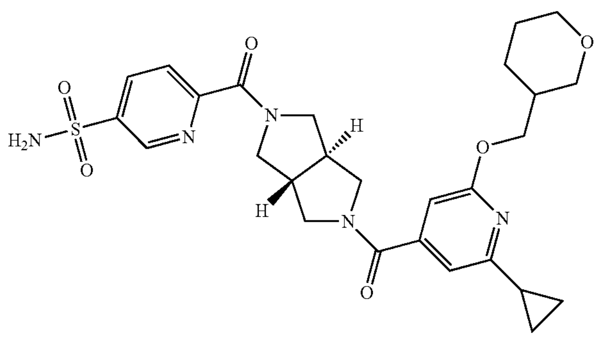 | 6-((3aR,6aR)-octahydropyrrolo[3,4-c]pyrrole-2-carbonyl)pyridine-3-sulfonamide hydrochloride (intermediate 2.3)/2-cyclopropyl-6-((tetrahydro-2H-pyran-3-yl)methoxy)isonicotinic acid (intermediate 5.1) | 556.3 $(M + H)^+$ |
| 2.18 | ((3aS,6aS)-5-(1H-benzo[d][1,2,3]triazole-5-yl)methyl)hexahydropyrrolo[3,4-c]pyrrol-2(1H)-yl)(2-cyclopropyl-6-((tetrahydro-2H-pyran-4-yl)methoxy)pyridin-4-yl)methanone 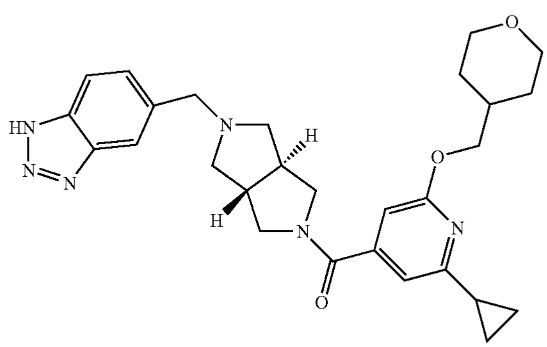 | 5-(((3aR,6aR)-hexahydropyrrolo[3,4-c]pyrrol-2(1H)-yl)methyl)-1H-benzo[d][1,2,3]triazole hydrochloride (intermediate 10)/2-cyclopropyl-6-((tetrahydro-2H-pyran-4-yl)methoxy)isonicotinic acid (intermediate 5) | 503.4 $(M + H)^+$ |
| 2.19 | ((3aS,6aS)-5-(1H-benzo[d][1,2,3]triazole-5-yl)methyl)hexahydropyrrolo[3,4-c]pyrrol-2(1H)-yl)(2-cyclopropyl-6-((tetrahydro-2H-pyran-3-yl)methoxy)pyridin-4-yl)methanone 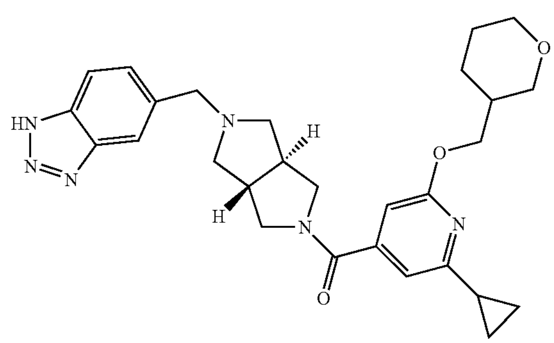 | 5-(((3aR,6aR)-hexahydropyrrolo[3,4-c]pyrrol-2(1H)-yl)methyl)-1H-benzo[d][1,2,3]triazole hydrochloride (intermediate 10)/2-cyclopropyl-6-((tetrahydro-2H-pyran-3-yl)methoxy)isonicotinic acid (intermediate 5.1) | 503.4 $(M + H)^+$ |

-continued

| Ex. | Systematic Name | Amine/Carboxylic acid | MS, m/e |
|---|---|---|---|
| 2.20 | ((3aS,6aS)-5-(1H-benzo[d][1,2,3]triazole-5-carbonyl)hexahydropyrrolo[3,4-c]pyrrol-2(1H)-yl)(2-chloro-6-((tetrahydro-2H-pyran-4-yl)methoxy)pyridin-4-yl)methanone 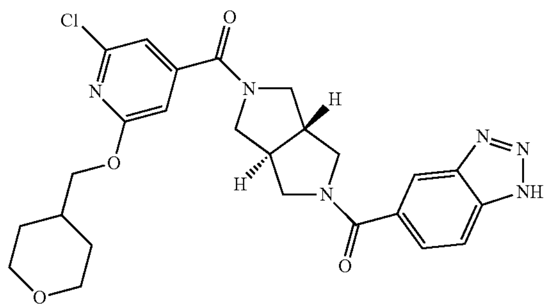 | (1H-benzo[d][1,2,3]triazol-5-yl)((3aR,6aR)-hexahydropyrrolo[3,4-c]pyrrol-2(1H)-yl)methanone dihydrochloride (intermediate 2.2)/2-chloro-6-((tetrahydro-2H-pyran-4-yl)methoxy)isonicotinic acid (CAS-RN 1456284-71-1) | 511.3 $(M + H)^+$ |
| 2.21 | ((3aR,8aS)-6-(2-cyclopropyl-6-((tetrahydro-2H-pyran-4-yl)methoxy)isonicotinoyl)-octahydropyrrolo[3,4-d]azepin-2(1H)-yl)((R)-4,5,6,7-tetrahydro-1H-benzo[d][1,2,3]triazol-5-yl)methanone 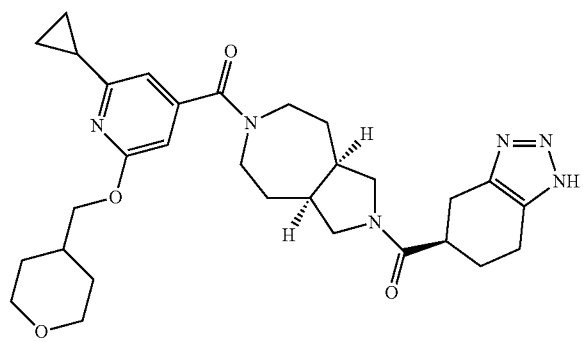 | ((3aR,8aS)-octahydropyrrolo[3,4-d]azepin-2(1H)-yl)((R)-4,5,6,7-tetrahydro-1H-benzo[d][1,2,3]triazol-5-yl)methanone (intermediate 15)/2-cyclopropyl-6-((tetrahydro-2H-pyran-4-yl)methoxy)isonicotinic acid (intermediate 5) | 549.3 $(M + H)^+$ |
| 2.22 | ((3aR,8aS)-6-(1H-benzo[d][1,2,3]triazole-5-carbonyl)octahydropyrrolo[3,4-d]azepin-2(1H)-yl)(2-cyclopropyl-6-((tetrahydro-2H-pyran-4-yl)methoxy)pyridin-4-yl)methanone 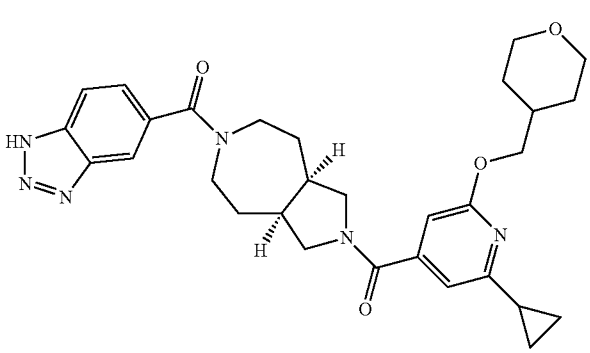 | (1H-benzo[d][1,2,3]triazol-5-yl)((3aR,8aS)-octahydropyrrolo[3,4-d]azepin-6(7H)-yl)methanone hydrochloride (intermediate 2.4)/2-cyclopropyl-6-((tetrahydro-2H-pyran-4-yl)methoxy)isonicotinic acid (intermediate 5) | 545.3 $(M + H)^+$ |

-continued

| Ex. | Systematic Name | Amine/Carboxylic acid | MS, m/e |
|---|---|---|---|
| 2.23 | ((3aS,6aS)-5-(1H-benzo[d][1,2,3]triazole-5-carbonyl)hexahydropyrrolo[3,4-c]pyrrol-2(1H)-yl)(2-(dimethylamino)-6-((tetrahydro-2H-pyran-4-yl)methoxy)pyridin-4-yl)methanone 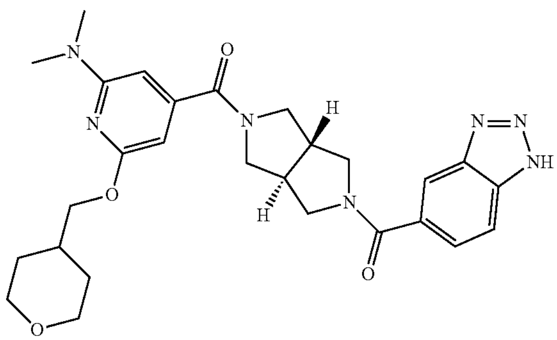 | (1H-benzo[d][1,2,3]triazol-5-yl)((3aR,6aR)-hexahydropyrrolo[3,4-c]pyrrol-2(1H)-yl)methanone dihydrochloride (intermediate 2.2)/2-(dimethylamino)-6-((tetrahydro-2H-pyran-4-yl)methoxy)isonicotinic acid (intermediate 11) | 520.4 $(M + H)^+$ |
| 2.24 | 6-((3aS,6aS)-5-(2-cyclopropyl-6-((tetrahydro-2H-pyran-4-yl)methoxy)isonicotinoyl)hexahydropyrrolo[3,4-c]pyrrol-2(1H)-yl)methyl)benzo[d]oxazol-2(3H)-one 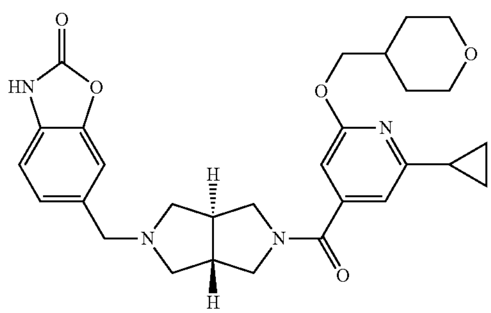 | 6-(((3aR,6aR)-hexahydropyrrolo[3,4-c]pyrrol-2(1H)-yl)methyl)benzo[d]oxazol-2(3H)-one hydrochloride (intermediate 12)/2-cyclopropyl-6-((tetrahydro-2H-pyran-4-yl)methoxy)isonicotinic acid (intermediate 5) | 519.3 $(M + H)^+$ |
| 2.25 | ((3aS,6aS)-5-(2-(dimethylamino)-6-((tetrahydro-2H-pyran-4-yl)methoxy)isonicotinoyl)hexahydropyrrolo[3,4-c]pyrrol-2(1H)-yl)((R)-4,5,6,7-tetrahydro-1H-benzo[d][1,2,3]triazol-5-yl)methanone 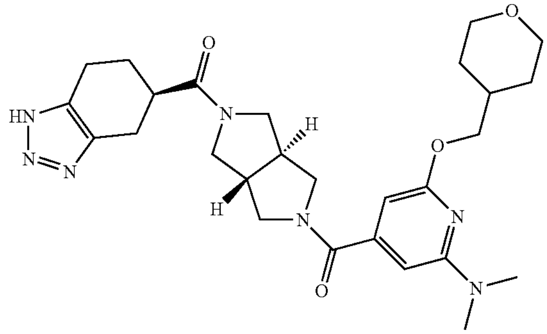 | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.1)/2-(dimethylamino)-6-((tetrahydro-2H-pyran-4-yl)methoxy)isonicotinic acid (intermediate 11) | 524.4 $(M + H)^+$ |

-continued

| Ex. | Systematic Name | Amine/Carboxylic acid | MS, m/e |
|---|---|---|---|
| 2.26 | ((3aS,6aS)-5-(1H-benzo[d][1,2,3]triazole-5-carbonyl)hexahydropyrrolo[3,4-c]pyrrol-2(1H)-yl)(2-cyclopropyl-6-((tetrahydro-2H-pyran-4-yl)methoxy)pyridin-4-yl)methanone 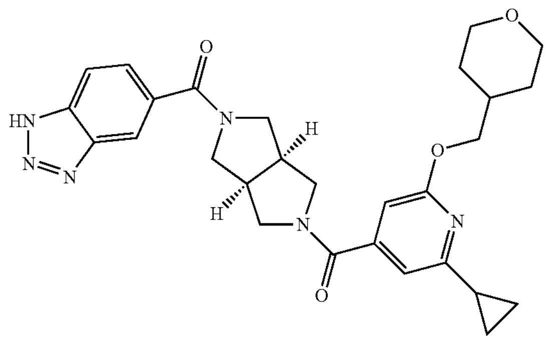 | (1H-benzo[d][1,2,3]triazol-5-yl)((3aR,6aS)-hexahydropyrrolo[3,4-c]pyrrol-2(1H)-yl)methanone hydrochloride (intermediate 2.5)/2-cyclopropyl-6-((tetrahydro-2H-pyran-4-yl)methoxy)isonicotinic acid (intermediate 5) | 517.4 $(M + H)^+$ |
| 2.27 | 4-((3aR,6aS)-5-(2-cyclopropyl-6-((tetrahydro-2H-pyran-4-yl)methoxy)isonicotinoyl) octahydropyrrolo[3,4-c]pyrrole-2-carbonyl)benezenesulfonamide 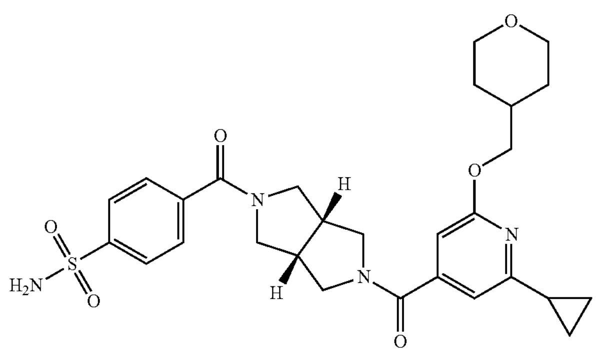 | 4-((3aR,6aS)-octahydropyrrolo[3,4-c]pyrrole-2-carbonyl)benzenesulonamide hydrochloride (intermediate 2)/ 2-cyclopropyl-6-((tetrahydro-2H-pyran-4-yl)methoxy)isonicotinic acid (intermediate 5) | 555.3 $(M + H)^+$ |
| 2.28 | ((3aR,8aS)-6-(3-cyclopropyl-5-((tetrahydro-2H-pyran-4-yl)methoxy)benzoyl)octahydropyrrolo[3,4-d]azepin-2(1H)-yl)((R)-4,5,6,7-tetrahydro-1H-benzo[d][1,2,3]triazol-5-yl)methanone 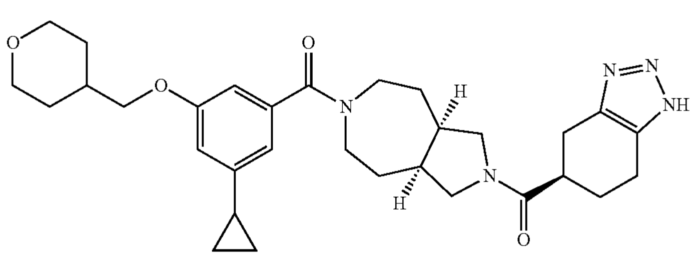 | ((3aR,8aS)-octahydropyrrolo[3,4-d]azepin-2(1H)-yl)((R)-4,5,6,7-tetrahydro-1H-benzo[d][1,2,3]triazol-5-yl)methanone (intermediate 15)/ 3-cyclopropyl-5-(oxan-4-ylmethoxy)benzoic acid (intermediate 9.1) | 548.4 $(M + H)^+$ |

-continued

| Ex. | Systematic Name | Amine/Carboxylic acid | MS, m/e |
|---|---|---|---|
| 2.29 | ((3aS,6aS)-5-(1H-benzo[d][1,2,3]triazole-5-carbonyl)hexahydropyrrolo[3,4-c]pyrrol-2(1H)-yl)(3-cyclopropyl-5-((tetrahydro-2H-pyran-4-yl)methoxy)phenyl)methanone 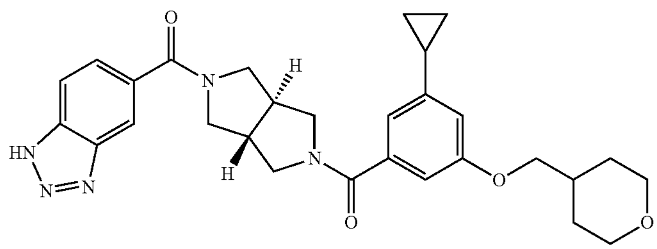 | (1H-benzo[d][1,2,3]triazol-5-yl)((3aR,6aR)-hexahydropyrrolo[3,4-c]pyrrol-2(1H)-yl)methanone dihydrochloride (intermediate 2.2)/3-cyclopropyl-5-(oxan-4-ylmethoxy(benzoic acid (intermediate 9.1) | 516.3 $(M + H)^+$ |
| 2.30 | 6-((3aR,6aR)-5-(3-cyclopropyl-5-((tetrahydro-2H-pyran-4-yl)methoxy)benzoyl)octahydropyrrolo[3,4-c]pyrrole-2-carbonyl)pyridine-3-sulfonamide 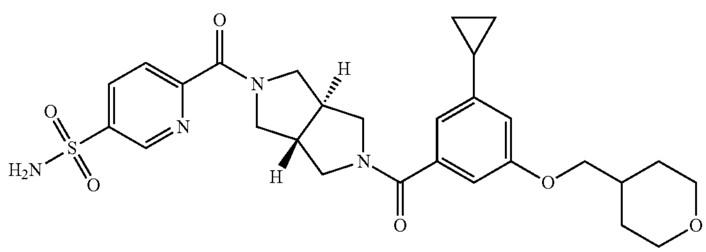 | 6-((3aR,6aR)-octahydropyrrolo[3,4-c]pyrrole-2-carbonyl)pyridine-3-sulfonamide hydrochloride (intermediate 2.3)/3-cyclopropyl-5-(oxan-4-ylmethoxy)benzoic acid (intermediate 9.1) | 555.3 $(M + H)^+$ |

Example 3

6-((3aS,6aS)-5-(5-Cyclopropyl-6-(tetrahydro-2H-pyran-4-yloxy)nicotinoyl)octahydropyrrolo[3,4-c]pyrrole-2-carbonyl)benzo[d]oxazol-2(3H)-one

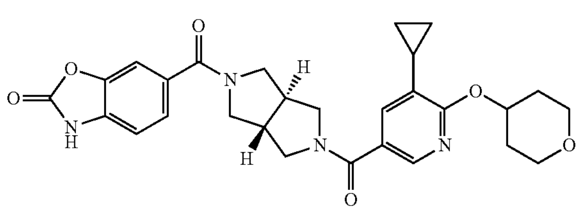 [SMILES: O=C(c1cnc(OC2CCOCC2)c(C2CC2)c1)N1C[C@@H]2CN(C(=O)c3ccc4[nH]c(=O)oc4c3)C[C@H]2C1]

To a solution of (5-cyclopropyl-6-(tetrahydro-2H-pyran-4-yloxy)pyridin-3-yl)((3aS,6aS)-hexahydropyrrolo[3,4-c]pyrrol-2(1H)-yl)methanone hydrochloride (intermediate 1; 50 mg, 119 mol) in N,N-dimethylformamide (3 mL) were added 4-methylmorpholine (60.3 mg, 597 mol), 4-amino-3-hydroxybenzoic acid (CAS 2374-03-0; 18.3 mg, 119 µmol) and O-(7-azabenzotriazol-1-yl)-N,N,N',N'-tetramethyluronium hexafluoro-phosphate (45.4 mg, 119 mol) at 0° C. After the addition the reaction mixture was let warm up to ambient temperature and stirred overnight for 18 h, then 1,1'-carbonyldiimidazole (42.6 mg, 262 mol) was added, then after 72 h the reaction mixture was partitioned between sat. aq. ammonium chloride solution and ethyl acetate. The organic layer was washed with brine, dried over magnesium sulfate, filtered and evaporated. Chromatography (silica gel, gradient dichloromethane to dichloromethane/methanol/25% aq. ammonia solution 90:10:0.25) produced the title compound (22 mg, 36%). Light brown solid, MS: 519.3 $(M+H)^+$.

The following examples were prepared according to example 3, replacing (5-cyclopropyl-6-(tetrahydro-2H-pyran-4-yloxy)pyridin-3-yl)((3aS,6aS)-hexahydropyrrolo[3,4-c]pyrrol-2(1H)-yl)methanone hydrochloride by the appropriate amine.

| Ex. | Systematic Name | Amine | MS, m/e |
|---|---|---|---|
| 3.01 | 6-((3aS,6aS)-5-2-cyclopropyl-6-((tetrahydro-2H-pyran-4-yl)methoxy)isonicotinoyl)octahydropyrrolo[3,4-c]pyrrole-2-carbonyl)benzo[d]oxazol-2(3H)-one 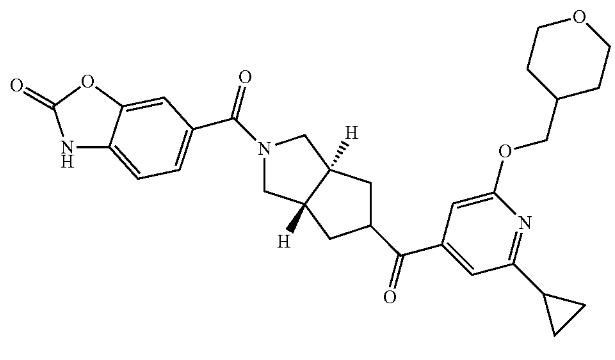 | (2-cyclopropyl-6-((tetrahydro-2H-pyran-4-yl)methoxy pyridin-4-yl)((3aS,6aS)-hexahydropyrrolo[3,4-c]pyrrol-2(1H)-yl)methanone hydrochloride (intermediate 1.1) | 533.3 M + H)+ |
| 3.02 | 6-((3aR,8aS)-6-(2-cyclopropyl-6-((tetrahydro-2H-pyran-4-yl)methoxy)isonicotinoyl)decahydropyrrolo[3,4-d]azepine-2-carbonyl)benzo[d]oxazol-2(3H)-one 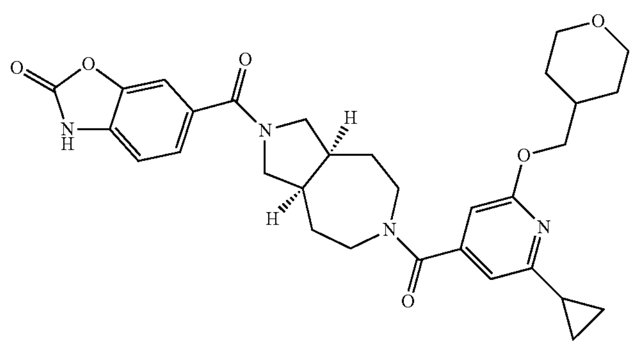 | (2-cyclopropyl-6-((tetrahydro-2H-pyran-4-yl)methoxy)pyridin-4-yl)((3aR,8aS)-octahydropyrrolo[3,4-d]azepin-6(7H)-yl)methanone hydrochloride (intermediate 1.2) | 561.3 M + H)+ |

Example 4

6-(((3aS,6aS)-5-(5-Cyclopropyl-6-(tetrahydro-2H-pyran-4-yloxy)nicotinoyl)hexahydropyrrolo[3,4-c]pyrrol-2(1H)-yl)methyl)benzo[d]oxazol-2(3H)-one

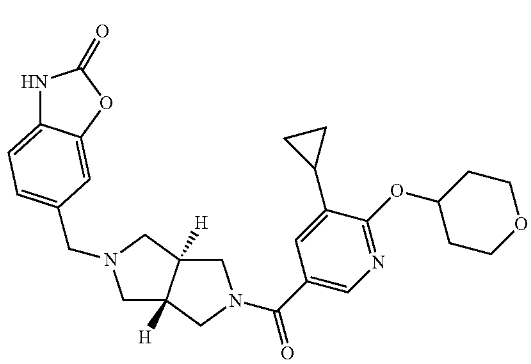 [SMILES: O=C(c1cnc(OC2CCOCC2)c(C2CC2)c1)N1C[C@@H]2CN(Cc3ccc4[nH]c(=O)oc4c3)C[C@H]2C1]

To a solution of (5-cyclopropyl-6-(tetrahydro-2H-pyran-4-yloxy)pyridin-3-yl)((3aS,6aS)-hexahydropyrrolo[3,4-c]pyrrol-2(1H)-yl)methanone hydrochloride (intermediate 1; 30 mg, 76 μmol) in dichloromethane (1 mL) were added 4-methylmorpholine (7.7 mg, 8.4 μmol), 2-oxo-2,3-dihydrobenzo[d]oxazole-6-carbaldehyde (CAS-RN 54903-15-0; 14.9 mg, 91 mol), sodium triacetoxyborohydride (21.6 mg, 99 μmol) and acetic acid (9.1 mg, 0.15 mmol). The white suspension was stirred at room temperature for 16 h, then the reaction mixture was partitioned between ice/sat. aq. sodium hydrogencarbonate solution and ethyl acetate. The organic layer was washed with brine, dried over magnesium sulfate, filtered and evaporated. Chromatography (silica gel, gradient dichloromethane to dichloromethane/methanol/25% aq. ammonia solution 90:10:0.25) produced the title compound (20 mg, 52%). White solid, MS: 505.3 $(M+H)^+$.

The following example was prepared according to example 4, replacing 2-oxo-2,3-dihydrobenzo[d]oxazole-6-carbaldehyde by the appropriate aldehyde.

| Ex. | Systematic Name | Aldehyde | MS, m/e |
|---|---|---|---|
| 4.01 | ((3aS,6aS)-5-((1H-benzo[d][1,2,3]triazol-5-yl)methyl)hexahydropyrrolo[3,4-c]pyrrol-2(1H)-yl)(5-cyclopropyl-6-(tetrahydro-2H-pyran-4-yloxy)pyridin-3-yl)methanone | tert-butyl 5-formyl-1H-benzo[d][1,2,3]triazole-1-carboxylate (CAS-RN 354587-73-8) | 489.4 (M + H)+ |
| | 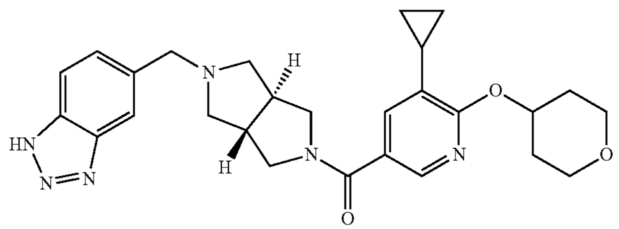 | | |

Example 5

((3aR,6aR)-5-(2-Cyclopropyl-6-((tetrahydro-2H-pyran-4-yl)methoxy)isonicotinoyl)-hexahydropyrrolo[3,4-c]pyrrol-2(1H)-yl)(6,7-dihydro-1H-[1,2,3]triazolo[4,5-c]pyridin-5(4H)-yl)methanone

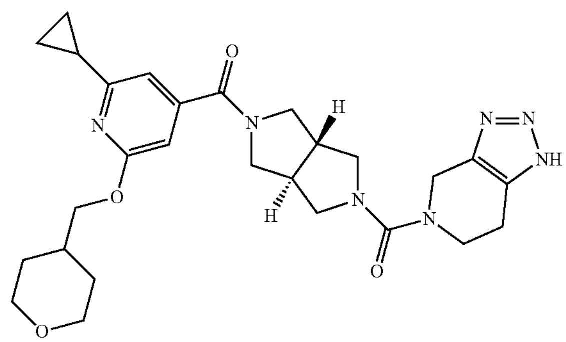 [SMILES: O=C(c1cc(OCC2CCOCC2)nc(C2CC2)c1)N1C[C@@H]2CN(C(=O)N3CCc4[nH]nnc4C3)C[C@H]2C1]

To a stirring suspension of 4,5,6,7-tetrahydro-1H-[1,2,3]triazolo[4,5-c]pyridine (CAS-RN 706757-05-3; 13.4 mg, 108 μmol) in dichloromethane (2 mL) and N,N-diisopropylethylamine (CAS-RN 7087-68-5; 27.8 mg, 215 mol) was added a solution of (3aR,6aR)-5-(2-cyclopropyl-6-((tetrahydro-2H-pyran-4-yl)methoxy)isonicotinoyl)hexahydropyrrolo[3,4-c]pyrrole-2(1H)-carbonyl chloride (intermediate 13; 55 mg, 108 μmol) in dichloromethane (2 mL). After stirring the fine suspension for 1 h at ambient temperature N,N-dimethylformamide (1.5 mL) was added. The reaction mixture was stirred for 16 h, then partitioned between ice/sat. ammonium chloride solution/dichloromethane. The organic layer was washed with brine, dried over magnesium sulfate, filtered and evaporated. Chromatography (silica gel, gradient dichloromethane to dichloromethane/methanol/25% aq. ammonia solution 90:10:0.25) produced the title compound (41 mg, 73%). White solid, MS: 522.6 (M+H)+.

The following examples were prepared according to example 5, replacing (3aR,6aR)-5-(2-cyclopropyl-6-((tetrahydro-2H-pyran-4-yl)methoxy)isonicotinoyl)hexahydropyrrolo[3,4-c]pyrrole-2(1H)-carbonyl chloride by the appropriate carbamoyl chloride and 4,5,6,7-tetrahydro-1H-[1,2,3]triazolo[4,5-c]pyridine by the appropriate amine.

| Ex. | Systematic Name | Carbamoyl chloride/Amine | MS, m/e |
|---|---|---|---|
| 5.01 | 1-((3aR,6aR)-5-(2-cyclopropyl-6-((tetrahydro-2H-pyran-4-yl)methoxy)isonicotinoyl)octahydropyrrolo[3,4-c]pyrrole-2-carbonyl)piperidine-4-sulfonamide 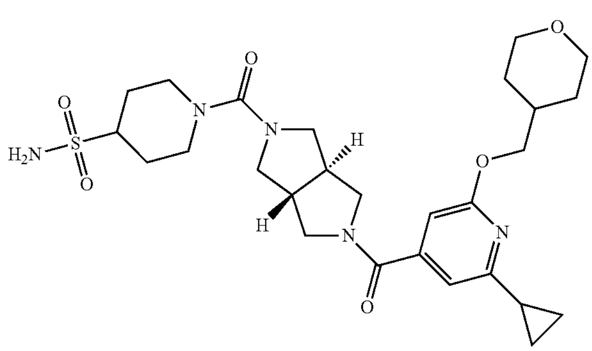 | (3aR,6aR)-5-(2-cyclopropyl-6-((tetrahydro-2H-pyran-4-yl)methoxy)isonicotinoyl)hexahydropyrrolo[3,4-c]pyrrole-2(1H)-carbonyl chloride (intermediate 13)/piperidine-4-sulfonamide (CAS-RN 878388-34-2) | 562.6 (M + H)+ |

-continued

| Ex. | Systematic Name | Carbamoyl chloride/Amine | MS, m/e |
|---|---|---|---|
| 5.02 | ((3aR,8aS)-6-(2-cyclopropyl-6-((tetrahydro-2H-pyran-4-yl)methoxy)isonicotinoyl)-octahydropyrrolo[3,4-d]azepin-2(1H)-yl)(6,7-dihydro-1H-[1,2,3]triazolo[4,5-c]pyridin-5(4H)-yl)methanone 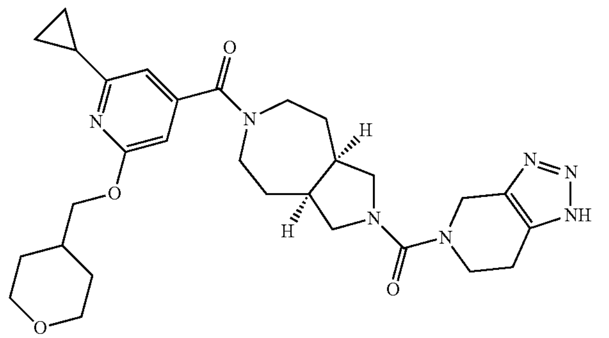 | (3aR,8aS)-6-[2-cyclopropyl-6-(oxan-4-ylmethoxy)pyridine-4-carbonyl]-1,3,3a,4,5,7,8,8a-octahydropyrrolo[3,4-d]azepine-2-carbonyl chloride (intermediate 13.1)/4,5,6,7-tetrahydro-1H-[1,2,3]triazolo[4,5-c]pyridine (CAS-RN 706757-05-3) | 550.3 (M + H)+ |
| 5.03 | ((3aR,8aS)-6-(2-cyclopropyl-6-((tetrahydro-2H-pyran-4-yl)methoxy)isonicotinoyl)-octahydropyrrolo[3,4-d]azepin-2(1H)-yl)(3-hydroxy-4,5-dihydroisoxazolo[5,4-c]pyridin-6(7H)-yl)methanone 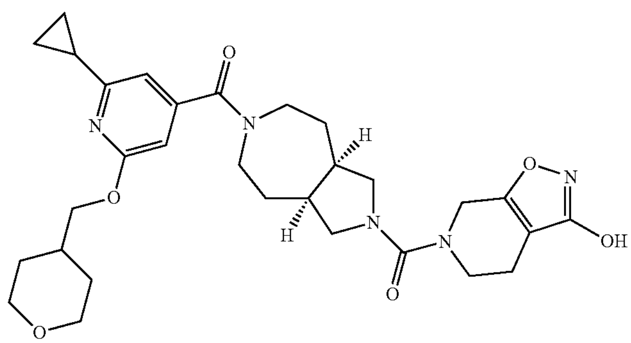 | (3aR,8aS)-6-[2-cyclopropyl-6-(oxan-4-ylmethoxy)pyridine-4-carbonyl]-l,3,3a,4,5,7,8,8a-octahydropyrrolo[3,4-d]azepine-2-carbonyl chloride (intermediate 13.1)/4,5,6,7-tetrahydro-[1,2]oxazolo[5,4-c]pyridin-3-ol (CAS-RN 881493-60-3) | 566.3 (M + H)+ |
| 5.04 | ((3aR,8aS)-N-((1H-1,2,3-triazol-4-yl)-methyl)-6-(2-cyclopropyl-6-((tetrahydro-2H-pyran-4-yl)methoxy)isonicotinoyl)octa-hydropyrrolo[3,4-d]azepine-2(1H)-carboxamide 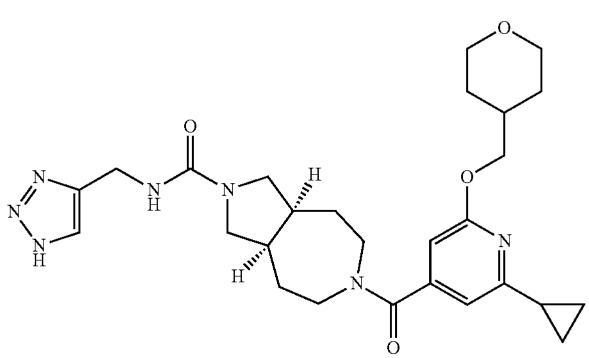 | (3aR,8aS)-6-[2-cyclopropyl-6-(oxan-4-ylmethoxy)pyridine-4-carbonyl]-1,3,3a,4,5,7,8,8a-octahydropyrrolo[3,4-d]azepine-2-carbonyl chloride (intermediate 13.1)/1H-triazol-4-ylmethanamine hydrochloride (CAS-RN 1009101-70-5) | 524.3 (M + H)+ |

-continued

| Ex. | Systematic Name | Carbamoyl chloride/Amine | MS, m/e |
|---|---|---|---|
| 5.05 | ((3aR,8aS)-6-(2-cyclopropyl-6-((tetrahydro-2H-pyran-4-yl)methoxy)isonicotinoyl)-N-((3-hydroxyisoxazol-5-yl)methyl)octahydropyrrolo[3,4-d]azepine-2(1H)-carboxamide 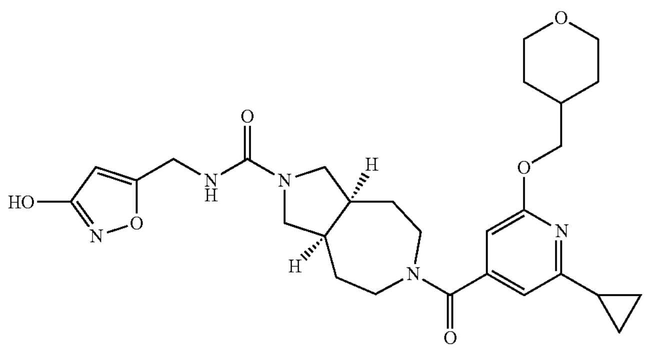 | (3aR,8aS)-6-[2-cyclopropyl-6-(oxan-4-ylmethoxy)pyridine-4-carbonyl]-1,3,3a,4,5,7,8,8a-octahydropyrrolo[3,4-d]azepine-2-carbonyl chloride (intermediate 13.1)/5-(aminomethyl)-1,2-oxazol-3-ol (CAS-RN 2763-96-4) | 540.3 (M + H)$^+$ |

Example 6

((3aR,8aS)-6-(2-Cyclopropyl-6-((tetrahydro-2H-pyran-4-yl)methoxy)isonicotinoyl)octahydropyrrolo[3,4-d]azepin-2(1H)-yl)((S)-4,5,6,7-tetrahydro-1H-benzo[d][1,2,3]triazol-5-yl)methanone

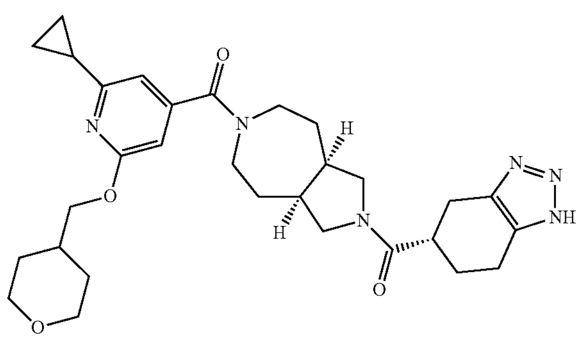 [SMILES: O=C(c1cc(OCC2CCOCC2)nc(C2CC2)c1)N1CC[C@@H]2CN(C(=O)[C@H]3CCc4[nH]nnc4C3)C[C@@H]2CC1]

Racemic ((3aR,8aS)-6-(2-cyclopropyl-6-((tetrahydro-2H-pyran-4-yl)methoxy)isonicotinoyl)octahydropyrrolo[3,4-d]azepin-2(1H)-yl)(4, 5,6,7-tetrahydro-1H-benzo[d][1,2,3]triazol-5-yl)methanone (example 1.10; 655 mg, 1.19 mmol) was separated by preparative HPLC using a Chiralpak AD column as the stationary phase and heptane/2-propanol 3:2 as the mobile phase. This produced the faster eluting (+)-(R)-enantiomer (example 2.21; 69 mg, 41%), followed by the slower eluting (−)-(S)-enantiomer (example 6; 291 mg, 44%). White foam, MS: 549.4 (M+H)$^+$.

Example 7

1H-Triazol-4-ylmethyl (3aS,8aR)-6-[2-cyclopropyl-6-(oxan-4-ylmethoxy)pyridine-4-carbonyl]-1,3,3a,4,5,7,8,8a-octahydropyrrolo[3,4-d]azepine-2-carboxylate

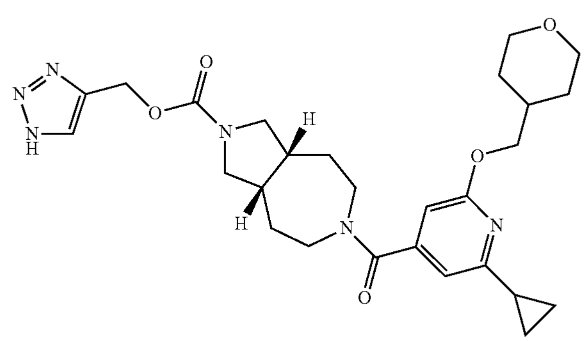 [SMILES: O=C(OCc1c[nH]nn1)N1C[C@H]2CCN(C(=O)c3cc(OCC4CCOCC4)nc(C4CC4)c3)CC[C@H]2C1]

To a solution of (1-trityl-1H-1,2,3-triazol-4-yl)methanol (CAS-RN 88529-86-6; 50 mg, 146 μmol) in acetonitrile (3 mL) was added 1,1'-carbonyldiimidazole (23.7 mg, 146 mol). The reaction was stirred at 50° C. for 1.5 h, then triethylamine (74.1 mg, 732 mol) and (2-cyclopropyl-6-((tetrahydro-2H-pyran-4-yl)methoxy)pyridin-4-yl)((3aR, 8aS)-octahydropyrrolo[3,4-d]azepin-6(2H)-yl)methanone (intermediate 1.2; 65.7 mg, 146 μmol) were added and the reaction mixture was heated to reflux and stirred for 48 h. The mixture was let cool down to ambient temperature and trifluoroacetic acid (334 mg, 2.93 mmol) was added. The reaction was stirred for 1 h at ambient temperature. The reaction mixture was directly evaporated and the residue was combined with 1 M aq. sodium hydroxide solution and ethyl acetate, poured onto sat. ammonium chloride solution and then extracted. The organic layer was washed with brine, dried over magnesium sulfate, filtered and evaporated. Chromatography (silica gel, gradient dichloromethane to dichloromethane/methanol/25% aq. ammonia solution 90:10:0.25) produced the title compound (35 mg, 46%). White solid, MS: 525.3 $(M+H)^+$.

INTERMEDIATES

Intermediate 1

(5-Cyclopropyl-6-(tetrahydro-2H-pyran-4-yloxy)pyridin-3-yl)((3aS,6aS)-hexahydropyrrolo[3,4-c]pyrrol-2(1H)-yl)methanone hydrochloride Step 1: (3aR,6aR)-tert-butyl 5-(5-cyclopropyl-6-(tetrahydro-2H-pyran-4-yloxy)nicotinoyl)hexahydropyrrolo[3,4-c]pyrrole-2(1H)-carboxylate The title compound was produced in analogy to example 2, replacing 4-((3aR,6aS)-octahydropyrrolo[3,4-c]pyrrole-2-carbonyl)benzenesulfonamide hydrochloride by (3aR,6aR)-tert-butyl hexahydropyrrolo[3,4-c]pyrrole-2(1H)-carboxylate (intermediate 3.1). White foam, MS: 458.3 $(M+H)^+$.

Step 2: (5-Cyclopropyl-6-(tetrahydro-2H-pyran-4-yloxy)pyridin-3-yl)((3aS,6aS)-hexahydropyrrolo[3,4-c]pyrrol-2(1H)-yl)methanone hydrochloride A colourless solution of (3aR,6aR)-tert-butyl 5-(5-cyclopropyl-6-(tetrahydro-2H-pyran-4-yloxy)nicotinoyl)hexahydropyrrolo[3,4-c]pyrrole-2(1H)-carboxylate (332 mg, 726 mol) in hydrogen chloride solution (5-6 M in 2-propanol, 3.2 mL) was stirred at room temperature for 4 h, then the reaction mixture was concentrated in vacuo to produce the title compound (303 mg, quant.). White foam, MS: 358.2 $(M+H)^+$.

The following intermediates were prepared according to intermediate 1, replacing (3aR,6aR)-tert-butyl hexahydropyrrolo[3,4-c]pyrrole-2(1H)-carboxylate by the appropriate amine and 5-cyclopropyl-6-(tetrahydro-2H-pyran-4-yloxy)nicotinic acid by the appropriate carboxylic acid

Intermediate 2

4-((3aR,6aS)-Octahydropyrrolo[3,4-c]pyrrole-2-carbonyl)benzenesulfonamide hydrochloride Step 1: (3aR,6aS)-tert-Butyl 5-(4-sulfamoylbenzoyl)hexahydropyrrolo[3,4-c]pyrrole-2(1H)-carboxylate To a colourless solution of (3aR,6aS)-tert-butyl hexahydropyrrolo[3,4-c]pyrrole-2(1H)-carboxylate (CAS-RN 250275-15-1; 1.00 g, 4.48 mmol), 4-methylmorpholine (1.36 g, 13.4 mmol) and 4-sulfamoylbenzoic acid (900 mg, 4.48 mmol) in N,N-dimethylformamide (75 mL) was added O-(7-azabenzotriazol-1-yl)-N,N,N',N'-tetramethyluronium hexafluoro-phosphate (1.70 g, 4.48 mmol) at room temperature, then after 16 h the reaction mixture was partitioned between sat. aq. ammonium chloride solution and ethyl acetate/2-methyltetrahydrofuran. The organic layer was washed with brine, dried over magnesium sulfate, filtered and evaporated. The residue was triturated in ethyl acetate/heptane 1:1 to produce the title compound (1.46 g, 82%). White solid, MS: 394.5 $(M-H)^-$.

Step 2: 4-((3aR,6aS)-Octahydropyrrolo[3,4-c]pyrrole-2-carbonyl)benzenesulfonamide hydrochloride To a white suspension of (3aR,6aS)-tert-butyl 5-(4-sulfamoylbenzoyl)hexahydropyrrolo[3,4-c]pyrrole-2(1H)-carboxylate (1.44 g, 3.64 mmol) in 2-propanol (10 mL) was added hydrogen chloride solution (5-6 M in 2-propanol, 20 mL). The suspension was stirred at room temperature for 3 h and then concentrated in vacuo. The residue was triturated in ethyl acetate to produce the title compound (1.24 g, 98%). White solid, MS: 296.4 $(M+H)^+$.

The following intermediates were prepared according to intermediate 2, replacing (3aR,6aS)-tert-butyl hexahydropyrrolo[3,4-c]pyrrole-2(1H)-carboxylate by the appropriate amine and 4-sulfamoylbenzoic acid by the appropriate carboxylic acid.

| No. | Systematic Name | Amine/Carboxylic acid | MS, m/e |
|---|---|---|---|
| 1.1 | (2-cyclopropyl-6-((tetrahydro-2H-pyran-4-yl)methoxy)pyridin-4-yl)((3aS,6aS)-hexahydropyrrolo[3,4-c]pyrrol-2(1H)-yl)methanone hydrochloride | (3aR,6aR)-tert-butyl hexahydropyrrolo[3,4-c]pyrrole-2(1H)-carboxylate (intermediate 3.1)/2-cyclopropyl-6-((tetrahydro-2H-pyran-4-yl)methoxy)isonicotinic acid (intermediate 5) | 372.2 $(M + H)^+$ |
| 1.2 | (2-cyclopropyl-6-((tetrahydro-2H-pyran-4-yl)methoxy)pyridin-4-yl)((3aR,8aS)-octahydropyrrolo[3,4-d]azepin-6(7H)-yl)methanone hydrochloride | tert-butyl (3aS,8aR)-3,3a,4,5,6,7,8,8a-octahydro-1H-pyrrolo[3,4-d]azepine-2-carboxylate (CAS-RN 1251013-07-6)/2-cyclopropyl-6-((tetrahydro-2H-pyran-4-yl)methoxy)isonicotinic acid (intermediate 5) | 400.3 $(M + H)^+$ |

| No. | Systematic Name | Amine/Carboxylic acid | MS, m/e |
|---|---|---|---|
| 2.1 | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride | (3aS,6aS)-tert-butyl hexahydropyrrolo[3,4-c]pyrrole-2(1H)-carboxylate (intermediate 3)/(+)-(R)-4,5,6,7-tetrahydro-1H-benzo[d][1,2,3]triazole-5-carboxylic acid (intermediate 4) | 262.6 $(M + H)^+$ |
| 2.2 | (1H-benzo[d][1,2,3]triazol-5-yl)((3aR,6aR)-hexahydropyrrolo[3,4-c]pyrrol-2(1H)-yl)methanone dihydrochloride | (3aS,6aS)-tert-butyl hexahydropyrrolo[3,4-c]pyrrole-2(1H)-carboxylate (intermediate 3)/1H-benzo[d]-[1,2,3]triazole-5-carboxylic acid (CAS-RN 23814-12-2) | 258.5 $(M + H)^+$ |
| 2.3 | 6-((3aR,6aR)-octahydropyrrolo[3,4-c]pyrrole-2-carbonyl)pyridine-3-sulfonamide hydrochloride | (3aS,6aS)-tert-butyl hexahydropyrrolo[3,4-c]pyrrole-2(1H)-carboxylate (intermediate 3)/5-sulfamoylpicolinic acid (CAS-RN 1308677-67-9) | 297.1 $(M + H)^+$ |
| 2.4 | (1H-benzo[d][1,2,3]triazol-5-yl)((3aR,8aS)-octahydropyrrolo[3,4-d]azepin-6(7H)-yl)methanone hydrochloride | (3aR,8aS)-tert-butyl octahydropyrrolo[3,4-d]azepine-2(1H)-carboxylate hydrochloride (CAS-RN 1251013-07-6)/1H-benzo[d][1,2,3]triazole-5-carboxylic acid (CAS-RN 23814-12-2) | 286.5 $(M + H)^+$ |
| 2.5 | (1H-benzo[d][1,2,3]triazol-5-yl)((3aR,6aS)-hexahydropyrrolo[3,4-c]pyrrol-2(1H)-yl)methanone hydrochloride | (3aR,6aS)-tert-butyl hexahydropyrrolo[3,4-c]pyrrole-2(1H)-carboxylate (CAS-RN 250275-15-1)/1H-benzo[d][1,2,3]triazole-5-carboxylic acid (CAS-RN 23814-12-2) | 258.5 $(M + H)^+$ |

Intermediate 3

(3aS,6aS)-tert-Butyl hexahydropyrrolo[3,4-c]pyrrole-2(1H)-carboxylate

Step 1: (3R,4R)-tert-Butyl 3,4-bis((methylsulfonyloxy)methyl)pyrrolidine-1-carboxylate To a solution of (3R,4R)-tert-butyl 3,4-bis(hydroxymethyl)pyrrolidine-1-carboxylate (CAS-RN 895245-32-6; 2.97 g, 12.8 mmol) and N,N-diisopropylethylamine (9.96 g, 77.0 mmol) in dichloromethane (70 mL) was added a solution of methanesulfonyl chloride (4.41 g, 38.5 mmol) in dichloromethane (5 mL) dropwise at 0° C., then after 1 h the reaction mixture was treated with sat. aq. ammonium chloride solution and extracted with ethyl acetate. The organic layer was washed with sat. aq. sodium hydrogencarbonate solution and brine, dried over magnesium sulfate, filtered, and evaporated. Chromatography (silica gel; heptane-ethyl acetate gradient) produced the title compound (4.22 g, 85%). Light yellow oil, MS: 332.4 $(M\text{-isobutene}+H)^+$.

Step 2: (3aS,6aS)-tert-Butyl 5-benzylhexahydropyrrolo[3,4-c]pyrrole-2(1H)-carboxylate To a solution of (3R,4R)-tert-butyl 3,4-bis((methylsulfonyloxy)methyl)pyrrolidine-1-carboxylate (4.22 g, 10.9 mmol) in acetonitrile (100 mL) was added potassium carbonate (15.1 g, 109 mmol) and phenylmethanamine (3.5 g, 32.7 mmol). The reaction mixture was heated at 95° C. for 45 h, then cooled to room temperature and partitioned between ethyl acetate and water. The organic layer was washed with sat. aq. ammonium chloride solution, sat. aq. sodium hydrogencarbonate solution, and brine, dried over magnesium sulfate, filtered, and evaporated. Chromatography (silica gel; ethyl acetate-methanol gradient) produced the title compound (2.23 g, 68%). Light yellow solid, MS: 303.5 $(M+H)^+$.

Step 3: (3aS,6aS)-tert-Butyl hexahydropyrrolo[3,4-c]pyrrole-2(1H)-carboxylate

To a solution of (3aS,6aS)-tert-butyl 5-benzylhexahydropyrrolo[3,4-c]pyrrole-2(1H)-carboxylate (2.22 g, 7.34 mmol) in methanol (20 mL) was added palladium (10% on carbon, 220 mg, 7.34 mmol), and the reaction mixture was stirred under a hydrogen atmosphere (1 bar) at room temperature for 24 h, then insoluble material was removed by filtration through diatomaceous earth. The filtrate was concentrated to produce the title compound (1.60 g, 100%). White waxy solid, MS: 213.5 $(M+H)^+$.

Intermediate 3.1

(3aR,6aR)-tert-Butyl hexahydropyrrolo[3,4-c]pyrrole-2(1H)-carboxylate

The title compound was produced in analogy to intermediate 3, replacing (3R,4R)-tert-butyl 3,4-bis(hydroxymethyl)pyrrolidine-1-carboxylate by (3S,4S)-tert-butyl 3,4-bis(hydroxymethyl)pyrrolidine-1-carboxylate (CAS-RN 895245-30-4). White waxy solid, MS: 213.3 $(M+H)^+$.

Intermediate 4

(+)-(R)-4,5,6,7-Tetrahydro-1H-benzo[d][1,2,3]triazole-5-carboxylic acid

Racemic 4,5,6,7-tetrahydro-1H-benzo[d][1,2,3]triazole-5-carboxylic acid (CAS-RN 33062-47-4; 1.10 g, 6.58 mmol) was separated by preparative HPLC using a Chiralpak AD column as the stationary phase and heptane/ethanol 3:2 as the mobile phase. This produced the faster eluting (+)-(R)-enantiomer (452 mg, 41%), followed by the slower eluting (−)-(S)-enantiomer (381 mg, 35%). White solid, MS: 166.2 $(M-H)^-$.

Intermediate 5

2-Cyclopropyl-6-((tetrahydro-2H-pyran-4-yl) methoxy)isonicotinic acid

Step 1: Methyl 6-cyclopropyl-2-oxo-1,2-dihydro-pyridine-4-carboxylate

A suspension of 6-cyclopropyl-2-oxo-1,2-dihydropyridine-4-carboxylic acid (CAS-RN 150190-28-6; 400 mg, 2.23 mmol) in methanol (4 mL) and sulfuric acid (12 μL) was added was heated at 70° C. for 48 h, then concentrated in vacuo. The residue was suspended in dichloromethane (10 mL), then insoluble material was removed by filtration and the filtrate evaporated to produce the title compound (427 mg, 99%). Light brown semisolid, MS: 194.1 $(M+H)^+$.

Step 2: Methyl 2-cyclopropyl-6-((tetrahydro-2H-pyran-4-yl)methoxy)isonicotinate

To a stirring suspension of methyl 6-cyclopropyl-2-oxo-1,2-dihydropyridine-4-carboxylate (212 mg, 1.1 mmol) in acetonitrile (5 mL) were added potassium carbonate (455 mg, 3.29 mmol) and 4-(iodomethyl)tetrahydro-2H-pyran (CAS-RN 101691-94-5; 744 mg, 3.29 mmol). The reaction mixture was heated at 80° C. for 16 h and then evaporated in vacuo. The residue was purified by chromatography (silica gel; heptane-ethyl acetate gradient) to produce the title compound (188 mg, 59%). Colourless oil, MS: 292.2 $(M+H)^+$.

Step 3: 2-Cyclopropyl-6-((tetrahydro-2H-pyran-4-yl)methoxy)isonicotinic acid

To a solution of methyl 2-cyclopropyl-6-((tetrahydro-2H-pyran-4-yl)methoxy)isonicotinate (184 mg, 632 μmol) in tetrahydrofuran (2 mL) and water (2 mL) was added lithium hydroxide monohydrate (53.0 mg, 1.26 mmol) and the resulting mixture stirred at room temperature for 16 h. The mixture was partially evaporated in order to remove the tetrahydrofuran. The aqueous phase was partitioned between 1 M aq. hydrochloric acid solution and ethyl acetate. The organic layer was washed with brine, dried over magnesium sulfate, filtered and evaporated to give the title compound (218 mg, quant.). Colourless oil, MS: 276.1 $(M-H)^-$.

Intermediate 5.1

2-cyclopropyl-6-((tetrahydro-2H-pyran-3-yl) methoxy)isonicotinic acid

The title compound was produced in analogy to intermediate 5, replacing 4-(iodomethyl)tetrahydro-2H-pyran by 3-(bromomethyl)tetrahydro-2H-pyran (CAS-RN 116131-44-3). White solid, MS: 276.2 $(M-H)^-$.

Intermediate 6

5-Cyclopropyl-6-(tetrahydrofuran-3-yloxy)nicotinic acid

Step 1: 5-Bromo-6-(tetrahydrofuran-3-yloxy)nicotinic acid

5-Bromo-6-chloronicotinic acid (200 mg, 804 mol) was combined with dimethyl sulfoxide (4 mL), powdered potassium hydroxide (135 mg, 2.41 mmol), and tetrahydrofuran-3-ol (109 mg, 1.21 mmol). The reaction mixture was stirred at 50° C. for 3 h and at room temperature for 48 h and then partitioned between 1 M aq. hydrochloric acid solution and dichloromethane. The organic layer was washed with 1 M aq. hydrochloric acid solution, dried over magnesium sulfate, filtered, and evaporated to produce the title compound (257 mg), which was directly used in the next step. Colourless oil, MS: 286.1 $(M-H)^-$.

Step 2: 5-Cyclopropyl-6-(tetrahydrofuran-3-yloxy)nicotinic acid

A solution of 5-bromo-6-(tetrahydrofuran-3-yloxy)nicotinic acid (223 mg, 697 mol), potassium cyclopropyltrifluoroborate (113 mg, 766 mol), palladium(II) acetate (3.1 mg, 13 mol) and butyl-di-1-adamantylphosphine (15 mg, 42 mol) and cesium carbonate (681 mg, 2.09 mmol) in toluene (5 mL) and water (1 mL) was purged with argon three times, then heated at reflux for 6 h. After cooling the reaction mixture was partitioned between 1 M aq. sodium hydroxide solution and dichloromethane. The aqueous layer was acidified with 1 M aq. hydrochloric acid solution and extracted with ethyl acetate. The organic layer was dried over magnesium sulfate, filtered, and evaporated. Chromatography (silica gel, gradient dichloromethane to dichloromethane/methanol/25% aq. ammonia solution 90:10:0.25) produced the title compound (104 mg, 60%). White solid, MS: 250.1 $(M+H)^+$.

The following intermediates were produced in analogy to intermediate 6, replacing tetrahydrofuran-3-ol by the appropriate alcohol:

| No. | Systematic Name | Alcohol | MS, m/e |
|---|---|---|---|
| 6.1 | 5-cyclopropyl-6-(tetrahydro-2H-pyran-4-yloxy)nicotinic acid | tetrahydro-2H-pyran-4-ol | 264.1 $(M + H)^+$ |
| 6.2 | 5-cyclopropyl-6-(tetrahydro-2H-pyran-3-yloxy)nicotinic acid | tetrahydro-2H-pyran-3-ol | 264.2 $(M + H)^+$ |

Intermediate 7

5-Cyclopropyl-6-(tetrahydro-2H-pyran-4-ylamino) nicotinic acid

Step 1: 5-Bromo-6-(tetrahydro-2H-pyran-4-ylamino)nicotinic acid

A solution of 5-bromo-6-chloronicotinic acid (200 mg, 804 mol) and tetrahydro-2H-pyran-4-amine (415 mg, 4.02 mmol) in 1-methylpyrrolidin-2-one (2 mL) was heated at 220° C. for 15 min in a sealed tube under microwave irradiation. The reaction mixture was concentrated in vacuo and purified by chromatography (silica gel, gradient dichloromethane to dichloromethane/methanol/25% aq. ammonia solution 90:10:0.25) to produce the title compound (133 mg, 50%). Off-white solid, MS: 299.0 $(M+H)^+$.

Step 2: 5-Cyclopropyl-6-(tetrahydro-2H-pyran-4-ylamino)nicotinic acid

The title compound was produced in analogy to intermediate 6, step 2 from 5-bromo-6-(tetrahydro-2H-pyran-4- ylamino)nicotinic acid and potassium cyclopropyltrifluoroborate. White solid, MS: 263.2 $(M+H)^+$.

Intermediate 8

6-(Oxetan-3-yloxy)-5-(trifluoromethyl)nicotinic acid

The title compound was produced in analogy to intermediate 6, step 1 from 6-chloro-5-(trifluoromethyl)nicotinic acid and oxetan-3-ol. Light yellow solid, MS: 262.1 $(M-H)^-$.

Intermediate 9

3-Cyclopropyl-4-(tetrahydrofuran-3-yloxy)benzoic acid

Step 1: Methyl 3-bromo-4-(tetrahydrofuran-3-yloxy)benzoate

To a suspension of methyl 3-bromo-4-hydroxybenzoate (200 mg, 848 mol) in acetonitrile (2 mL) were added potassium carbonate (234 mg, 1.7 mmol) and 3-iodotetrahydrofuran (354 mg, 1.70 mmol). The reaction mixture was heated at 80° C. for 16 h and then partitioned between ice water and ethyl acetate. The organic layer was washed with brine, dried over magnesium sulfate, filtered, and evaporated to produce the title compound (298 mg, orange oil), which was directly used in the next step.

Step 2: 3-Bromo-4-(tetrahydrofuran-3-yloxy)benzoic acid

To a solution of methyl 3-bromo-4-(tetrahydrofuran-3-yloxy)benzoate (294 mg, 840 μmol) in tetrahydrofuran (2 mL) and water (2 mL) was added lithium hydroxide monohydrate (70 mg, 1.7 mmol). The reaction mixture was stirred at room temperature for 4 h and then partially evaporated in order to remove the tetrahydrofuran. The remaining aqueous solution was acidified with 1 M hydrochloric acid solution. The precipitate was collected by filtration and dried to afford the title compound (210 mg, 87%). White solid, MS: 285.0 $(M-H)^-$.

Step 3: 3-Cyclopropyl-4-(tetrahydrofuran-3-yloxy)benzoic acid

The title compound was produced in analogy to intermediate 6, step 2 from 3-bromo-4-(tetrahydrofuran-3-yloxy) benzoic acid and potassium cyclopropyltrifluoroborate. Off-white solid, MS: 247.1 $(M-H)^-$.

Intermediate 9.1

3-Cyclopropyl-5-(oxan-4-ylmethoxy)benzoic acid

The title compound was produced in analogy to intermediate 9, replacing methyl 3-bromo-4-hydroxybenzoate by methyl 3-bromo-5-hydroxybenzoate and 3-iodotetrahydrofuran by 4-(iodomethyl)tetrahydro-2H-pyran. Light brown solid, MS: 275.3 $(M-H)^-$.

Intermediate 10

5-(((3aR,6aR)-Hexahydropyrrolo[3,4-c]pyrrol-2(1H)-yl)methyl)-1H-benzo[d][1,2,3]triazole hydrochloride Step 1: (3aS,6aS)-tert-Butyl 5-((1H-benzo[d][1,2,3]triazol-5-yl)methyl)hexahydropyrrolo[3,4-c]pyrrole-2(1H)-carboxylate To a clear solution of (3aS,6aS)-tert-butyl hexahydropyrrolo[3,4-c]pyrrole-2(1H)-carboxylate hydrochloride (intermediate 3; 356 mg, 1.43 mmol) in dichloromethane (10 mL) and N-methylmorpholine (145 mg, 1.43 mmol) was added tert-butyl 5-formyl-1H-benzo[d][1,2,3]triazole-1-carboxylate (CAS-RN 354587-73-8; 425 mg, 1.72 mmol), sodium triacetoxyborohydride (394 mg, 1.86 mmol) and acetic acid (172 mg, 2.86 mmol). The white suspension was stirred at room temperature over night for 16 h. The mixture was partitioned between ice/ethyl acetate/saturated aqueous ammonium chloride solution. The organic layer was washed with brine, dried over magnesium sulfate, filtered and evaporated. Chromatography of the residue (silica gel, gradient dichloromethane to dichloromethane/methanol/25% aq. ammonia solution 90:10:0.25) produced the title compound (247 mg, 50%). White foam, MS: 344.3 $(M+H)^+$.

Step 2: 5-(((3aR,6aR)-Hexahydropyrrolo[3,4-c]pyrrol-2(1H)-yl)methyl)-1H-benzo[d][1,2,3]triazole hydrochloride A colourless solution of (3aS,6aS)-tert-butyl 5-((1H-benzo[d][1,2,3]triazol-5-yl)methyl)hexahydropyrrolo[3,4-c]pyrrole-2(1H)-carboxylate (243 mg, 708 μmol) in hydrogen chloride solution (5-6 M in 2-propanol, 5 mL) was stirred at room temperature for 4 h, then the reaction mixture was evaporated. The residue was suspended in ethyl acetate and the precipitate collected by filtration to afford the title compound (208 mg, quant.). White solid, MS: 244.2 $(M+H)^+$.

Intermediate 11

2-(Dimethylamino)-6-((tetrahydro-2H-pyran-4-yl)methoxy)isonicotinic acid

Step 1: Methyl 6-(dimethylamino)-2-oxo-1,2-dihydropyridine-4-carboxylate

A solution of methyl 6-chloro-2-oxo-1,2-dihydropyridine-4-carboxylate (CAS-RN 6937-04-8; 100 mg, 533 μmol) and dimethylamine solution (2 M in methanol, 533 μl, 1.07 mmol) in 1-methylpyrrolidin-2-one (1 mL) was heated at 190° C. for 10 min in a sealed tube under microwave irradiation. The reaction mixture was partitioned between ice/ethyl acetate/saturated aqueous ammonium chloride solution. The organic layer was washed with brine, dried over magnesium sulfate, filtered and evaporated. Chromatography of the residue (silica gel; ethyl acetate-methanol gradient) produced the title compound (23 mg, 22%). Yellow solid, MS: 197.1 $(M+H)^+$.

Step 2: Methyl 2-(dimethylamino)-6-((tetrahydro-2H-pyran-4-yl)methoxy)isonicotinate To a stirring suspension of methyl 6-(dimethylamino)-2-oxo-1,2-dihydropyridine-4-carboxylate (54 mg, 261 μmol)

in acetonitrile (2.5 mL) were added potassium carbonate (108 mg, 784 μmol) and 4-(iodomethyl)tetrahydro-2H-pyran (183 mg, 784 mol). The reaction mixture was stirred for 16 h at 80° C. and then directly evaporated. Chromatography of the residue (silica gel; heptane-ethyl acetate gradient) produced the title compound (54 mg, 70%). Light yellow oil, MS: 295.2 $(M+H)^+$.

Step 3: 2-(Dimethylamino)-6-((tetrahydro-2H-pyran-4-yl)methoxy)isonicotinic acid To a solution of methyl 2-(dimethylamino)-6-((tetrahydro-2H-pyran-4-yl)methoxy)isonicotinate (54 mg, 183 mol) in tetrahydrofuran (1 mL) and water (1 mL) lithium hydroxide monohydrate (15.4 mg, 367 μmol) was added and the resulting mixture was stirred at room temperature for 4 h. The mixture was partially evaporated in order to remove the tetrahydrofuran. The remaining aqueous solution was acidified with 1 M aq. hydrochloric acid solution. The precipitate was collected by filtration and dried to afford the title compound (24 mg). The mother liquor was saturated with solid sodium chloride and extracted three times with ethyl acetate. The organic layer was dried over magnesium sulfate, filtered and evaporated to give another crop of the title compound (20 mg). Total yield: 44 mg (86%). White solid, MS: 279.1 $(M-H)^-$.

Intermediate 12

6-(((3aR,6aR)-Hexahydropyrrolo[3,4-c]pyrrol-2(1H)-yl)methyl)benzo[d]oxazol-2(3H)-one hydrochloride The title compound was produced in analogy to intermediate 10, replacing tert-butyl 5-formyl-1H-benzo[d][1,2,3]triazole-1-carboxylate by 2-oxo-2,3-dihydrobenzo[d]oxazole-6-carbaldehyde (CAS-RN 54903-15-0). White solid, MS: 260.1 $(M+H)^+$.

Intermediate 13

(3aR,6aR)-2-[2-Cyclopropyl-6-(oxan-4-ylmethoxy)pyridine-4-carbonyl]-1,3,3a,4,6,6a-hexahydropyrrolo[3,4-c]pyrrole-5-carbonyl chloride To a colourless solution of (2-cyclopropyl-6-((tetrahydro-2H-pyran-4-yl)methoxy)pyridin-4-yl)((3aS,6aS)-hexahydropyrrolo[3,4-c]pyrrol-2(1H)-yl)methanone hydrochloride (intermediate 1.1; 100 mg, 223 mol) and N-methylmorpholine (67.7 mg, 669 mol) in dichloromethane (2 mL) was added dropwise a solution of triphosgene (33.1 mg, 112 mol) in dichloromethane (2 mL) at 0° C. The yellow solution was stirred 30 min at 0° C. and then at room temperature for 16 h. The reaction mixture was partitioned between saturated aq. ammonium chloride solution and dichloromethane. The organic layer was dried over magnesium sulfate, filtered, and evaporated to produce the title compound (114 mg, white foam), which was directly used in the next step.

Intermediate 13.1

(3aR,8aS)-6-[2-Cyclopropyl-6-(oxan-4-ylmethoxy)pyridine-4-carbonyl]-1,3,3a,4,5,7,8,8a-octahydropyrrolo[3,4-d]azepine-2-carbonyl chloride The title compound was produced in analogy to intermediate 13, replacing (2-cyclopropyl-6-((tetrahydro-2H-pyran-4-yl)methoxy)pyridin-4-yl)((3aS,6aS)-hexahydropyrrolo[3,4-c]pyrrol-2(1H)-yl)methanone hydrochloride (intermediate 1.1) by (2-cyclopropyl-6-((tetrahydro-2H-pyran-4-yl)methoxy)pyri din-4-yl)((3aR,8aS)-octahydropyrrolo[3,4-d]azepin-6(7H)-yl)methanone hydrochloride (intermediate 1.2). Light brown foam, MS: 462.3 $(M+H)^+$.

Intermediate 14

(5-Cyclopropyl-6-((tetrahydro-2H-pyran-4-yl)methoxy)pyridin-3-yl)((3aS,6aS)-hexahydropyrrolo[3,4-c]pyrrol-2(1H)-yl)methanone hydrochloride Step 1: (3aR,6aR)-tert-Butyl 5-(6-chloro-5-cyclopropylnicotinoyl)hexahydropyrrolo[3,4-c]pyrrole-2(1H)-carboxylate To a colourless solution of (3aR,6aR)-tert-butyl hexahydropyrrolo[3,4-c]pyrrole-2(1H)-carboxylate hydrochloride (intermediate 3.1; 600 mg, 2.41 mmol), 4-methylmorpholine (1.22 g, 12.1 mmol), and 6-chloro-5-cyclopropylnicotinic acid (CAS-RN 1211588-13-4; 502 mg, 2.41 mmol) in N,N-dimethylformamide (12 mL) was added O-(7-azabenzotriazol-1-yl)-N,N,N',N'-tetramethyluronium hexafluoro-phosphate (1.01 g, 2.65 mmol) at room temperature, then after 18 h the reaction mixture was partitioned between sat. aq. ammonium chloride solution and ethyl acetate. The organic layer was washed with brine, dried over magnesium sulfate, filtered and evaporated. Chromatography of the residue (silica gel, gradient dichloromethane to dichloromethane/methanol/25% aq. ammonia solution 90:10:0.25) produced the title compound (1.02 g, quant.). Light yellow solid, MS: 392.3 $(M+H)^+$.

Step 2: (3aR,6aR)-tert-Butyl 5-(5-cyclopropyl-6-((tetrahydro-2H-pyran-4-yl)methoxy)nicotinoyl)hexahydropyrrolo[3,4-c]pyrrole-2(1H)-carboxylate (3aR,6aR)-tert-Butyl 5-(6-chloro-5-cyclopropylnicotinoyl)hexahydropyrrolo[3,4-c]pyrrole-2(1H)-carboxylate (300 mg, 712 μmol) was combined with dimethyl sulfoxide (6 mL), powdered potassium hydroxide (139 mg, 2.14 mmol), and (tetrahydro-2H-pyran-4-yl)methanol (CAS-RN 14774-37-9; 131 mg, 1.07 mmol). The reaction mixture was stirred at room temperature for 18 h, and then partitioned between ice water and ethyl acetate. The organic layer was washed with brine, dried over magnesium sulfate, filtered and evaporated. Chromatography of the residue (silica gel, gradient dichloromethane to dichloromethane/methanol/25% aq. ammonia solution 90:10:0.25) produced the title compound (340 mg, quant.). White foam, MS: 472.4 $(M+H)^+$.

Step 3: (5-Cyclopropyl-6-((tetrahydro-2H-pyran-4-yl)methoxy)pyridin-3-yl)((3aS,6aS)-hexahydropyrrolo[3,4-c]pyrrol-2(1H)-yl)methanone hydrochloride A colourless solution of (3aR,6aR)-tert-butyl 5-(5-cyclopropyl-6-((tetrahydro-2H-pyran-4-yl)methoxy)nicotinoyl)hexahydropyrrolo[3,4-c]pyrrole-2(1H)-carboxylate (336 mg, 705 mol) in hydrogen chloride solution (5-6 M in 2-propanol) (4 mL) was stirred at room temperature for 2 h, then the reaction mixture was evaporated to afford the title compound (299 mg, quant.). White foam, MS: 372.3 $(M+H)^+$.

Intermediate 15

((3aR,8aS)-Octahydropyrrolo[3,4-d]azepin-2(1H)-yl)((R)-4,5,6,7-tetrahydro-1H-benzo[d][1,2,3]triazol-5-yl)methanone Step 1: (3aR,8aS)-6-Benzyl 2-tert-butyl hexahydropyrrolo[3,4-d]azepine-2,6(1H,7H)-dicarboxylate To a solution of (3aR,8aS)-tert-butyl octahydropyrrolo[3,4-d]azepine-2(1H)-carboxylate hydrochloride (CAS-RN 1251013-07-6; 505 mg, 1.82 mmol) in acetone (5 mL) and water (5 mL) was added sodium carbonate (387 mg, 3.65 mmol). The reaction mixture was cooled to 0° C. and benzyl carbonochloridate (328 mg, 1.82 mmol) was added. After 30 min the ice bath was removed, then after 23 h the reaction mixture was partitioned between ice and ethyl acetate. The organic layer was washed with brine, dried over magnesium sulfate, filtered and evaporated. Chromatography of the residue (silica gel; heptane-ethyl acetate gradient) produced the title compound (625 mg, 91%). Light yellow oil, MS: 319.2 (M-isobutene+H)$^+$.

Step 2: (3aR,8aS)-Benzyl octahydropyrrolo[3,4-d]azepine-6(7H)-carboxylate hydrochloride A colourless solution of (3aR,8aS)-6-benzyl 2-tert-butyl hexahydropyrrolo[3,4-d]azepine-2,6(1H,7H)-dicarboxylate (605 mg, 1.62 mmol) in hydrogen chloride solution (5-6 M in 2-propanol, 5 mL) was stirred at room temperature for 20 h, then the reaction mixture was evaporated. The residue was suspended in tert-butyl methyl ether and ethyl acetate and the precipitate collected by filtration to afford the title compound (455 mg, 91%). White solid, MS: 275.1 (M+H)$^+$.

Step 3: (3aR,8aS)-Benzyl 2-((R)-4,5,6,7-tetrahydro-1H-benzo[d][1,2,3]triazole-5-carbonyl)octahydropyrrolo[3,4-d]azepine-6(7H)-carboxylate To a light brown solution of (3aR,8aS)-benzyl octahydropyrrolo[3,4-d]azepine-6(7H)-carboxylate hydrochloride (446 mg, 1.43 mmol), 4-methylmorpholine (726 mg, 7.17 mmol), and (R)-4,5,6,7-tetrahydro-1H-benzo[d][1,2,3]triazole-5-carboxylic acid (intermediate 4; 240 mg, 1.43 mmol) in N,N-dimethylformamide (8 mL) was added O-(7-azabenzotriazol-1-yl)-N,N,N',N'-tetramethyluronium hexafluorophosphate (546 mg, 1.43 mmol) at room temperature, then after 18 h the reaction mixture was partitioned between sat. aq. ammonium chloride solution and ethyl acetate. The organic layer was washed with brine, dried over magnesium sulfate, filtered and evaporated. Chromatography of the residue (silica gel, gradient dichloromethane to dichloromethane/methanol/25% aq. ammonia solution 90:10:0.25) produced the title compound (591 mg, 97%). White foam, MS: 424.3 (M+H)$^+$.

Step 4: ((3aR,8aS)-Octahydropyrrolo[3,4-d]azepin-2(1H)-yl)((R)-4,5,6,7-tetrahydro-1H-benzo[d][1,2,3]triazol-5-yl)methanone A solution of (3aR,8aS)-benzyl 2-((R)-4,5,6,7-tetrahydro-1H-benzo[d][1,2,3]triazole-5-carbonyl)octahydropyrrolo[3,4-d]azepine-6(7H)-carboxylate (567 mg, 1.34 mmol) in methanol (3 mL) and 1 M aq. hydrochloride acid solution (3 mL) was hydrogenated at ambient temperature for 18 h at 3 bar. The solvent was evaporated. The residue was suspended in dichloromethane/methanol/25% aq. ammonia solution 90:10:0.25 for 1 h, then insoluble material was removed by filtration. The filtrate was evaporated to afford the title compound (367 mg 95%). White foam, MS: 290.2 (M+H)$^+$.

Intermediate 16

[(3aS,8aR)-2,3,3a,4,5,7,8,8a-octahydro-1H-pyrrolo[3,4-d]azepin-6-yl]-[3-cyclopropyl-5-(oxan-4-ylmethoxy)phenyl]methanone Step 1: (3aR,8aS)-tert-butyl 6-(3-cyclopropyl-5-((tetrahydro-2H-pyran-4-yl)methoxy)benzoyl)octahydropyrrolo[3,4-d]azepine-2(1H)-carboxylate The title compound was produced in analogy to example 2, replacing 4-((3aR,6aS)-octahydropyrrolo[3,4-c]pyrrole-2-carbonyl)benzenesulfonamide hydrochloride by tert-butyl (3aS,8aR)-3,3a,4,5,6,7,8,8a-octahydro-1H-pyrrolo[3,4-d]azepine-2-carboxylate (CAS-RN 1251013-07-6) and 5-cyclopropyl-6-(tetrahydro-2H-pyran-4-yloxy)nicotinic acid by 3-cyclopropyl-5-(oxan-4-ylmethoxy)benzoic acid (intermediate 9.1). White foam, MS: 521.3 (M+Na)$^+$ Step 2: [(3aS,8aR)-2,3,3a,4,5,7,8,8a-octahydro-1H-pyrrolo[3,4-d]azepin-6-yl]-[3-cyclopropyl-5-(oxan-4-ylmethoxy)phenyl]methanone To a colourless solution of (3aR,8aS)-tert-butyl 6-(3-cyclopropyl-5-((tetrahydro-2H-pyran-4-yl)methoxy)benzoyl)octahydropyrrolo[3,4-d]azepine-2(1H)-carboxylate (707 mg, 1.4 mmol) in dichloromethane (10 mL) was added trifluoroacetic acid (1.6 g, 14 mmol). The reaction mixture was stirred at room temperature for 14 h, then concentrated, and the residue was partioned between ethyl acetate and 2 M aq. sodium hydroxide solution. The organic phase was dried over magnesium sulfate, filtered and evaporated to produce the title compound (564 mg, quant.). Light yellow foam, MS: 399.3 (M+H)$^+$ Intermediate 16.1

[(3aS,6aS)-2,3,3a,4,6,6a-hexahydro-1H-pyrrolo[3,4-c]pyrrol-5-yl]-[3-cyclopropyl-5-(oxan-4-ylmethoxy)phenyl]methanone The title compound was produced in analogy to intermediate 16, replacing tert-butyl (3aS,8aR)-3,3a,4,5,6,7,8,8a-octahydro-1H-pyrrolo[3,4-d]azepine-2-carboxylate by (3aR,6aR)-tert-butyl hexahydropyrrolo[3,4-c]pyrrole-2(1H)-carboxylate (intermediate 3.1). Light yellow foam, MS: 371.3 (M+H)$^+$.

The invention claimed is:

1. A compound of formula (I)

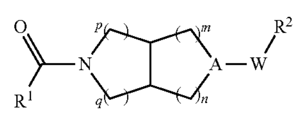

(I)

wherein $R^1$ is pyridinyl substituted with $R^3$, $R^4$, and $R^5$;

A is —N—;

W is —C(O)—;

$R^2$ is:

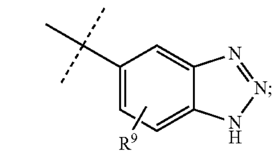
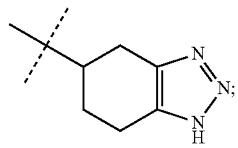
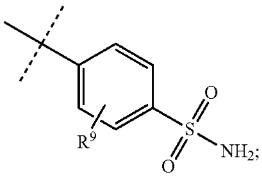
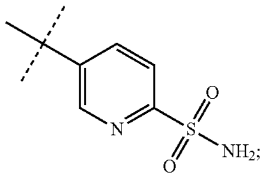
or
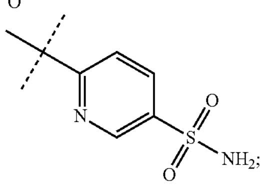

$R^3$ is tetrahydropyranylmethoxy;
$R^4$ is cycloalkyl;
$R^5$ is H;
m, n, p and q are independently selected from 1 and 2; and
$R^9$ is H, alkyl, halogen, haloalkyl or alkoxy;
or a pharmaceutically acceptable salt thereof.

2. The compound of claim 1, wherein m, n, p and q are 1; or a pharmaceutically acceptable salt thereof.

3. The compound of claim 1, wherein m and n are 1 and p and q are 2; or a pharmaceutically acceptable salt thereof.

4. The compound of claim 1, wherein m and n are 2 and p and q are 1; or a pharmaceutically acceptable salt thereof.

5. The compound of claim 1, wherein $R^2$ is:

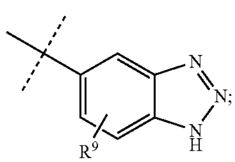
or
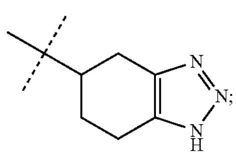

or a pharmaceutically acceptable salt thereof.

6. The compound of claim 1, wherein $R^2$ is:

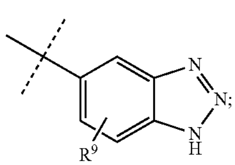

or a pharmaceutically acceptable salt thereof.

7. The compound of claim 1, wherein $R^2$ is:

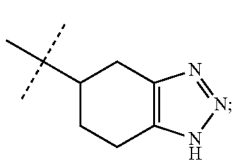

or a pharmaceutically acceptable salt thereof.

8. The compound of claim 1, wherein $R^2$ is:

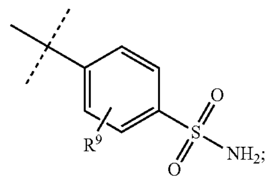
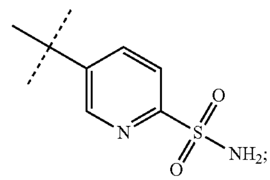
or
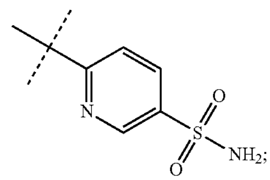

or a pharmaceutically acceptable salt thereof.

9. The compound of claim 1, wherein $R^2$ is:

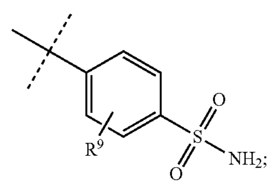

or a pharmaceutically acceptable salt thereof.

10. The compound of claim 1, wherein $R^2$ is:

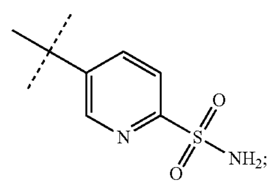

or a pharmaceutically acceptable salt thereof.

11. The compound of claim 1, wherein $R^2$ is:

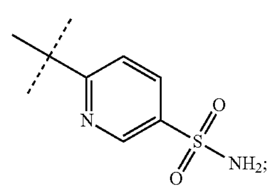

or a pharmaceutically acceptable salt thereof.

12. The compound of claim 1, wherein $R^4$ is cyclopropyl; or a pharmaceutically acceptable salt thereof.

13. The compound of claim 1, wherein the compound is selected from:

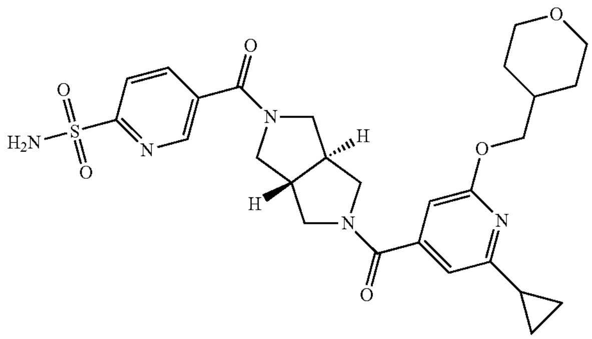 [SMILES: NS(=O)(=O)c1ccc(C(=O)N2C[C@H]3CN(C(=O)c4cc(OCC5CCOCC5)nc(C5CC5)c4)C[C@@H]3C2)cn1]

5-((3aR,6aR)-5-(2-cyclopropyl-6-((tetrahydro-2H-pyran-4-yl)methoxy)isonicotinoyl)octahydropyrrolo[3,4-c]pyrrole-2-carbonyl)pyridine-2-sulfonamide;

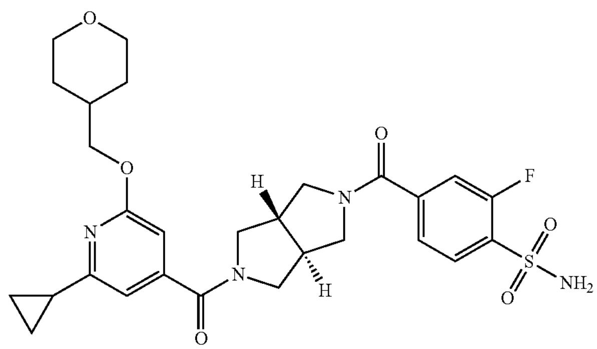

4-((3aR,6aR)-5-(2-cyclopropyl-6-((tetrahydro-2H-pyran-4-yl)methoxy)isonicotinoyl)octahydropyrrolo[3,4-c]pyrrole-2-carbonyl)-2-fluorobenzenesulfonamide;

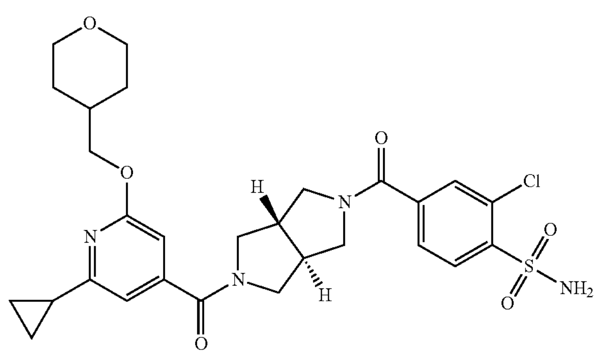 [SMILES: NS(=O)(=O)c1ccc(C(=O)N2C[C@H]3CN(C(=O)c4cc(OCC5CCOCC5)nc(C5CC5)c4)C[C@@H]3C2)cc1F]

2-chloro-4-((3aR,6aR)-5-(2-cyclopropyl-6-((tetrahydro-2H-pyran-4-yl)methoxy)isonicotinoyl)octahydropyrrolo[3,4-c]pyrrole-2-carbonyl)benzenesulfonamide;

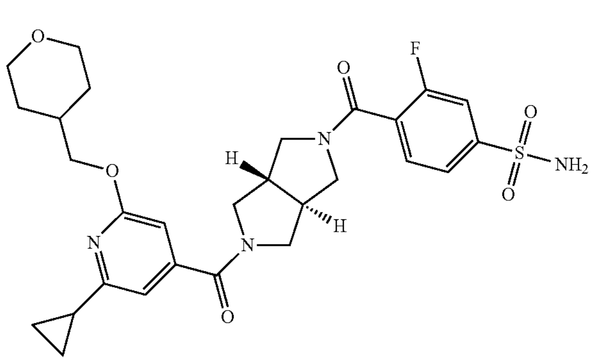 [SMILES: NS(=O)(=O)c1ccc(C(=O)N2C[C@H]3CN(C(=O)c4cc(OCC5CCOCC5)nc(C5CC5)c4)C[C@@H]3C2)c(F)c1]

4-((3aR,6aR)-5-(2-cyclopropyl-6-((tetrahydro-2H-pyran-4-yl)methoxy)isonicotinoyl)octahydropyrrolo[3,4-c]pyrrole-2-carbonyl)-3-fluorobenzenesulfonamide;

-continued

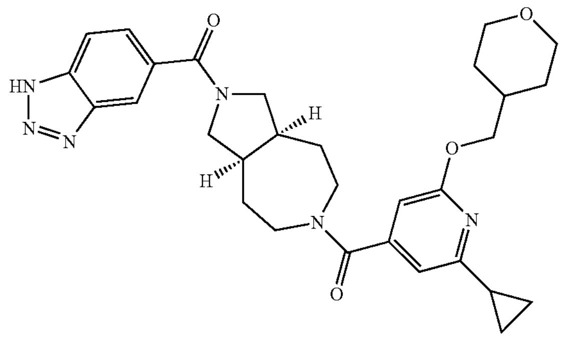 [SMILES: O=C(c1cc(OCC2CCOCC2)nc(C2CC2)c1)N1CC[C@@H]2CN(C(=O)c3ccc4[nH]nnc4c3)C[C@@H]2CC1]

((3aR,8aS)-2-(1H-benzo[d][1,2,3]triazole-5-carbonyl)octahydropyrrolo[3,4-d]azepin-6(7H)-yl)(2-cyclopropyl-6-((tetrahydro-2H-pyran-4-yl)methoxy)pyridin-4-yl)methanone;

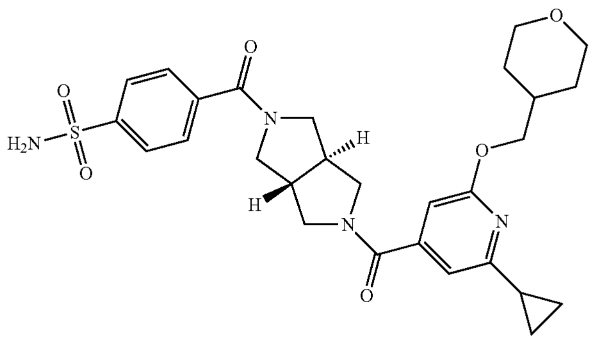 [SMILES: NS(=O)(=O)c1ccc(C(=O)N2C[C@H]3CN(C(=O)c4cc(OCC5CCOCC5)nc(C5CC5)c4)C[C@@H]3C2)cc1]

4-((3aS,6aS)-5-(2-cyclopropyl-6-((tetrahydro-2H-pyran-4-yl)methoxy)isonicotinoyl)octahydropyrrolo[3,4-c]pyrrole-2-carbonyl)benzenesulfonamide;

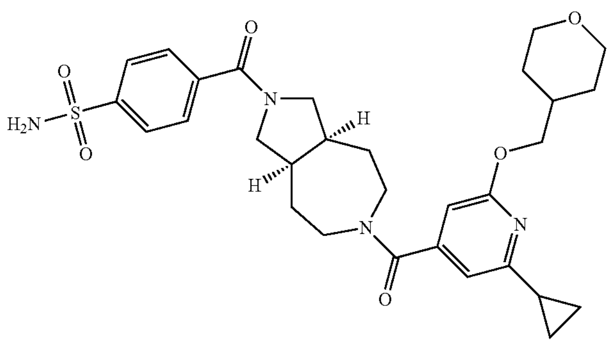 [SMILES: NS(=O)(=O)c1ccc(C(=O)N2C[C@H]3CCN(C(=O)c4cc(OCC5CCOCC5)nc(C5CC5)c4)CC[C@H]3C2)cc1]

4-((3aR,8aS)-6-(2-cyclopropyl-6-((tetrahydro-2H-pyran-4-yl)methoxy)isonicotinoyl)decahydropyrrolo[3,4-d]azepine-2-carbonyl)benzenesulfonamide;

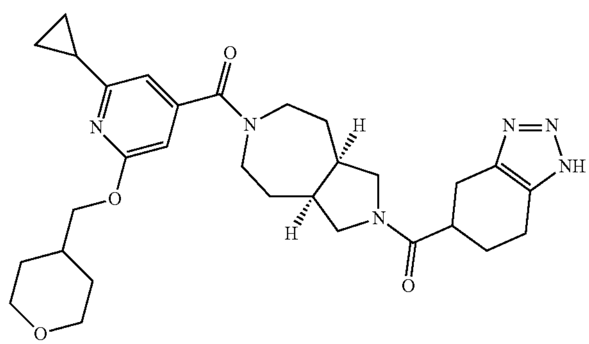 [SMILES: O=C(c1cc(OCC2CCOCC2)nc(C2CC2)c1)N1CC[C@@H]2CN(C(=O)C3CCc4[nH]nnc4C3)C[C@@H]2CC1]

((3aR,8aS)-6-(2-cyclopropyl-6-((tetrahydro-2H-pyran-4-yl)methoxy)isonicotinoyl)-octahydropyrrolo[3,4-d]azepin-2(1H)-yl)(4,5,6,7-tetrahydro-1H-benzo[d][1,2,3]triazol-5-yl)methanone;

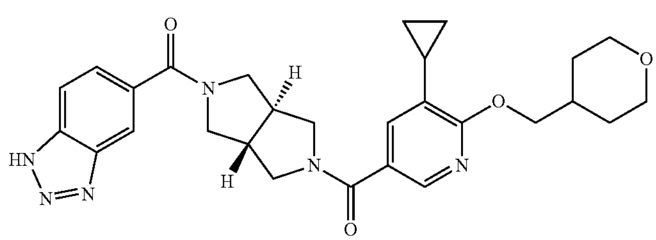 [SMILES: O=C(c1cnc(OCC2CCOCC2)c(C2CC2)c1)N1C[C@@H]2CN(C(=O)c3ccc4[nH]nnc4c3)C[C@H]2C1]

((3aS,6aS)-5-(1H-benzo[d][1,2,3]triazole-5-carbonyl)hexahydropyrrolo[3,4-c]pyrrol-2(1H)-yl)(5-cyclopropyl-6-((tetrahydro-2H-pyran-4-yl)methoxy)pyridin-3-yl)methanone;

-continued

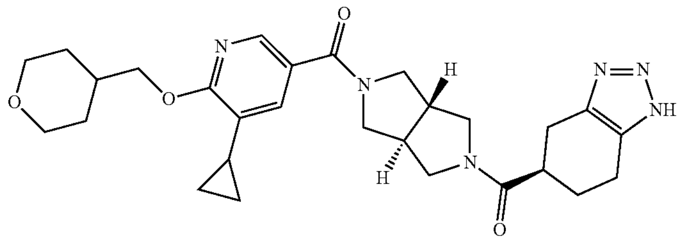 [SMILES: O=C(c1cnc(OCC2CCOCC2)c(C2CC2)c1)N1C[C@@H]2CN(C(=O)[C@@H]3CCc4[nH]nnc4C3)C[C@H]2C1]

((3aS,6aS)-5-(5-cyclopropyl-6-((tetrahydro-2H-pyran-4-yl)methoxy)nicotinoyl)-hexahydropyrrolo[3,4-c]pyrrol-2(1H)-yl)((R)-4,5,6,7-tetrahydro-1H-benzo[d][1,2,3]triazol-5-yl)methanone;

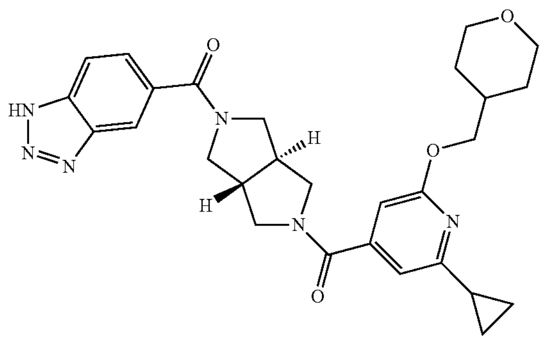 [SMILES: O=C(c1cc(OCC2CCOCC2)nc(C2CC2)c1)N1C[C@@H]2CN(C(=O)c3ccc4[nH]nnc4c3)C[C@H]2C1]

((3aS,6aS)-5-(1H-benzo[d][1,2,3]triazole-5-carbonyl)hexahydropyrrolo[3,4-c]pyrrol-2(1H)-yl)(2-cyclopropyl-6-((tetrahydro-2H-pyran-4-yl)methoxy)pyridin-4-yl)methanone;

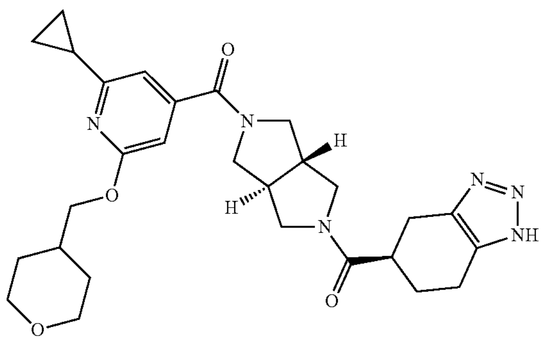 [SMILES: O=C(c1cc(OCC2CCOCC2)nc(C2CC2)c1)N1C[C@@H]2CN(C(=O)[C@@H]3CCc4[nH]nnc4C3)C[C@H]2C1]

((3aS,6aS)-5-(2-cyclopropyl-6-((tetrahydro-2H-pyran-4-yl)methoxy)isonicotinoyl)-hexahydropyrrolo[3,4-c]pyrrol-2(1H)-yl)((R)-4,5,6,7-tetrahydro-1H-benzo[d][1,2,3]triazol-5-yl)methanone

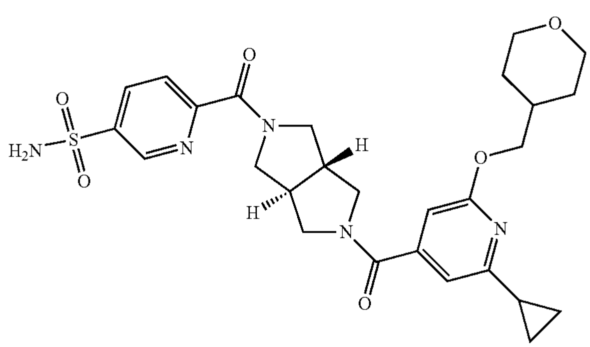 [SMILES: NS(=O)(=O)c1ccc(C(=O)N2C[C@@H]3CN(C(=O)c4cc(OCC5CCOCC5)nc(C5CC5)c4)C[C@H]3C2)nc1]

6-((3aR,6aR)-5-(2-cyclopropyl-6-((tetrahydro-2H-pyran-4-yl)methoxy)isonicotinoyl)octahydropyrrolo[3,4-c]pyrrole-2-carbonyl)pyridine-3-sulfonamide;

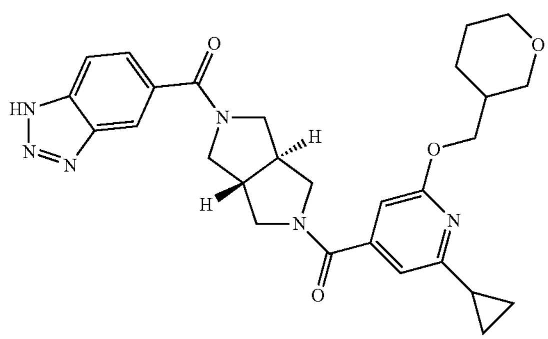 [SMILES: O=C(c1cc(OCC2CCCOC2)nc(C2CC2)c1)N1C[C@@H]2CN(C(=O)c3ccc4[nH]nnc4c3)C[C@H]2C1]

((3aS,6aS)-5-(1H-benzo[d][1,2,3]triazole-5-carbonyl)hexahydropyrrolo[3,4-c]pyrrol-2(1H)-yl)(2-cyclopropyl-6-((tetrahydro-2H-pyran-3-yl)methoxy)pyridin-4-yl)methanone;

-continued

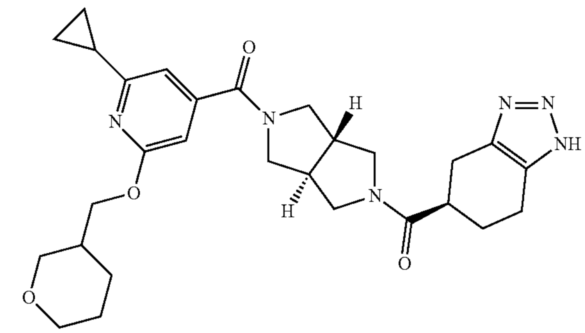 [SMILES: O=C(c1cc(OCC2CCCOC2)nc(C2CC2)c1)N1C[C@@H]2CN(C(=O)[C@@H]3CCc4[nH]nnc4C3)C[C@H]2C1]

((3aS,6aS)-5-(2-cyclopropyl-6-((tetrahydro-2H-pyran-3-yl)methoxy)isonicotinoyl)-hexahydropyrrolo[3,4-c]pyrrol-2(1H)-yl)((R)-4,5,6,7-tetrahydro-1H-benzo[d][1,2,3]triazol-5-yl)methanone;

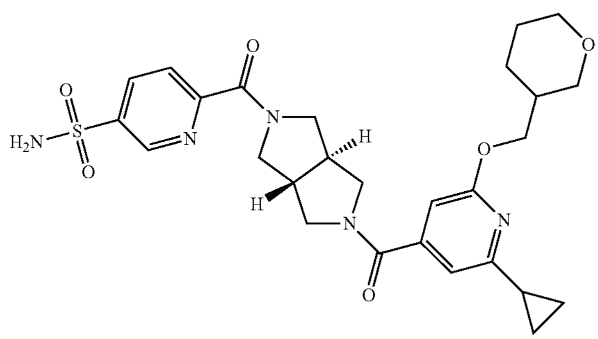 [SMILES: NS(=O)(=O)c1ccc(C(=O)N2C[C@H]3CN(C(=O)c4cc(OCC5CCCOC5)nc(C5CC5)c4)C[C@@H]3C2)nc1]

6-((3aR,6aR)-5-(2-cyclopropyl-6-((tetrahydro-2H-pyran-3-yl)methoxy)isonicotinoyl)octahydropyrrolo[3,4-c]pyrrole-2-carbonyl)pyridine-3-sulfonamide;

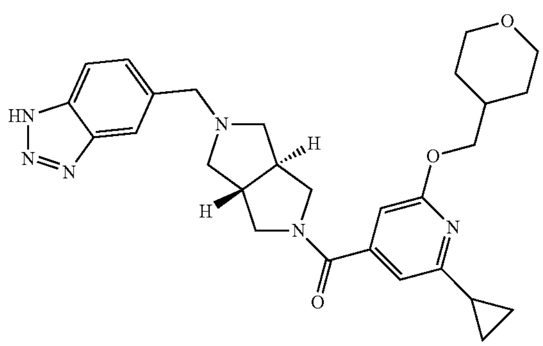 [SMILES: O=C(c1cc(OCC2CCOCC2)nc(C2CC2)c1)N1C[C@@H]2CN(Cc3ccc4[nH]nnc4c3)C[C@H]2C1]

((3aS,6aS)-5-((1H-benzo[d][1,2,3]triazol-5-yl)methyl)hexahydropyrrolo[3,4-c]pyrrol-2(1H)-yl)(2-cyclopropyl-6-((tetrahydro-2H-pyran-4-yl)methoxy)pyridin-4-yl)methanone;

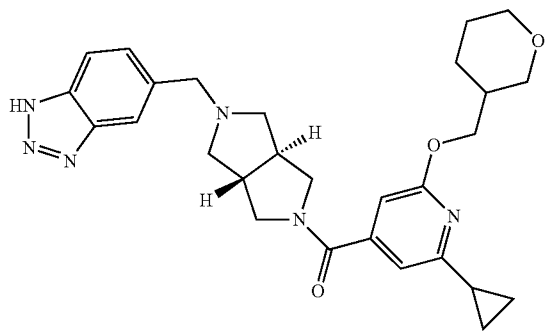 [SMILES: O=C(c1cc(OCC2CCCOC2)nc(C2CC2)c1)N1C[C@@H]2CN(Cc3ccc4[nH]nnc4c3)C[C@H]2C1]

((3aS,6aS)-5-((1H-benzo[d][1,2,3]triazol-5-yl)methyl)hexahydropyrrolo[3,4-c]pyrrol-2(1H)-yl)(2-cyclopropyl-6-((tetrahydro-2H-pyran-3-yl)methoxy)pyridin-4-yl)methanone;

-continued

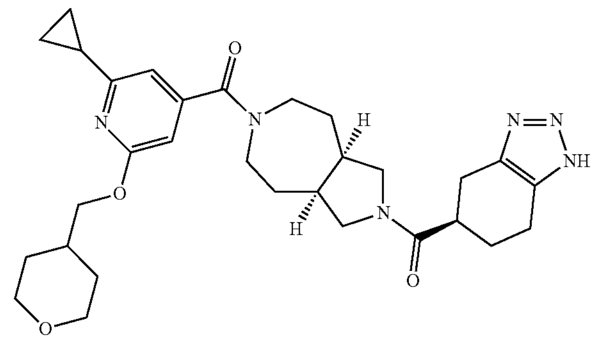 [SMILES: O=C(c1cc(OCC2CCOCC2)nc(C2CC2)c1)N1CC[C@@H]2CN(C(=O)[C@@H]3CCc4[nH]nnc4C3)C[C@@H]2CC1]

((3aR,8aS)-6-(2-cyclopropyl-6-((tetrahydro-2H-pyran-4-yl)methoxy)isonicotinoyl)-octahydropyrrolo[3,4-d]azepin-2(1H)-yl)((R)-4,5,6,7-tetrahydro-1H-benzo[d][1,2,3]triazol-5-yl)methanone;

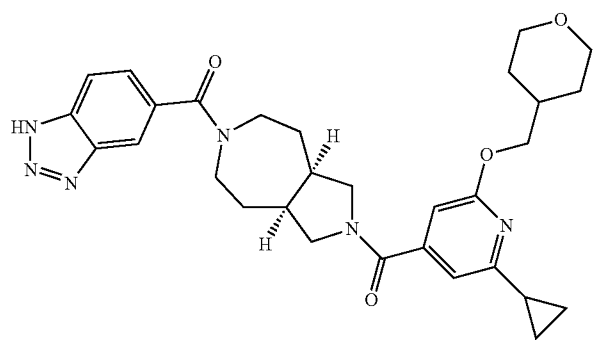 [SMILES: O=C(c1ccc2[nH]nnc2c1)N1CC[C@@H]2CN(C(=O)c3cc(OCC4CCOCC4)nc(C4CC4)c3)C[C@@H]2CC1]

((3aR,8aS)-6-(1H-benzo[d][1,2,3]triazole-5-carbonyl)octahydropyrrolo[3,4-d]azepin-2(1H)-yl)(2-cyclopropyl-6-((tetrahydro-2H-pyran-4-yl)methoxy)pyridin-4-yl)methanone;

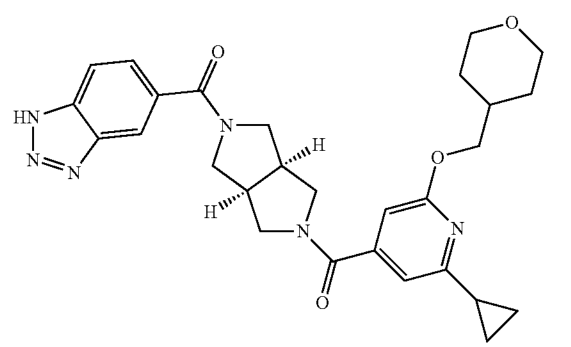 [SMILES: O=C(c1cc(OCC2CCOCC2)nc(C2CC2)c1)N1C[C@@H]2CN(C(=O)c3ccc4[nH]nnc4c3)C[C@@H]2C1]

((3aR,6aS)-5-(1H-benzo[d][1,2,3]triazole-5-carbonyl)hexahydropyrrolo[3,4-c]pyrrol-2(1H)-yl)(2-cyclopropyl-6-((tetrahydro-2H-pyran-4-yl)methoxy)pyridin-4-yl)methanone;

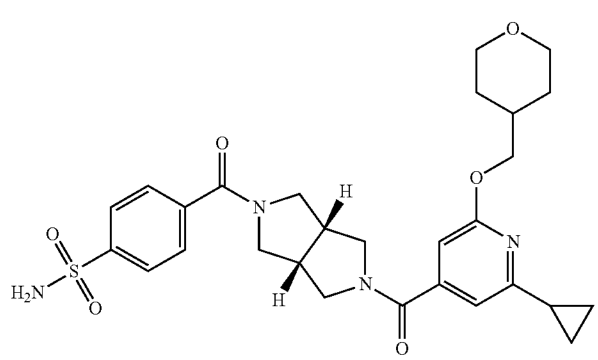 [SMILES: NS(=O)(=O)c1ccc(C(=O)N2C[C@@H]3CN(C(=O)c4cc(OCC5CCOCC5)nc(C5CC5)c4)C[C@@H]3C2)cc1]

4-((3aR,6aS)-5-(2-cyclopropyl-6-((tetrahydro-2H-pyran-4-yl)methoxy)isonicotinoyl)octahydro-pyrrolo[3,4-c]pyrrole-2-carbonyl)benzenesulfonamide;

and

-continued

| | |
|---|---|
| 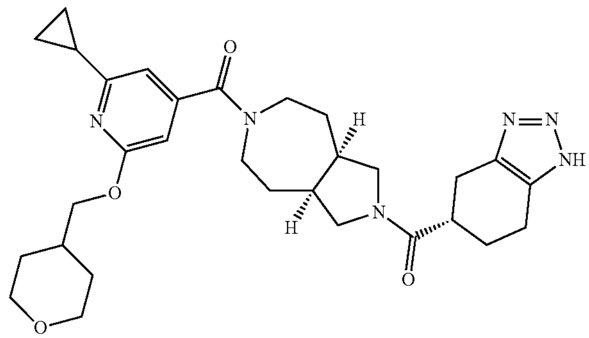 [SMILES: O=C(c1cc(OCC2CCOCC2)nc(C2CC2)c1)N1CC[C@@H]2CN(C(=O)[C@H]3CCc4[nH]nnc4C3)C[C@@H]2CC1] | ((3aR,8aS)-6-(2-Cyclopropyl-6-((tetrahydro-2H-pyran-4-yl)methoxy)isonicotinoyl)octa-hydropyrrolo[3,4-d]azepin-2(1H)-yl)((S)-4,5,6,7-tetrahydro-1H-benzo[d][1,2,3]triazol-5-yl)methanone; |

or a pharmaceutically acceptable salt thereof.

14. The compound of claim 13, wherein the compound is selected from:

| | |
|---|---|
| 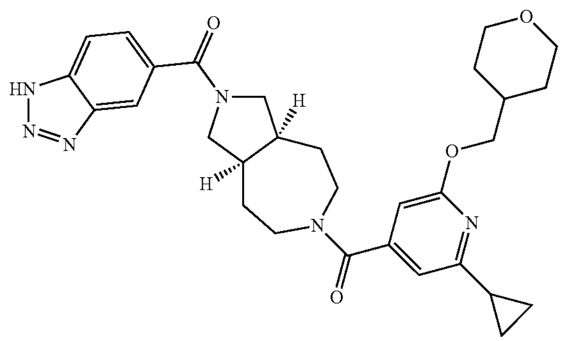 [SMILES: O=C(c1cc(OCC2CCOCC2)nc(C2CC2)c1)N1CC[C@@H]2CN(C(=O)c3ccc4[nH]nnc4c3)C[C@@H]2CC1] | ((3aR,8aS)-2-(1H-benzo[d][1,2,3]triazole-5-carbonyl)octahydropyrrolo[3,4-d]azepin-6(7H)-yl)(2-cyclopropyl-6-((tetrahydro-2H-pyran-4-yl)methoxy)pyridin-4-yl)methanone; |
| 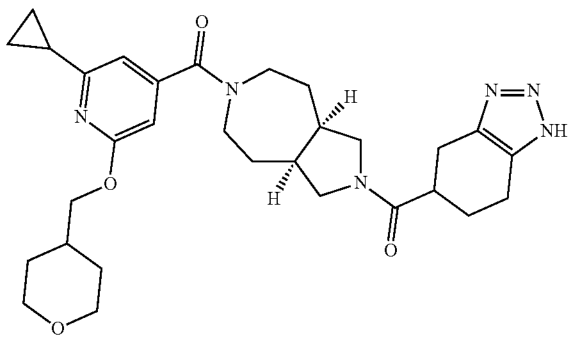 [SMILES: O=C(c1cc(OCC2CCOCC2)nc(C2CC2)c1)N1CC[C@@H]2CN(C(=O)C3CCc4[nH]nnc4C3)C[C@@H]2CC1] | ((3aR,8aS)-6-(2-cyclopropyl-6-((tetrahydro-2H-pyran-4-yl)methoxy)isonicotinoyl)-octahydropyrrolo[3,4-d]azepin-2(1H)-yl)(4,5,6,7-tetrahydro-1H-benzo[d][1,2,3]triazol-5-yl)methanone; |
| 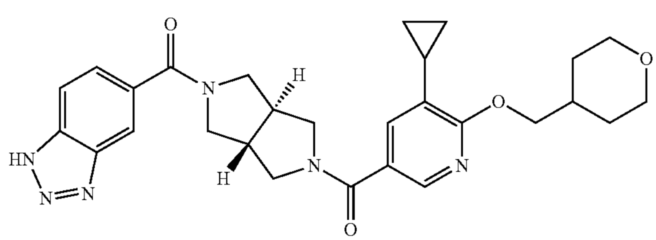 [SMILES: O=C(c1cnc(OCC2CCOCC2)c(C2CC2)c1)N1C[C@@H]2CN(C(=O)c3ccc4[nH]nnc4c3)C[C@H]2C1] | ((3aS,6aS)-5-(1H-benzo[d][1,2,3]triazole-5-carbonyl)hexahydropyrrolo[3,4-c]pyrrol-2(1H)-yl)(5-cyclopropyl-6-((tetrahydro-2H-pyran-4-yl)methoxy)pyridin-3-yl)methanone; |

-continued

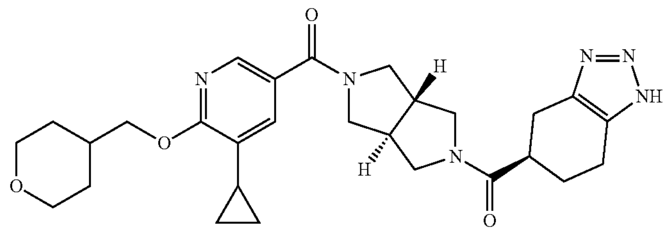 [SMILES: O=C(c1cnc(OCC2CCOCC2)c(C2CC2)c1)N1C[C@@H]2CN(C(=O)[C@@H]3CCc4[nH]nnc4C3)C[C@H]2C1]

((3aS,6aS)-5-(5-cyclopropyl-6-((tetrahydro-2H-pyran-4-yl)methoxy)nicotinoyl)-hexahydropyrrolo[3,4-c]pyrrol-2(1H)-yl)((R)-4,5,6,7-tetrahydro-1H-benzo[d][1,2,3]triazol-5-yl)methanone;

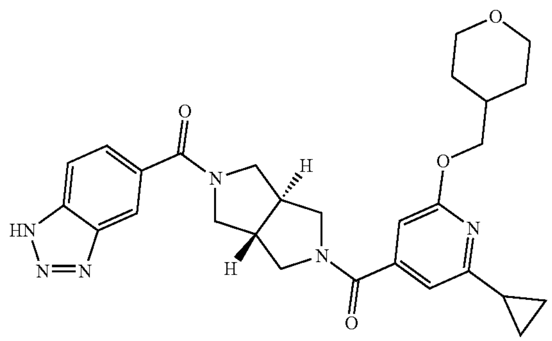 [SMILES: O=C(c1cc(OCC2CCOCC2)nc(C2CC2)c1)N1C[C@@H]2CN(C(=O)c3ccc4[nH]nnc4c3)C[C@H]2C1]

((3aS,6aS)-5-(1H-benzo[d][1,2,3]triazole-5-carbonyl)hexahydropyrrolo[3,4-c]pyrrol-2(1H)-yl)(2-cyclopropyl-6-((tetrahydro-2H-pyran-4-yl)methoxy)pyridin-4-yl)methanone;

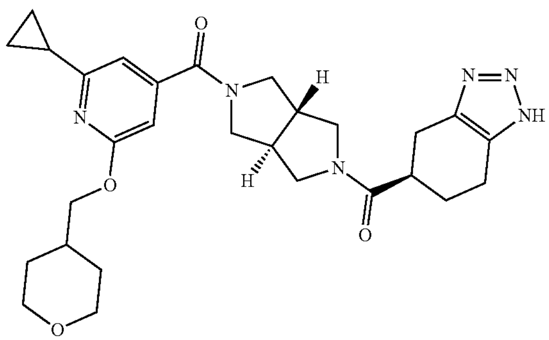 [SMILES: O=C(c1cc(OCC2CCOCC2)nc(C2CC2)c1)N1C[C@@H]2CN(C(=O)[C@@H]3CCc4[nH]nnc4C3)C[C@H]2C1]

((3aS,6aS)-5-(2-cyclopropyl-6-((tetrahydro-2H-pyran-4-yl)methoxy)isonicotinoyl)-hexahydropyrrolo[3,4-c]pyrrol-2(1H)-yl)((R)-4,5,6,7-tetrahydro-1H-benzo[d][1,2,3]triazol-5-yl)methanone;

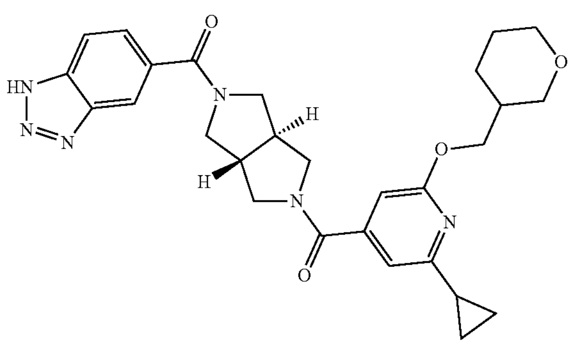 [SMILES: O=C(c1cc(OCC2CCCOC2)nc(C2CC2)c1)N1C[C@@H]2CN(C(=O)c3ccc4[nH]nnc4c3)C[C@H]2C1]

((3aS,6aS)-5-(1H-benzo[d][1,2,3]triazole-5-carbonyl)hexahydropyrrolo[3,4-c]pyrrol-2(1H)-yl)(2-cyclopropyl-6-((tetrahydro-2H-pyran-3-yl)methoxy)pyridin-4-yl)methanone;

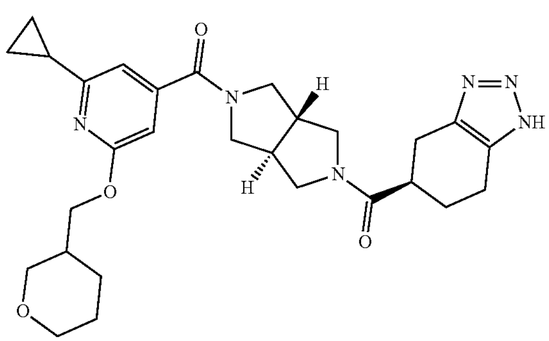 [SMILES: O=C(c1cc(OCC2CCCOC2)nc(C2CC2)c1)N1C[C@@H]2CN(C(=O)[C@@H]3CCc4[nH]nnc4C3)C[C@H]2C1]

((3aS,6aS)-5-(2-cyclopropyl-6-((tetrahydro-2H-pyran-3-yl)methoxy)isonicotinoyl)-hexahydropyrrolo[3,4-c]pyrrol-2(1H)-yl)((R)-4,5,6,7-tetrahydro-1H-benzo[d][1,2,3]triazol-5-yl)methanone;

-continued

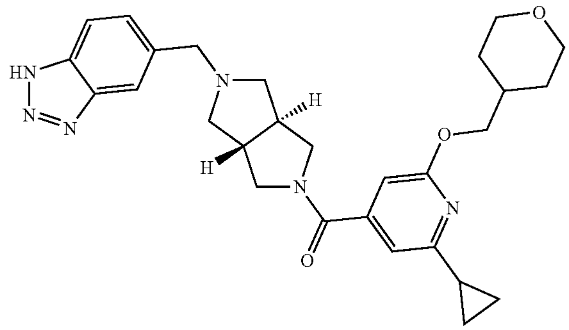 [SMILES: O=C(c1cc(OCC2CCOCC2)nc(C2CC2)c1)N1C[C@@H]2CN(Cc3ccc4[nH]nnc4c3)C[C@H]2C1]

((3aS,6aS)-5-((1H-benzo[d][1,2,3]triazol-5-yl)methyl)hexahydropyrrolo[3,4-c]pyrrol-2(1H)-yl)(2-cyclopropyl-6-((tetrahydro-2H-pyran-4-yl)methoxy)pyridin-4-yl)methanone;

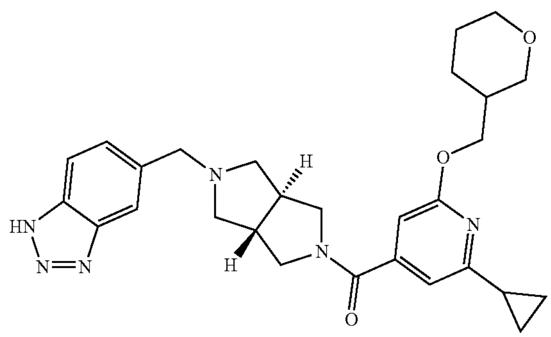 [SMILES: O=C(c1cc(OCC2CCCOC2)nc(C2CC2)c1)N1C[C@@H]2CN(Cc3ccc4[nH]nnc4c3)C[C@H]2C1]

((3aS,6aS)-5-((1H-benzo[d][1,2,3]triazol-5-yl)methyl)hexahydropyrrolo[3,4-c]pyrrol-2(1H)-yl)(2-cyclopropyl-6-((tetrahydro-2H-pyran-3-yl)methoxy)pyridin-4-yl)methanone;

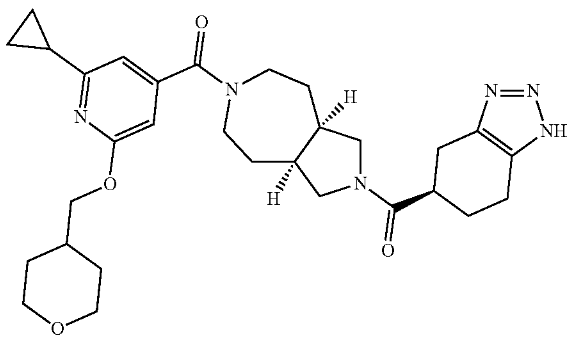 [SMILES: O=C(c1cc(OCC2CCOCC2)nc(C2CC2)c1)N1CC[C@@H]2CN(C(=O)[C@@H]3CCc4[nH]nnc4C3)C[C@@H]2CC1]

((3aR,8aS)-6-(2-cyclopropyl-6-((tetrahydro-2H-pyran-4-yl)methoxy)isonicotinoyl)-octahydropyrrolo[3,4-d]azepin-2(1H)-yl)((R)-4,5,6,7-tetrahydro-1H-benzo[d][1,2,3]triazol-5-yl)methanone;

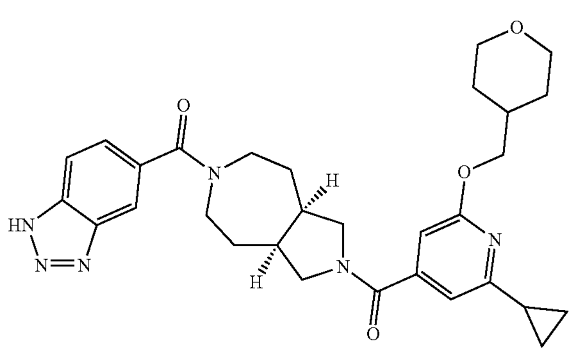 [SMILES: O=C(c1ccc2[nH]nnc2c1)N1CC[C@@H]2CN(C(=O)c3cc(OCC4CCOCC4)nc(C4CC4)c3)C[C@@H]2CC1]

((3aR,8aS)-6-(1H-benzo[d][1,2,3]triazole-5-carbonyl)octahydropyrrolo[3,4-d]azepin-2(1H)-yl)(2-cyclopropyl-6-((tetrahydro-2H-pyran-4-yl)methoxy)pyridin-4-yl)methanone;

-continued

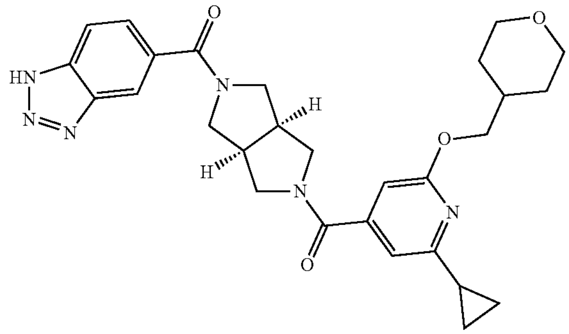 [SMILES: O=C(c1cc(OCC2CCOCC2)nc(C2CC2)c1)N1C[C@@H]2CN(C(=O)c3ccc4[nH]nnc4c3)C[C@@H]2C1]

((3aR,6aS)-5-(1H-benzo[d][1,2,3]triazole-5-carbonyl)hexahydropyrrolo[3,4-c]pyrrol-2(1H)-yl)(2-cyclopropyl-6-((tetrahydro-2H-pyran-4-yl)methoxy)pyridin-4-yl)methanone;

and

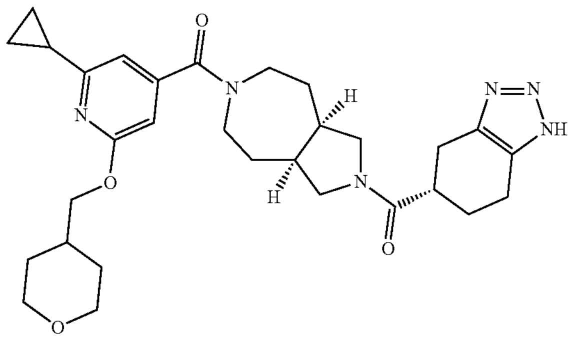 [SMILES: O=C(c1cc(OCC2CCOCC2)nc(C2CC2)c1)N1CC[C@@H]2CN(C(=O)[C@H]3CCc4[nH]nnc4C3)C[C@@H]2CC1]

((3aR,8aS)-6-(2-Cyclopropyl-6-((tetrahydro-2H-pyran-4-yl)methoxy)isonicotinoyl)octahydropyrrolo[3,4-d]azepin-2(1H)-yl)((S)-4,5,6,7-tetrahydro-1H-benzo[d][1,2,3]triazol-5-yl)methanone;

or a pharmaceutically acceptable salt thereof.

15. The compound of claim 14, wherein the compound is selected from:

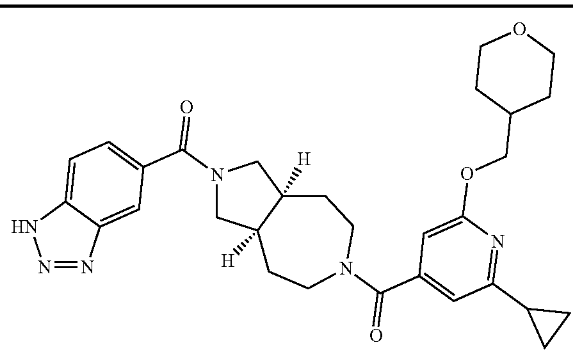

((3aR,8aS)-2-(1H-benzo[d][1,2,3]triazole-5-carbonyl)octahydropyrrolo[3,4-d]azepin-6(7H)-yl)(2-cyclopropyl-6-((tetrahydro-2H-pyran-4-yl)methoxy)pyridin-4-yl)methanone;

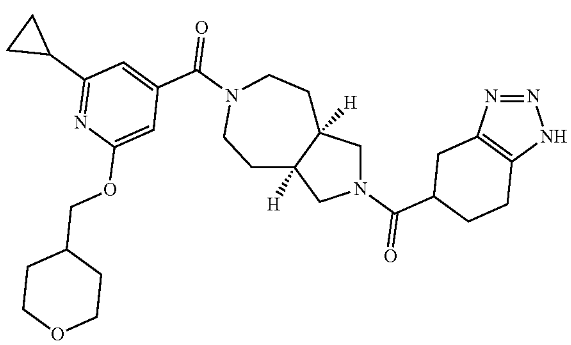 [SMILES: O=C(c1cc(OCC2CCOCC2)nc(C2CC2)c1)N1CC[C@@H]2CN(C(=O)C3CCc4[nH]nnc4C3)C[C@@H]2CC1]

((3aR,8aS)-6-(2-cyclopropyl-6-((tetrahydro-2H-pyran-4-yl)methoxy)isonicotinoyl)-octahydropyrrolo[3,4-d]azepin-2(1H)-yl)(4,5,6,7-tetrahydro-1H-benzo[d][1,2,3]triazol-5-yl)methanone;

-continued

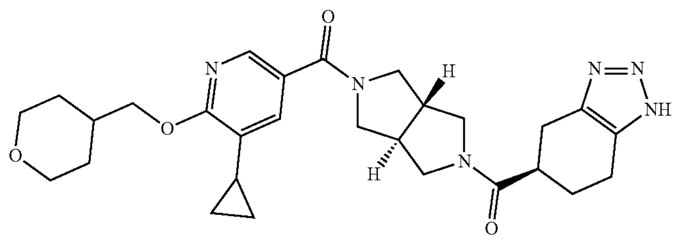 [SMILES: O=C(c1cnc(OCC2CCOCC2)c(C2CC2)c1)N1C[C@@H]2CN(C(=O)[C@@H]3CCc4[nH]nnc4C3)C[C@H]2C1]

((3aS,6aS)-5-(5-cyclopropyl-6-((tetrahydro-2H-pyran-4-yl)methoxy)nicotinoyl)-hexahydropyrrolo[3,4-c]pyrrol-2(1H)-yl)((R)-4,5,6,7-tetrahydro-1H-benzo[d][1,2,3]triazol-5-yl)methanone;

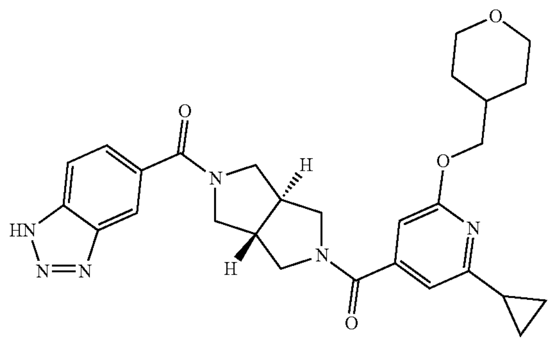 [SMILES: O=C(c1cc(OCC2CCOCC2)nc(C2CC2)c1)N1C[C@@H]2CN(C(=O)c3ccc4[nH]nnc4c3)C[C@H]2C1]

((3aS,6aS)-5-(1H-benzo[d][1,2,3]triazole-5-carbonyl)hexahydropyrrolo[3,4-c]pyrrol-2(1H)-yl)(2-cyclopropyl-6-((tetrahydro-2H-pyran-4-yl)methoxy)pyridin-4-yl)methanone;

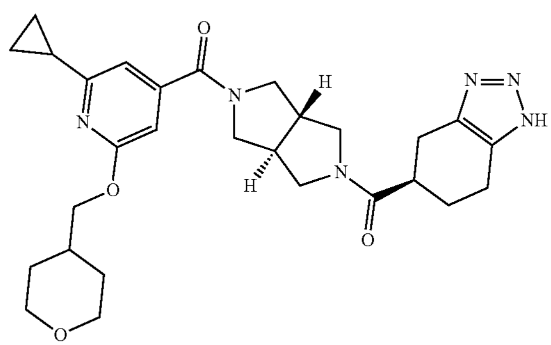 [SMILES: O=C(c1cc(OCC2CCOCC2)nc(C2CC2)c1)N1C[C@@H]2CN(C(=O)[C@@H]3CCc4[nH]nnc4C3)C[C@H]2C1]

((3aS,6aS)-5-(2-cyclopropyl-6-((tetrahydro-2H-pyran-4-yl)methoxy)isonicotinoyl)-hexahydropyrrolo[3,4-c]pyrrol-2(1H)-yl)((R)-4,5,6,7-tetrahydro-1H-benzo[d][1,2,3]triazol-5-yl)methanone;

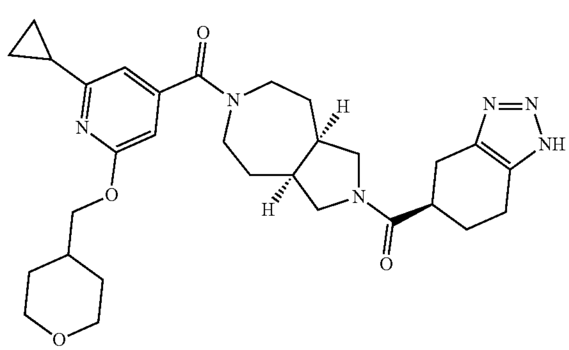 [SMILES: O=C(c1cc(OCC2CCOCC2)nc(C2CC2)c1)N1CC[C@@H]2CN(C(=O)[C@@H]3CCc4[nH]nnc4C3)C[C@@H]2CC1]

((3aR,8aS)-6-(2-cyclopropyl-6-((tetrahydro-2H-pyran-4-yl)methoxy)isonicotinoyl)-octahydropyrrolo[3,4-d]azepin-2(1H)-yl)((R)-4,5,6,7-tetrahydro-1H-benzo[d][1,2,3]triazol-5-yl)methanone;

and

-continued

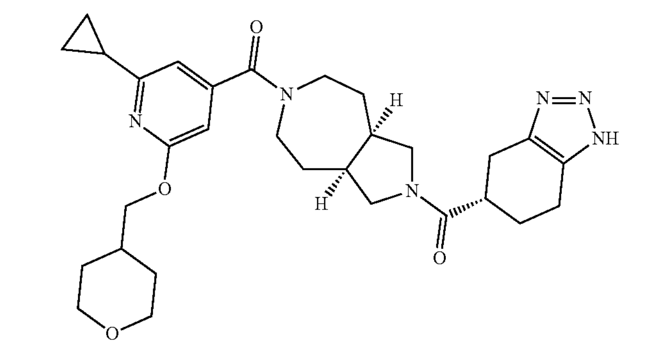 [SMILES: O=C(c1cc(OCC2CCOCC2)nc(C2CC2)c1)N1CC[C@@H]2CN(C(=O)[C@H]3CCc4[nH]nnc4C3)C[C@@H]2CC1]

((3aR,8aS)-6-(2-Cyclopropyl-6-((tetrahydro-2H-pyran-4-yl)methoxy)isonicotinoyl)octa-hydropyrrolo[3,4-d]azepin-2(1H)-yl)((S)-4,5,6,7-tetrahydro-1H-benzo[d][1,2,3]triazol-5-yl)methanone;

or a pharmaceutically acceptable salt thereof.

16. The compound of claim 15, wherein the compound is selected from:

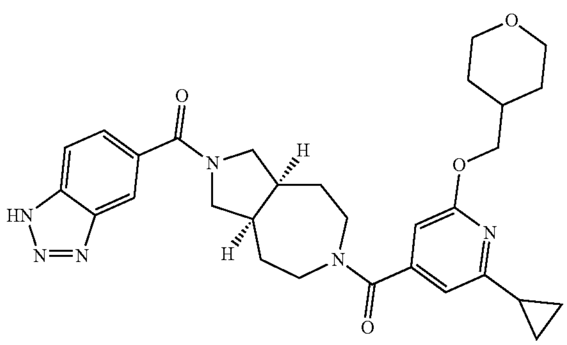 [SMILES: O=C(c1cc(OCC2CCOCC2)nc(C2CC2)c1)N1CC[C@@H]2CN(C(=O)c3ccc4[nH]nnc4c3)C[C@@H]2CC1]

((3aR,8aS)-2-(1H-benzo[d][1,2,3]triazole-5-carbonyl)octahydropyrrolo[3,4-d]azepin-6(7H)-yl)(2-cyclopropyl-6-((tetrahydro-2H-pyran-4-yl)methoxy)pyridin-4-yl)methanone;

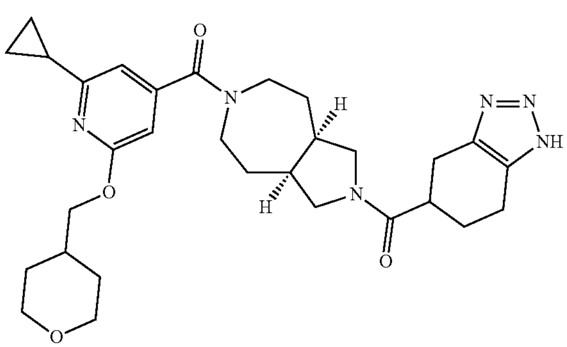 [SMILES: O=C(c1cc(OCC2CCOCC2)nc(C2CC2)c1)N1CC[C@@H]2CN(C(=O)C3CCc4[nH]nnc4C3)C[C@@H]2CC1]

((3aR,8aS)-6-(2-cyclopropyl-6-((tetrahydro-2H-pyran-4-yl)methoxy)isonicotinoyl)-octahydropyrrolo[3,4-d]azepin-2(1H)-yl)(4,5,6,7-tetrahydro-1H-benzo[d][1,2,3]triazol-5-yl)methanone;

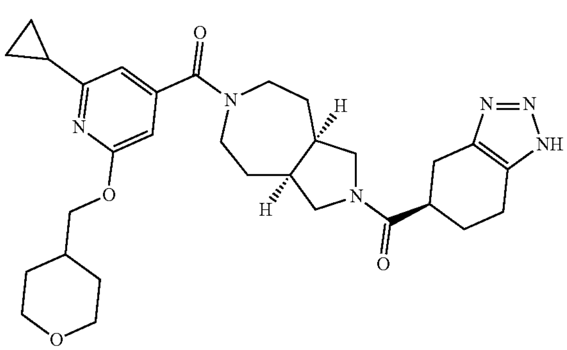 [SMILES: O=C(c1cc(OCC2CCOCC2)nc(C2CC2)c1)N1CC[C@@H]2CN(C(=O)[C@@H]3CCc4[nH]nnc4C3)C[C@@H]2CC1]

((3aR,8aS)-6-(2-cyclopropyl-6-((tetrahydro-2H-pyran-4-yl)methoxy)isonicotinoyl)-octahydropyrrolo[3,4-d]azepin-2(1H)-yl)((R)-4,5,6,7-tetrahydro-1H-benzo[d][1,2,3]triazol-5-yl)methanone;

and

-continued

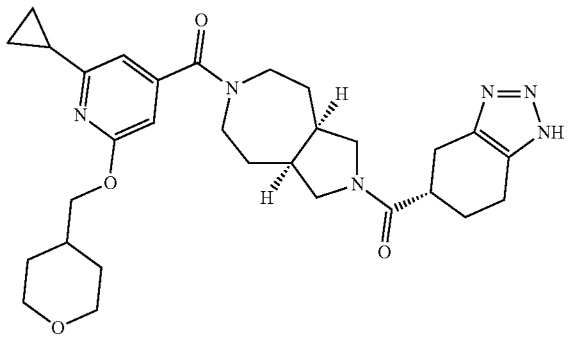 [SMILES: O=C(c1cc(OCC2CCOCC2)nc(C2CC2)c1)N1CC[C@@H]2CN(C(=O)[C@H]3CCc4[nH]nnc4C3)C[C@@H]2CC1]

((3aR,8aS)-6-(2-Cyclopropyl-6-((tetrahydro-2H-pyran-4-yl)methoxy)isonicotinoyl)octahydropyrrolo[3,4-d]azepin-2(1H)-yl)((S)-4,5,6,7-tetrahydro-1H-benzo[d][1,2,3]triazol-5-yl)methanone;

or a pharmaceutically acceptable salt thereof.

17. The compound

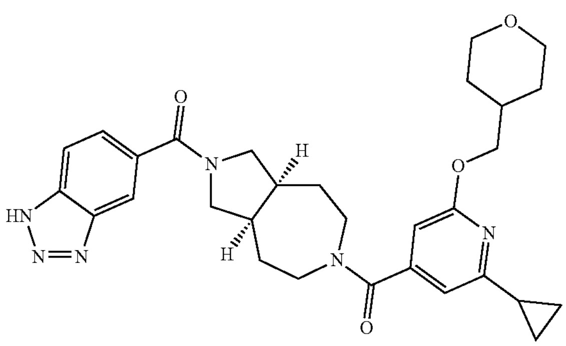 [SMILES: O=C(c1cc(OCC2CCOCC2)nc(C2CC2)c1)N1CC[C@@H]2CN(C(=O)c3ccc4[nH]nnc4c3)C[C@@H]2CC1]

((3aR,8aS)-2-(1H-benzo[d][1,2,3]triazole-5-carbonyl)octahydropyrrolo[3,4-d]azepin-6(7H)-yl)(2-cyclopropyl-6-((tetrahydro-2H-pyran-4-yl)methoxy)pyridin-4-yl)methanone;

or a pharmaceutically acceptable salt thereof.

18. The compound

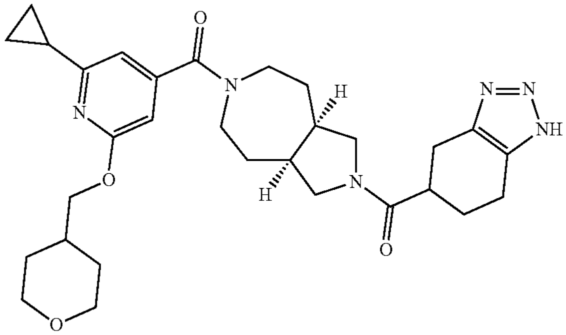 [SMILES: O=C(c1cc(OCC2CCOCC2)nc(C2CC2)c1)N1CC[C@@H]2CN(C(=O)C3CCc4[nH]nnc4C3)C[C@@H]2CC1]

((3aR,8aS)-6-(2-cyclopropyl-6-((tetrahydro-2H-pyran-4-yl)methoxy)isonicotinoyl)-octahydropyrrolo[3,4-d]azepin-2(1H)-yl)(4,5,6,7-tetrahydro-1H-benzo[d][1,2,3]triazol-5-yl)methanone;

or a pharmaceutically acceptable salt thereof.

19. The compound

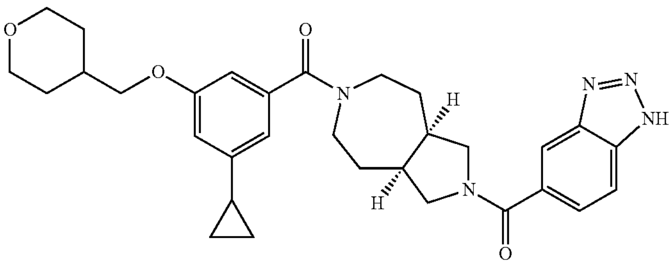 [SMILES: O=C(c1cc(OCC2CCOCC2)cc(C2CC2)c1)N1CC[C@@H]2CN(C(=O)c3ccc4[nH]nnc4c3)C[C@@H]2CC1]

((3aR,8aS)-2-(1H-benzo[d][1,2,3]triazole-5-carbonyl)octahydropyrrolo[3,4-d]azepin-6(2H)-yl)(3-cyclopropyl-5-((tetrahydro-2H-pyran-4-yl)methoxy)phenyl)methanone;

or a pharmaceutically acceptable salt thereof.

20. The compound

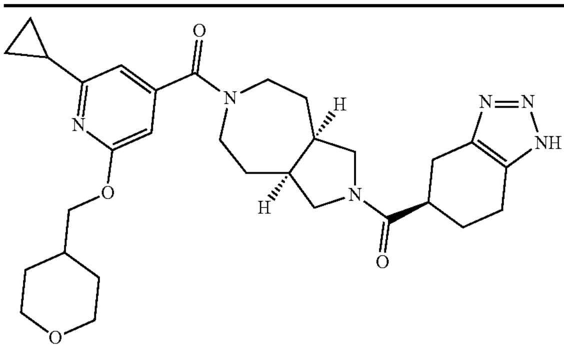

((3aR,8aS)-6-(2-cyclopropyl-6-((tetrahydro-2H-pyran-4-yl)methoxy)isonicotinoyl)-octahydropyrrolo[3,4-d]azepin-2(1H)-yl)((R)-4,5,6,7-tetrahydro-1H-benzo[d][1,2,3]triazol-5-yl)methanone;

or a pharmaceutically acceptable salt thereof.

21. The compound

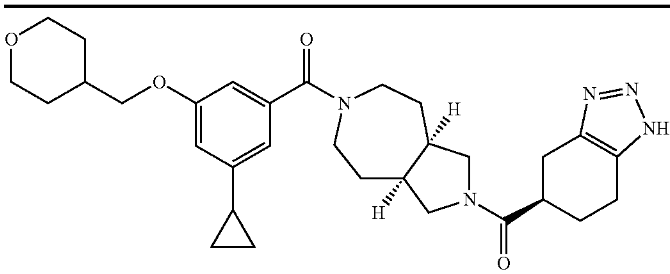

((3aR,8aS)-6-(3-cyclopropyl-5-((tetrahydro-2H-pyran-4-yl)methoxy)benzoyl)octahydropyrrolo[3,4-d]azepin-2(1H)-yl)((R)-4,5,6,7-tetrahydro-1H-benzo[d][1,2,3]triazol-5-yl)methanone;

or a pharmaceutically acceptable salt thereof.

22. The compound

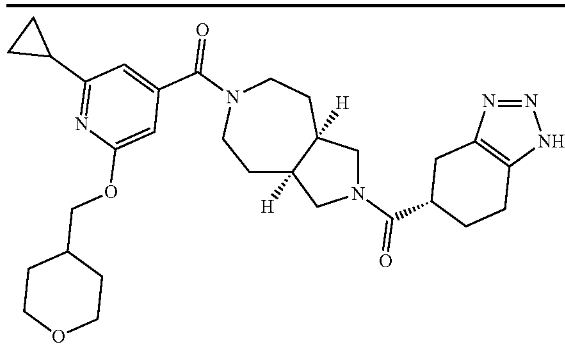

((3aR,8aS)-6-(2-Cyclopropyl-6-((tetrahydro-2H-pyran-4-yl)methoxy)isonicotinoyl)octa-hydropyrrolo[3,4-d]azepin-2(1H)-yl)((S)-4,5,6,7-tetrahydro-1H-benzo[d][1,2,3]triazol-5-yl)methanone;

or a pharmaceutically acceptable salt thereof.

23. A pharmaceutical composition comprising a compound of claim 1, or a pharmaceutically acceptable salt thereof, and a pharmaceutically acceptable carrier.

* * * * *